US011788205B2

(12) United States Patent
Klein et al.

(10) Patent No.: US 11,788,205 B2
(45) Date of Patent: Oct. 17, 2023

(54) CAR-T CELL ASSAY FOR SPECIFICITY TEST OF NOVEL ANTIGEN BINDING MOIETIES

(71) Applicant: Hoffmann-La Roche Inc., Little Falls, NJ (US)

(72) Inventors: Christian Klein, Schlieren (CH); Ekkehard Moessner, Schlieren (CH); Lydia Jasmin Hanisch, Schlieren (CH); Wei Xu, Schlieren (CH); Camille Loise Sophie Delon, Schlieren (CH); Diana Darowski, Schlieren (CH); Christian Jost, Schlieren (CH); Vesna Pulko, Schlieren (CH)

( * ) Notice: Subject to any disclaimer, the term of this patent is extended or adjusted under 35 U.S.C. 154(b) by 159 days.

(21) Appl. No.: 16/906,931

(22) Filed: Jun. 19, 2020

(65) Prior Publication Data
US 2020/0318105 A1   Oct. 8, 2020

Related U.S. Application Data

(63) Continuation of application No. PCT/EP2018/086067, filed on Dec. 20, 2018.

(30) Foreign Application Priority Data

Dec. 21, 2017 (EP) .................................... 17209198

(51) Int. Cl.
| | |
|---|---|
| *C40B 30/04* | (2006.01) |
| *C40B 30/06* | (2006.01) |
| *C07K 16/28* | (2006.01) |
| *C12N 15/10* | (2006.01) |
| *C12N 15/86* | (2006.01) |

(Continued)

(52) U.S. Cl.
CPC .......... *C40B 30/06* (2013.01); *C07K 16/2809* (2013.01); *C12N 15/1037* (2013.01); *C12N 15/1086* (2013.01); *C12N 15/86* (2013.01); *G01N 33/505* (2013.01);
(Continued)

(58) Field of Classification Search
None
See application file for complete search history.

(56) References Cited

U.S. PATENT DOCUMENTS

2016/0051651 A1\* 2/2016 Brogdon ............ A61K 31/7068
435/372.3

FOREIGN PATENT DOCUMENTS

| WO | 2016/014535 A1 | 1/2016 |
| WO | 2016/028896 A1 | 2/2016 |
| WO | 2016/164731 A2 | 10/2016 |

OTHER PUBLICATIONS

Brower, V., "The CAR T-Cell Race" The Scientist (Article Dated: Mar. 31, 2015), (Apr. 1, 2015) https://www.the-scientist.com/?articles.view/articleNo/42462/title/The-CAR-T-Cell-Race/.
(Continued)

*Primary Examiner* — Christian C Boesen
(74) *Attorney, Agent, or Firm* — Lawrence S. Graham

(57) ABSTRACT

The present invention generally relates to specificity assays using cell cultures, in particular to chimeric antigen receptor (CAR) expressing reporter T (CAR-T cell) assays to test antigen binding moieties in different formats. Furthermore, the present invention relates to the use of CAR-T cells, transfected/transduced with an engineered chimeric antigen receptor (CAR) comprising a target antigen binding moiety capable of specific binding to a target antigen, e.g., tumor associated antigens.

21 Claims, 12 Drawing Sheets

Specification includes a Sequence Listing.

(51) Int. Cl.
  *G01N 33/50*  (2006.01)
  *G01N 33/574*  (2006.01)
(52) U.S. Cl.
  CPC ... *G01N 33/57492* (2013.01); *C07K 2317/31* (2013.01); *C12N 2740/15043* (2013.01)

(56) References Cited

OTHER PUBLICATIONS

Chmielewski, M. et al., "TRUCKS: the fourth generation of CARs" Expert Opin Biol Th 15(8):1145-1154 (May 18, 2015).
"International Preliminary Report on Patentability—PCT/EP2018/086067" (Date of Issuance: Jun. 23, 2020),:pp. 1-7 (Jul. 2, 2020).
"International Search Report—PCT/EP2018/086067":pp. 1-7 (Feb. 13, 2019).
Smith, A. J. et al., "Chimeric antigen receptor (CAR) T cell therapy for malignant cancers: Summary and perspective" J Cell Immunother 2(2):59-68 (Nov. 1, 2016).
Anonymous, "scFv/Fab Construction—Antibody Fragments Expression" DetaiBio, Jan. 1, 2018 (Jan. 1, 2018), Retrieved from the Internet: URL:http://www.detaibio.com/en/scFv-Fab-construction.html [retrieved on Apr. 9, 2023], pp. 1-4.
Quintero-Hernandez, V. et al., "The change of the scFv into the Fab format improves the stability (and in vivo toxin neutralization capacity of recombinant antibodies" Molecular Immunology 44(6):1307-1305 (Feb. 1, 2007).

* cited by examiner

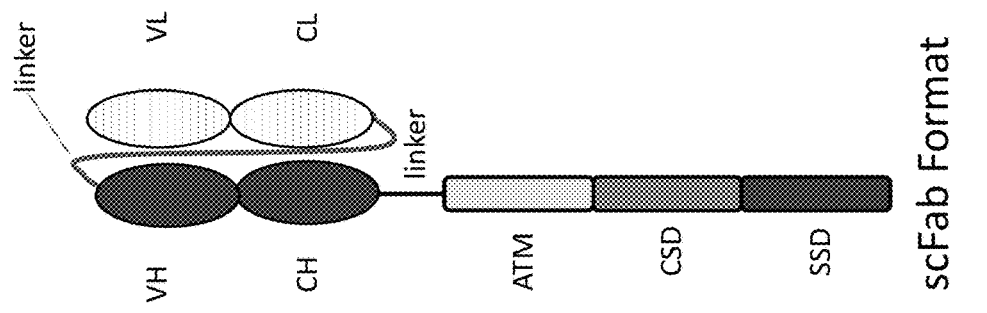
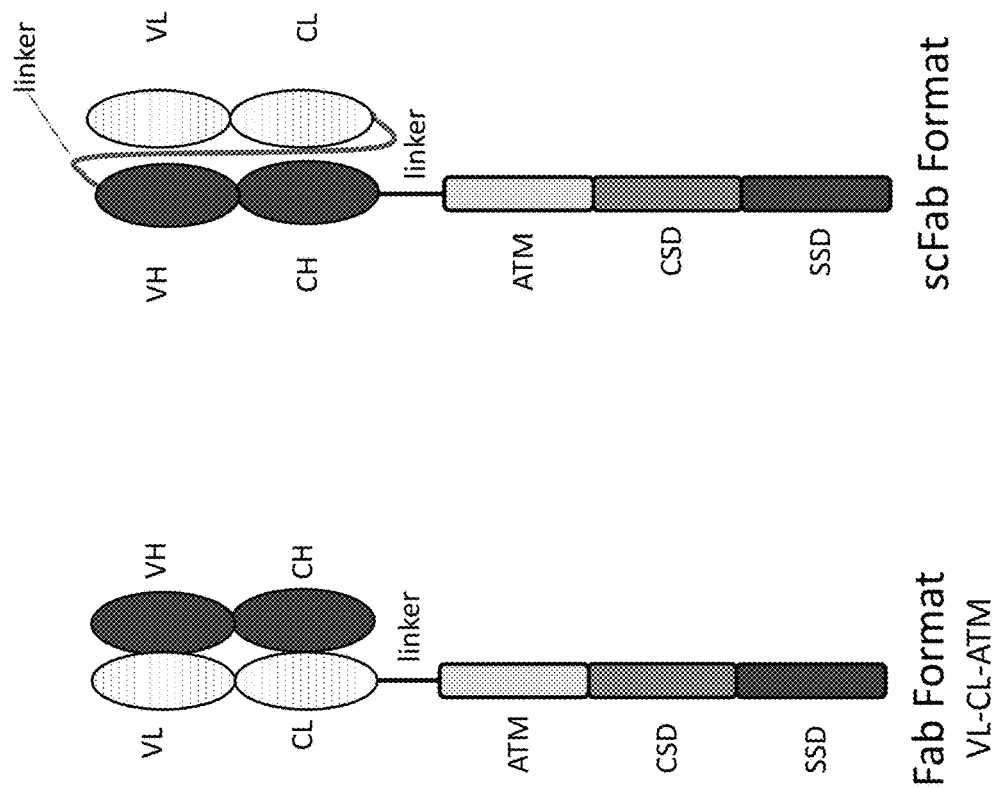
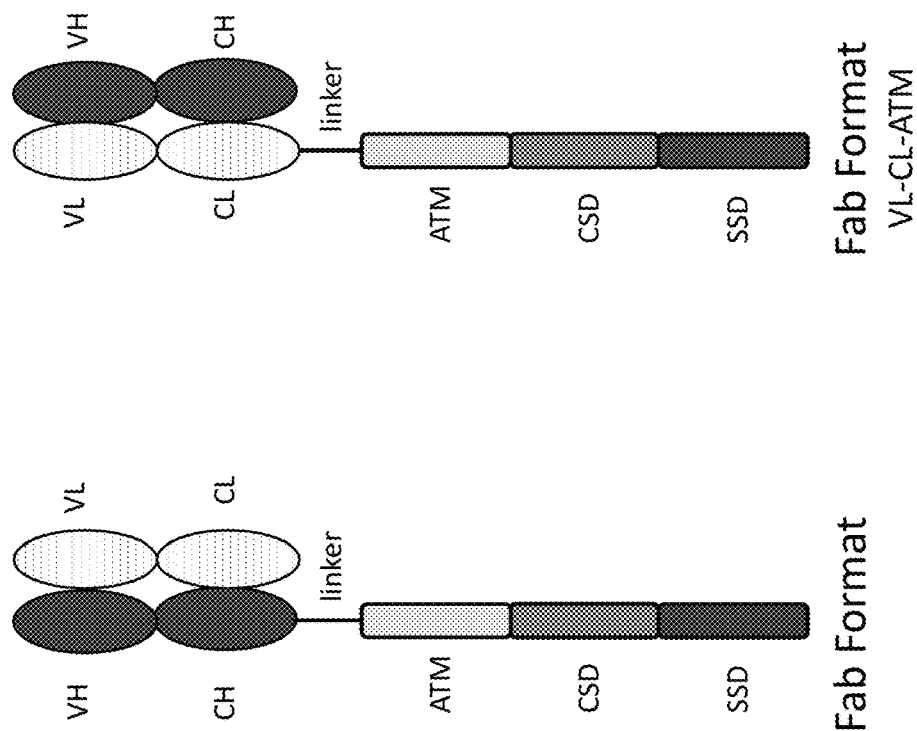

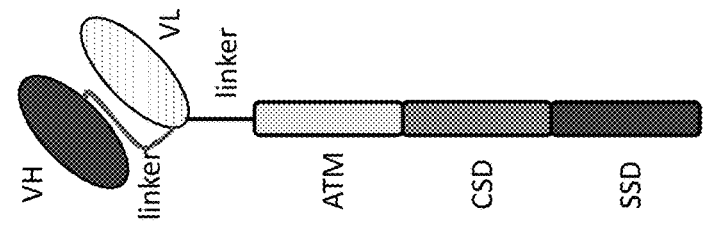
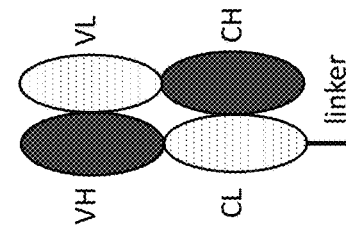
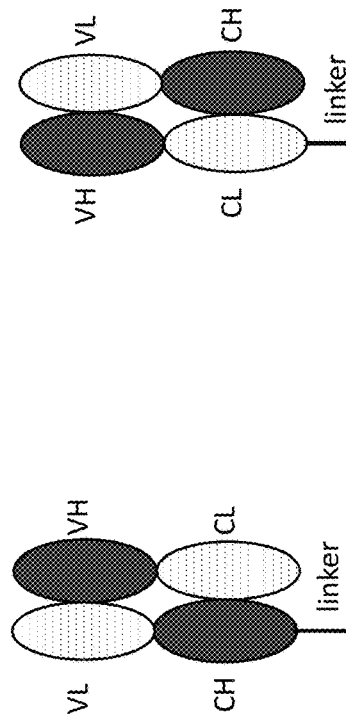
Figure 2D — crossFab Format VL-CH1-ATM
Figure 2E — crossFab Format VH-CL-ATM
Figure 2F — scFv
ATM = anchoring transmembrane domain; CSD = co-stimulatory signaling domain; SSD = stimulatory signaling domain

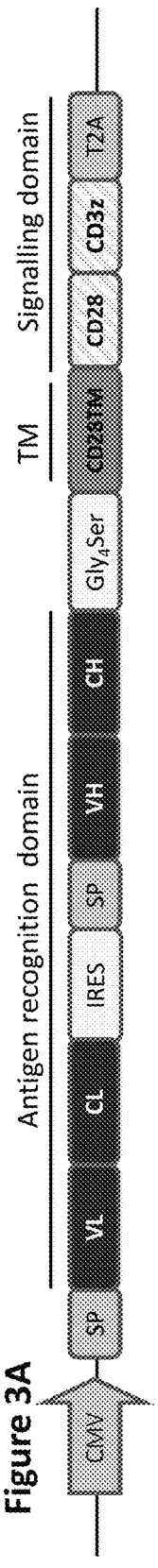
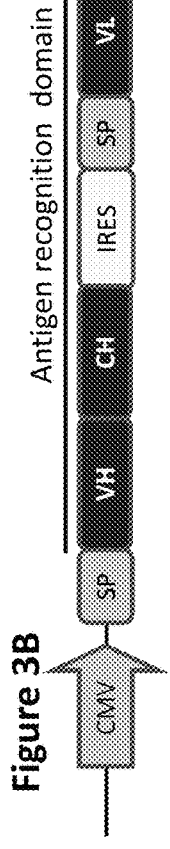
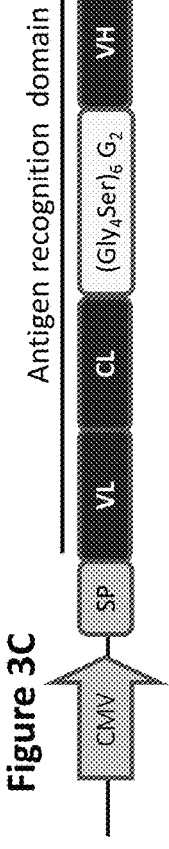
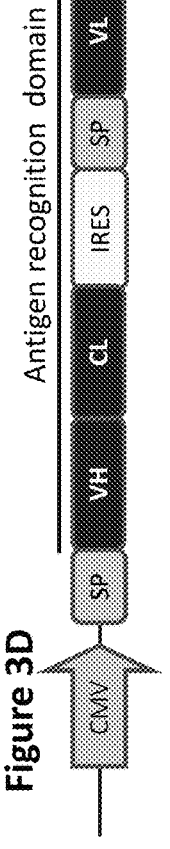
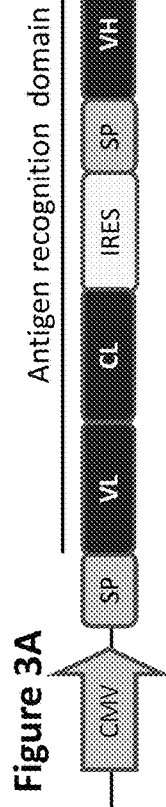
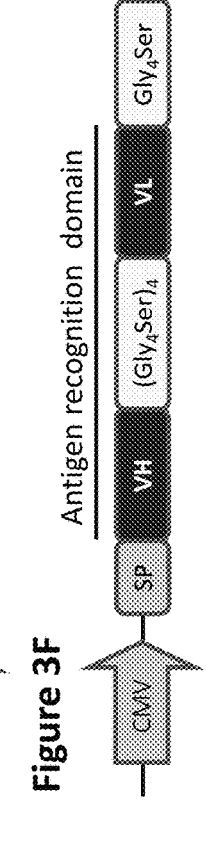
Figure 3A
Figure 3B
Figure 3C
Figure 3D
Figure 3E
Figure 3F
CMV = Cytomegalovirus promotor, SP= Signal peptide, VH = variable heavy chain, VL = variable light chain, TM = transmembrane domain, IRES= internal ribosomal entry site

SEQUENCE LISTING

<160> NUMBER OF SEQ ID NOS: 93

<210> SEQ ID NO 1
<211> LENGTH: 5
<212> TYPE: PRT
<213> ORGANISM: Artificial sequence
<220> FEATURE:
<223> OTHER INFORMATION: Anti-CD20 ( GA101) CDR H1 Kabat

<400> SEQUENCE: 1

Tyr Ser Trp Ile Asn
1               5

<210> SEQ ID NO 2
<211> LENGTH: 17
<212> TYPE: PRT
<213> ORGANISM: Artificial sequence
<220> FEATURE:
<223> OTHER INFORMATION: Anti-CD20 ( GA101) CDR H2 Kabat

<400> SEQUENCE: 2

Arg Ile Phe Pro Gly Asp Gly Asp Thr Asp Tyr Asn Gly Lys Phe Lys
1               5                   10                  15

Gly

<210> SEQ ID NO 3
<211> LENGTH: 10
<212> TYPE: PRT
<213> ORGANISM: Artificial sequence
<220> FEATURE:
<223> OTHER INFORMATION: Anti-CD20 ( GA101) CDR H3 Kabat

<400> SEQUENCE: 3

Asn Val Phe Asp Gly Tyr Trp Leu Val Tyr

```
1               5                    10
```

<210> SEQ ID NO 4
<211> LENGTH: 16
<212> TYPE: PRT
<213> ORGANISM: Artificial sequence
<220> FEATURE:
<223> OTHER INFORMATION: Anti-CD20 ( GA101)   CDR L1 Kabat

<400> SEQUENCE: 4

```
Arg Ser Ser Lys Ser Leu Leu His Ser Asn Gly Ile Thr Tyr Leu Tyr
1               5                   10                  15
```

<210> SEQ ID NO 5
<211> LENGTH: 7
<212> TYPE: PRT
<213> ORGANISM: Artificial sequence
<220> FEATURE:
<223> OTHER INFORMATION: Anti-CD20 ( GA101)   CDR L2 Kabat

<400> SEQUENCE: 5

```
Gln Met Ser Asn Leu Val Ser
1               5
```

<210> SEQ ID NO 6
<211> LENGTH: 9
<212> TYPE: PRT
<213> ORGANISM: Artificial sequence
<220> FEATURE:
<223> OTHER INFORMATION: Anti-CD20 ( GA101)   CDR L3 Kabat

<400> SEQUENCE: 6

```
Ala Gln Asn Leu Glu Leu Pro Tyr Thr
1               5
```

<210> SEQ ID NO 7
<211> LENGTH: 407
<212> TYPE: PRT
<213> ORGANISM: Artificial sequence
<220> FEATURE:
<223> OTHER INFORMATION: Anti-CD20-(GA101)-Fab heavy chain-CD28ATD-
      CD28CSD-CD3zSSD fusion pETR 17097

<400> SEQUENCE: 7

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140
```

```
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Gly Gly
    210                 215                 220

Gly Gly Ser Phe Trp Val Leu Val Val Gly Gly Val Leu Ala Cys
225             230                 235                 240

Tyr Ser Leu Leu Val Thr Val Ala Phe Ile Ile Phe Trp Val Arg Ser
                245                 250                 255

Lys Arg Ser Arg Leu Leu His Ser Asp Tyr Met Asn Met Thr Pro Arg
            260                 265                 270

Arg Pro Gly Pro Thr Arg Lys His Tyr Gln Pro Tyr Ala Pro Pro Arg
        275                 280                 285

Asp Phe Ala Ala Tyr Arg Ser Arg Val Lys Phe Ser Arg Ser Ala Asp
    290                 295                 300

Ala Pro Ala Tyr Gln Gln Gly Gln Asn Gln Leu Tyr Asn Glu Leu Asn
305                 310                 315                 320

Leu Gly Arg Arg Glu Glu Tyr Asp Val Leu Asp Lys Arg Arg Gly Arg
                325                 330                 335

Asp Pro Glu Met Gly Gly Lys Pro Arg Arg Lys Asn Pro Gln Glu Gly
            340                 345                 350

Leu Tyr Asn Glu Leu Gln Lys Asp Lys Met Ala Glu Ala Tyr Ser Glu
        355                 360                 365

Ile Gly Met Lys Gly Glu Arg Arg Arg Gly Lys Gly His Asp Gly Leu
    370                 375                 380

Tyr Gln Gly Leu Ser Thr Ala Thr Lys Asp Thr Tyr Asp Ala Leu His
385                 390                 395                 400

Met Gln Ala Leu Pro Pro Arg
                405

<210> SEQ ID NO 8
<211> LENGTH: 222
<212> TYPE: PRT
<213> ORGANISM: Artificial sequence
<220> FEATURE:
<223> OTHER INFORMATION: Anti-CD20-(GA101)-Fab heavy chain

<400> SEQUENCE: 8

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

```
Ala Arg Asn Val Phe Asp Gly Tyr Trp Leu Val Tyr Trp Gly Gln Gly
                100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys
    210                 215                 220
```

<210> SEQ ID NO 9
<211> LENGTH: 219
<212> TYPE: PRT
<213> ORGANISM: Artificial sequence
<220> FEATURE:
<223> OTHER INFORMATION: Anti-CD20-(GA101)-Fab light chain

<400> SEQUENCE: 9

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
                20                  25                  30

Asn Gly Ile Thr Tyr Leu Tyr Trp Tyr Leu Gln Lys Pro Gly Gln Ser
            35                  40                  45

Pro Gln Leu Leu Ile Tyr Gln Met Ser Asn Leu Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
    115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
    195                 200                 205

Pro Val Thr Lys Ser Phe Asn Arg Gly Glu Cys
210                 215
```

<210> SEQ ID NO 10
<211> LENGTH: 112

<212> TYPE: PRT
<213> ORGANISM: Artificial sequence
<220> FEATURE:
<223> OTHER INFORMATION: Anti-CD20-(GA101) VL

<400> SEQUENCE: 10

Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
            100                 105                 110

<210> SEQ ID NO 11
<211> LENGTH: 107
<212> TYPE: PRT
<213> ORGANISM: Artificial sequence
<220> FEATURE:
<223> OTHER INFORMATION: CL

<400> SEQUENCE: 11

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 12
<211> LENGTH: 119
<212> TYPE: PRT
<213> ORGANISM: Artificial sequence
<220> FEATURE:
<223> OTHER INFORMATION: Anti-CD20-(GA101) VH

<400> SEQUENCE: 12

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe

```
                    50                  55                  60
Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                     85                  90                  95

Ala Arg Asn Val Phe Asp Gly Tyr Trp Leu Val Tyr Trp Gly Gln Gly
                    100                 105                 110

Thr Leu Val Thr Val Ser Ser
        115

<210> SEQ ID NO 13
<211> LENGTH: 103
<212> TYPE: PRT
<213> ORGANISM: Artificial sequence
<220> FEATURE:
<223> OTHER INFORMATION: CH1

<400> SEQUENCE: 13

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys
            100

<210> SEQ ID NO 14
<211> LENGTH: 27
<212> TYPE: PRT
<213> ORGANISM: Artificial sequence
<220> FEATURE:
<223> OTHER INFORMATION: CD28ATD

<400> SEQUENCE: 14

Phe Trp Val Leu Val Val Val Gly Gly Val Leu Ala Cys Tyr Ser Leu
 1               5                  10                  15

Leu Val Thr Val Ala Phe Ile Ile Phe Trp Val
                20                  25

<210> SEQ ID NO 15
<211> LENGTH: 41
<212> TYPE: PRT
<213> ORGANISM: Artificial sequence
<220> FEATURE:
<223> OTHER INFORMATION: CD28CSD

<400> SEQUENCE: 15

Arg Ser Lys Arg Ser Arg Leu Leu His Ser Asp Tyr Met Asn Met Thr
 1               5                  10                  15

Pro Arg Arg Pro Gly Pro Thr Arg Lys His Tyr Gln Pro Tyr Ala Pro
                20                  25                  30

Pro Arg Asp Phe Ala Ala Tyr Arg Ser
             35                  40
```

<210> SEQ ID NO 16
<211> LENGTH: 112
<212> TYPE: PRT
<213> ORGANISM: Artificial sequence
<220> FEATURE:
<223> OTHER INFORMATION: CD3zSSD

<400> SEQUENCE: 16

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 17
<211> LENGTH: 180
<212> TYPE: PRT
<213> ORGANISM: Artificial sequence
<220> FEATURE:
<223> OTHER INFORMATION: CD28ATD-CD28CSD-CD3zSSD

<400> SEQUENCE: 17

Phe Trp Val Leu Val Val Val Gly Gly Val Leu Ala Cys Tyr Ser Leu
1               5                   10                  15

Leu Val Thr Val Ala Phe Ile Ile Phe Trp Val Arg Ser Lys Arg Ser
                20                  25                  30

Arg Leu Leu His Ser Asp Tyr Met Asn Met Thr Pro Arg Arg Pro Gly
            35                  40                  45

Pro Thr Arg Lys His Tyr Gln Pro Tyr Ala Pro Pro Arg Asp Phe Ala
        50                  55                  60

Ala Tyr Arg Ser Arg Val Lys Phe Ser Arg Ser Ala Asp Ala Pro Ala
65                  70                  75                  80

Tyr Gln Gln Gly Gln Asn Gln Leu Tyr Asn Glu Leu Asn Leu Gly Arg
                85                  90                  95

Arg Glu Glu Tyr Asp Val Leu Asp Lys Arg Arg Gly Arg Asp Pro Glu
            100                 105                 110

Met Gly Gly Lys Pro Arg Arg Lys Asn Pro Gln Glu Gly Leu Tyr Asn
        115                 120                 125

Glu Leu Gln Lys Asp Lys Met Ala Glu Ala Tyr Ser Glu Ile Gly Met
    130                 135                 140

Lys Gly Glu Arg Arg Arg Gly Lys Gly His Asp Gly Leu Tyr Gln Gly
145                 150                 155                 160

Leu Ser Thr Ala Thr Lys Asp Thr Tyr Asp Ala Leu His Met Gln Ala
                165                 170                 175

Leu Pro Pro Arg
            180

```
<210> SEQ ID NO 18
<211> LENGTH: 238
<212> TYPE: PRT
<213> ORGANISM: Artificial sequence
<220> FEATURE:
<223> OTHER INFORMATION: eGFP

<400> SEQUENCE: 18
```

Val Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr Leu Gly Met Asp Glu Leu Tyr Lys
225                 230                 235

```
<210> SEQ ID NO 19
<211> LENGTH: 20
<212> TYPE: PRT
<213> ORGANISM: Artificial sequence
<220> FEATURE:
<223> OTHER INFORMATION: (G4S)4 linker

<400> SEQUENCE: 19
```

Gly Gly Gly Gly Ser Gly Gly Gly Gly Ser Gly Gly Gly Gly Ser Gly
1               5                   10                  15

Gly Gly Gly Ser
            20

```
<210> SEQ ID NO 20
<211> LENGTH: 5
<212> TYPE: PRT
<213> ORGANISM: Artificial sequence
<220> FEATURE:
<223> OTHER INFORMATION: G4S linker

<400> SEQUENCE: 20
```

```
<210> SEQ ID NO 21
<211> LENGTH: 19
<212> TYPE: PRT
<213> ORGANISM: Artificial sequence
<220> FEATURE:
<223> OTHER INFORMATION: T2A linker

<400> SEQUENCE: 21

Gly Glu Gly Arg Gly Ser Leu Leu Thr Cys Gly Asp Val Glu Glu Asn
1               5                   10                  15

Pro Gly Pro

<210> SEQ ID NO 22
<211> LENGTH: 2659
<212> TYPE: DNA
<213> ORGANISM: Artificial sequence
<220> FEATURE:
<223> OTHER INFORMATION: Anti-CD20-(GA101)-Fab-CD28ATD-CD28CSD-CD3zSSD
      pETR17097

<400> SEQUENCE: 22
atgggatgga gctgtatcat cctcttcttg gtagcaacag ctaccggtgt gcattccgat     60
atcgtgatga cccagactcc actctccctg cccgtcaccc tgggagagcc cgccagcatt    120
agctgcaggt ctagcaagag cctcttgcac agcaatggca tcacttattt gtattggtac    180
ctgcaaaagc cagggcagtc tccacagctc ctgatttatc aaatgtccaa ccttgtctct    240
ggcgtccctg accggttctc cggatccggg tcaggcactg atttcacact gaaaatcagc    300
agggtggagc tgaggatgt tggagtttat tactgcgctc agaatctaga acttccttac     360
accttcggcg agggaccaa ggtggagatc aaaccgtacg gtggctgcac catctgtctt    420
catcttcccg ccatctgatg agcagttgaa atctggaact gcctctgttg tgtgcctgct    480
gaataacttc tatcccagag aggccaaagt acagtggaag gtggataacg ccctccaatc    540
gggtaactcc caggagagtg tcacagagca ggacagcaag gacagcacct acagcctcag    600
cagcaccctg acgctgagca agcagactac gagaaacac aaagtctacg cctgcgaagt    660
cacccatcag ggcctgagct cgcccgtcac aaagagcttc aacaggggag agtgttagaa    720
tagaattccc cgaagtaact tagaagctgt aaatcaacga tcaatagcag gtgtggcaca    780
ccagtcatac cttgatcaag cacttctgtt tccccggact gagtatcaat aggctgctcg    840
cgcggctgaa ggagaaaacg ttcgttaccc gaccaactac ttcgagaagc ttagtaccac    900
catgaacgag gcagggtgtt cgctcagca aaccccagt gtagatcagg ctgatgagtc    960
actgcaaccc ccatgggcga ccatggcagt ggctgcgttg gcggcctgcc catggagaaa   1020
tccatgggac gctctaattc tgacatggtg tgaagtgcct attgagctaa ctggtagtcc   1080
tccggcccct gattgcggct aatcctaact gcggagcaca tgctcacaaa ccagtgggtg   1140
gtgtgtcgta acgggcaact ctgcagcgga accgactact ttgggtgtcc gtgtttcctt   1200
ttattcctat attggctgct tatggtgaca atcaaaaagt tgttaccata tagctattgg   1260
attggccatc cggtgtgcaa cagggcaact gtttacctat ttattggttt tgtaccatta   1320
tcactgaagt ctgtgatcac tctcaaattc attttgaccc tcaacacaat caaacgccac   1380
catgggatgg agctgtatca tcctcttctt ggtagcaaca gctaccggtg tgcactccca   1440
ggtgcaattg gtgcagtctg gcgctgaagt taagaagcct gggagttcag tgaaggtctc   1500
```

| | |
|---|---|
| ctgcaaggct tcgggatacg ccttcagcta ttcttggatc aattgggtgc ggcaggcgcc | 1560 |
| tggacaaggg ctcgagtgga tgggacggat ctttcccggc gatggggata ctgactacaa | 1620 |
| tgggaaattc aagggcagag tcacaattac cgccgacaaa tccactagca cagcctatat | 1680 |
| ggagctgagc agcctgagat ctgaggacac ggccgtgtat tactgtgcaa gaaatgtctt | 1740 |
| tgatggttac tggcttgttt actggggcca gggaaccctg gtcaccgtct ccagcgctag | 1800 |
| caccaagggc cctccgtgt tccccctggc cccagcagc aagagcacca gcggcggcac | 1860 |
| agccgctctg gctgcctgg tcaaggacta cttccccgag cccgtgaccg tgtcctggaa | 1920 |
| cagcggagcc ctgaccctcc ggcgtgcacac cttccccgcc gtgctgcaga gttctggcct | 1980 |
| gtatagcctg agcagcgtgg tcaccgtgcc ttctagcagc ctgggcaccc agacctacat | 2040 |
| ctgcaacgtg aaccaaagc ccagcaacac caaggtggac aagaaggtgg agcccaagag | 2100 |
| ctgcggaggg ggcggatcct tctgggtgct ggtggtggtg ggcggcgtgc tggcctgcta | 2160 |
| cagcctgctg gtgaccgtgg ccttcatcat cttctgggtg aggagcaaga ggagcaggct | 2220 |
| gctgcacagc gactacatga acatgacccc caggaggccc ggccccacca ggaagcacta | 2280 |
| ccagccctac gccccccca gggacttcgc cgcctacagg agcagggtga agttcagcag | 2340 |
| gagcgccgac gcccccgcct accagcaggg ccagaaccag ctgtataacg agctgaacct | 2400 |
| gggcaggagg gaggagtacg acgtgctgga caagaggagg ggcagggacc ccagagatggg | 2460 |
| cggcaagccc aggaggaaga accccccagga gggcctgtat aacgagctgc agaaggacaa | 2520 |
| gatggccgag gcctacagcg agatcggcat gaagggcgag aggaggaggg gcaagggcca | 2580 |
| cgacggcctg taccagggcc tgagcaccgc caccaaggac acctacgacg ccctgcacat | 2640 |
| gcaggccctg ccccccagg | 2659 |

<210> SEQ ID NO 23
<211> LENGTH: 336
<212> TYPE: DNA
<213> ORGANISM: Artificial sequence
<220> FEATURE:
<223> OTHER INFORMATION: Anti-CD20-(GA101)-Fab-VL

<400> SEQUENCE: 23

| | |
|---|---|
| gatatcgtga tgacccagac tccactctcc ctgcccgtca cccctggaga gccgccagc | 60 |
| attagctgca ggtctagcaa gagcctcttg cacagcaatg gcatcactta tttgtattgg | 120 |
| tacctgcaaa agccagggca gtctccacag ctcctgattt atcaaatgtc caaccttgtc | 180 |
| tctggcgtcc ctgaccggtt ctccggatcc gggtcaggca ctgatttcac actgaaaatc | 240 |
| agcagggtgg aggctgagga tgttggagtt tattactgcg ctcagaatct agaacttcct | 300 |
| tacaccttcg gcggagggac caaggtggag atcaaa | 336 |

<210> SEQ ID NO 24
<211> LENGTH: 324
<212> TYPE: DNA
<213> ORGANISM: Artificial sequence
<220> FEATURE:
<223> OTHER INFORMATION: Fab CL

<400> SEQUENCE: 24

| | |
|---|---|
| cgtacggtgg ctgcaccatc tgtcttcatc ttcccgccat ctgatgagca gttgaaatct | 60 |
| ggaactgcct ctgttgtgtg cctgctgaat aacttctatc ccagagaggc caaagtacag | 120 |
| tggaaggtgg ataacgccct ccaatcgggt aactcccagg agagtgtcac agagcaggac | 180 |

| | |
|---|---|
| agcaaggaca gcacctacag cctcagcagc accctgacgc tgagcaaagc agactacgag | 240 |
| aaacacaaag tctacgcctg cgaagtcacc catcagggcc tgagctcgcc cgtcacaaag | 300 |
| agcttcaaca ggggagagtg ttag | 324 |

<210> SEQ ID NO 25
<211> LENGTH: 357
<212> TYPE: DNA
<213> ORGANISM: Artificial sequence
<220> FEATURE:
<223> OTHER INFORMATION: Anti-CD20-(GA101)-Fab-VH

<400> SEQUENCE: 25

| | |
|---|---|
| caggtgcaat tggtgcagtc tggcgctgaa gttaagaagc ctgggagttc agtgaaggtc | 60 |
| tcctgcaagg cttcgggata cgccttcagc tattcttgga tcaattgggt gcggcaggcg | 120 |
| cctggacaag ggctcgagtg gatgggacgg atctttcccg gcgatgggga tactgactac | 180 |
| aatgggaaat tcaagggcag agtcacaatt accgccgaca aatccactag cacagcctat | 240 |
| atggagctga gcagcctgag atctgaggac acggccgtgt attactgtgc aagaaatgtc | 300 |
| tttgatggtt actggcttgt ttactggggc cagggaaccc tggtcaccgt ctccagc | 357 |

<210> SEQ ID NO 26
<211> LENGTH: 309
<212> TYPE: DNA
<213> ORGANISM: Artificial sequence
<220> FEATURE:
<223> OTHER INFORMATION: Fab CH1

<400> SEQUENCE: 26

| | |
|---|---|
| gctagcacca agggcccctc cgtgttcccc ctggccccca gcagcaagag caccagcggc | 60 |
| ggcacagccg ctctgggctg cctggtcaag gactacttcc ccgagcccgt gaccgtgtcc | 120 |
| tggaacagcg gagccctgac ctccggcgtg cacaccttcc ccgccgtgct gcagagttct | 180 |
| ggcctgtata gcctgagcag cgtggtcacc gtgccttcta gcagcctggg cacccagacc | 240 |
| tacatctgca acgtgaacca caagcccagc aacaccaagg tggacaagaa ggtggagccc | 300 |
| aagagctgc | 309 |

<210> SEQ ID NO 27
<211> LENGTH: 647
<212> TYPE: DNA
<213> ORGANISM: Artificial sequence
<220> FEATURE:
<223> OTHER INFORMATION: IRES EV71 internal ribosomal entry side

<400> SEQUENCE: 27

| | |
|---|---|
| cccgaagtaa cttagaagct gtaaatcaac gatcaatagc aggtgtggca caccagtcat | 60 |
| accttgatca agcacttctg tttccccgga ctgagtatca ataggctgct cgcgcggctg | 120 |
| aaggagaaaa cgttcgttac ccgaccaact acttcgagaa gcttagtacc accatgaacg | 180 |
| aggcagggtg tttcgctcag cacaaccccca gtgtagatca ggctgatgag tcactgcaac | 240 |
| ccccatgggc gaccatggca gtggctgcgt tggcggcctg cccatggaga atccatggg | 300 |
| acgctctaat tctgacatgg tgtgaagtgc ctattgagct aactggtagt cctccggccc | 360 |
| ctgattgcgg ctaatcctaa ctgcggagca catgctcaca aaccagtggg tggtgtgtcg | 420 |
| taacgggcaa ctctgcagcg gaaccgacta ctttgggtgt ccgtgtttcc ttttattcct | 480 |
| atattggctg cttatggtga caatcaaaaa gttgttacca tatagctatt ggattggcca | 540 |
| tccggtgtgc aacagggcaa ctgtttacct atttattggt tttgtaccat tatcactgaa | 600 |

```
gtctgtgatc actctcaaat tcattttgac cctcaacaca atcaaac                    647
```

<210> SEQ ID NO 28
<211> LENGTH: 15
<212> TYPE: DNA
<213> ORGANISM: Artificial sequence
<220> FEATURE:
<223> OTHER INFORMATION: G4S linker

<400> SEQUENCE: 28

```
ggaggggggcg gatcc                                                       15
```

<210> SEQ ID NO 29
<211> LENGTH: 81
<212> TYPE: DNA
<213> ORGANISM: Artificial sequence
<220> FEATURE:
<223> OTHER INFORMATION: CD28ATD

<400> SEQUENCE: 29

```
ttttgggtgc tggtggtggt tggtggagtc ctggcttgct atagcttgct agtaacagtg      60
gcctttatta ttttctgggt g                                                 81
```

<210> SEQ ID NO 30
<211> LENGTH: 123
<212> TYPE: DNA
<213> ORGANISM: Artificial sequence
<220> FEATURE:
<223> OTHER INFORMATION: CD28CSD

<400> SEQUENCE: 30

```
aggagtaaga ggagcaggct cctgcacagt gactacatga acatgactcc ccgccgcccc      60
gggcccaccc gcaagcatta ccagccctat gccccaccac gcgacttcgc agcctatcgc     120
tcc                                                                    123
```

<210> SEQ ID NO 31
<211> LENGTH: 336
<212> TYPE: DNA
<213> ORGANISM: Artificial sequence
<220> FEATURE:
<223> OTHER INFORMATION: CD3zSSD

<400> SEQUENCE: 31

```
agagtgaagt tcagcaggag cgcagacgcc cccgcgtacc agcagggcca gaaccagctc      60
tataacgagc tcaatctagg acgaagagag gagtacgatg ttttggacaa gagacgtggc     120
cgggaccctg agatgggggg aaagccgaga aggaagaacc ctcaggaagg cctgtacaat     180
gaactgcaga aagataagat ggcggaggcc tacagtgaga ttgggatgaa aggcgagcgc     240
cggaggggca aggggcacga tggcctttac caggtctca gtacagccac caaggacacc     300
tacgacgccc ttcacatgca ggccctgccc cctcgc                                336
```

<210> SEQ ID NO 32
<211> LENGTH: 540
<212> TYPE: DNA
<213> ORGANISM: Artificial sequence
<220> FEATURE:
<223> OTHER INFORMATION: CD28ATD-CD28CSD-CD3zSSD

<400> SEQUENCE: 32

```
ttctgggtgc tggtggtggt gggcggcgtg ctggcctgct acagcctgct ggtgaccgtg      60
```

```
gccttcatca tcttctgggt gaggagcaag aggagcaggc tgctgcacag cgactacatg    120
aacatgaccc ccaggaggcc cggccccacc aggaagcact accagcccta cgccccccc     180 agggacttcg ccgcctacag gagcagggtg aagttcagca ggagcgccga cgccccgcc     240 taccagcagg gccagaacca gctgtataac gagctgaacc tgggcaggag ggaggagtac    300
gacgtgctgg acaagaggag gggcagggac cccgagatgg gcggcaagcc caggaggaag    360 aaccccagg agggcctgta taacgagctg cagaaggaca gatggccga ggcctacagc      420 gagatcggca tgaagggcga gaggaggagg ggcaagggcc acgacggcct gtaccagggc    480
ctgagcaccg ccaccaagga cacctacgac gccctgcaca tgcaggccct gcccccagg    540
```

<210> SEQ ID NO 33
<211> LENGTH: 63
<212> TYPE: DNA
<213> ORGANISM: Artificial sequence
<220> FEATURE:
<223> OTHER INFORMATION: T2A linker

<400> SEQUENCE: 33

```
tccggagagg gcagaggaag tcttctaaca tgcggtgacg tggaggagaa tcccggccct    60
agg                                                                  63
```

<210> SEQ ID NO 34
<211> LENGTH: 717
<212> TYPE: DNA
<213> ORGANISM: Artificial sequence
<220> FEATURE:
<223> OTHER INFORMATION: eGFP

<400> SEQUENCE: 34

```
gtgagcaagg gcgaggagct gttcaccggg gtggtgccca tcctggtcga gctggacggc    60
gacgtaaacg gccacaagtt cagcgtgtcc ggcgagggcg agggcgatgc cacctacggc    120
aagctgaccc tgaagttcat ctgcaccacc ggcaagctgc ccgtgccctg gcccaccctc    180
gtgaccaccc tgacctacgg cgtgcagtgc ttcagccgct accccgacca catgaagcag    240
cacgacttct tcaagtccgc catgcccgaa ggctacgtcc aggagcgcac catcttcttc    300
aaggacgacg gcaactacaa gacccgcgcc gaggtgaagt tcgagggcga caccctggtg    360
aaccgcatcg agctgaaggg catcgacttc aaggaggacg gcaacatcct ggggcacaag    420
ctggagtaca actacaacag ccacaacgtc tatatcatgg ccgacaagca gaagaacggc    480
atcaaggtga acttcaagat ccgccacaac atcgaggacg gcagcgtgca gctcgccgac    540
cactaccagc agaacacccc catcggcgac ggccccgtgc tgctgcccga caaccactac    600
ctgagcaccc agtccgccct gagcaaagac cccaacgaga gcgcgatca catggtcctg    660 ctggagttcg tgaccgccgc cgggatcact ctcggcatgg acgagctgta caagtga      717
```

<210> SEQ ID NO 35
<211> LENGTH: 3438
<212> TYPE: DNA
<213> ORGANISM: Artificial sequence
<220> FEATURE:
<223> OTHER INFORMATION: Anti-CD20-(GA101)-Fab-CD28ATD-CD28CSD-CD3zSSD-
   eGFP pETR17097

<400> SEQUENCE: 35

```
atgggatgga gctgtatcat cctcttcttg gtagcaacag ctaccggtgt gcattccgat    60
atcgtgatga cccagactcc actctccctg cccgtcaccc ctggagagcc cgccagcatt    120
```

-continued

```
agctgcaggt ctagcaagag cctcttgcac agcaatggca tcacttattt gtattggtac    180
ctgcaaaagc cagggcagtc tccacagctc ctgatttatc aaatgtccaa ccttgtctct    240
ggcgtccctg accggttctc cggatccggg tcaggcactg atttcacact gaaaatcagc    300
agggtggagc tgaggatgt tggagtttat tactgcgctc agaatctaga acttccttac     360
accttcggcg agggaccaa ggtggagatc aaacgtacgg tggctgcacc atctgtcttc     420
atcttcccgc catctgatga gcagttgaaa tctggaactg cctctgttgt gtgcctgctg    480
aataacttct atcccagaga ggccaaagta cagtggaagg tggataacgc cctccaatcg    540
ggtaactccc aggagagtgt cacagagcag gacagcaagg acagcaccta cagcctcagc    600
agcaccctga cgctgagcaa agcagactac gagaaacaca agtctacgc ctgcgaagtc     660 acccatcagg gcctgagctc gcccgtcaca aagagcttca caggggaga gtgttagaat     720 agaattcccc gaagtaactt agaagctgta atcaacgat caatagcagg tgtggcacac     780
cagtcatacc ttgatcaagc acttctgttt ccccggactg agtatcaata ggctgctcgc    840
gcggctgaag agaaaacgt tcgttacccg accaactact tcgagaagct tagtaccacc     900
atgaacgagg cagggtgttt cgctcagcac aaccccagtg tagatcaggc tgatgagtca    960
ctgcaacccc catgggcgac catggcagtg gctgcgttgg cggcctgccc atggagaaat   1020
ccatgggacg ctctaattct gacatggtgt gaagtgccta ttgagctaac tggtagtcct   1080
ccggcccctg attgcggcta atcctaactg cggagcacat gctcacaaac cagtgggtgg   1140
tgtgtcgtaa cgggcaactc tgcagcggaa ccgactactt tgggtgtccg tgtttccttt   1200
tattcctata ttggctgctt atggtgacaa tcaaaaagtt gttaccatat agctattgga   1260
ttggccatcc ggtgtgcaac agggcaactg tttacctatt tattggtttt gtaccattat   1320
cactgaagtc tgtgatcact ctcaaattca ttttgaccct caacacaatc aaacgccacc   1380
atgggatgga gctgtatcat cctcttcttg gtagcaacag ctaccggtgt gcactcccag   1440
gtgcaattgg tgcagtctgg cgctgaagtt aagaagcctg ggagttcagt gaaggtctcc   1500
tgcaaggctt cgggatacgc cttcagctat tcttggatca attgggtgcg gcaggcgcct   1560
ggacaagggc tcgagtggat gggacggatc tttcccggcg atggggatac tgactacaat   1620
gggaaattca agggcagagt cacaattacc gccgacaaat ccactagcac agcctatatg   1680
gagctgagca gcctgagatc tgaggacacg gccgtgtatt actgtgcaag aaatgtcttt   1740
gatggttact ggcttgttta ctggggccag ggaaccctgg tcaccgtctc cagcgctagc   1800
accaagggcc cctccgtgtt ccccctggcc ccagcagca agagcaccag cggcggcaca   1860
gccgctctgg gctgcctggt caaggactac ttccccgagc ccgtgaccgt gtcctggaac   1920
agcggagccc tgacctccgg cgtgcacacc ttccccgccg tgctgcagag ttctggcctg   1980
tatagcctga gcagcgtggt caccgtgcct tctagcagcc tgggcaccca gacctacatc   2040
tgcaacgtga accacaagcc cagcaacacc aaggtggaca agaaggtgga gcccaagagc   2100 tgcgagggg gcggatcctt ctgggtgctg gtggtggtgg gcggcgtgct ggcctgctac   2160
agcctgctgg tgaccgtggc cttcatcatc ttctgggtga ggagcaagag gagcaggctg   2220
ctgcacagcg actacatgaa catgaccccc aggaggcccg ccccaccag gaagcactac   2280 cagccctacg cccccccag ggacttcgcc gcctacagga gcagggtgaa gttcagcagg   2340
agcgccgacg cccccgccta ccagcagggc cagaaccagc tgtataacga gctgaacctg   2400
ggcaggaggg aggagtacga cgtgctggac aagaggaggg gcagggaccc cgagatgggc   2460
ggcaagccca ggaggaagaa ccccccaggag ggcctgtata acgagctgca gaaggacaag   2520
```

```
atggccgagg cctacagcga gatcggcatg aagggcgaga ggaggagggg caagggccac    2580
gacggcctgt accagggcct gagcaccgcc accaaggaca cctacgacgc cctgcacatg    2640
caggccctgc cccccaggtc cggagagggc agaggaagtc ttctaacatg cggtgacgtg    2700
gaggagaatc ccggccctag ggtgagcaag ggcgaggagc tgttcaccgg ggtggtgccc    2760
atcctggtcg agctggacgg cgacgtaaac ggccacaagt tcagcgtgtc cggcgagggc    2820
gagggcgatg ccacctacgg caagctgacc ctgaagttca tctgcaccac cggcaagctg    2880
cccgtgccct ggcccaccct cgtgaccacc ctgacctacg gcgtgcagtg cttcagccgc    2940
taccccgacc acatgaagca gcacgacttc ttcaagtccg ccatgcccga aggctacgtc    3000
caggagcgca ccatcttctt caaggacgac ggcaactaca gacccgcgc cgaggtgaag    3060 ttcgagggcg acaccctggt gaaccgcatc gagctgaagg gcatcgactt caaggaggac    3120
ggcaacatcc tggggcacaa gctggagtac aactacaaca gccacaacgt ctatatcatg    3180
gccgacaagc agaagaacgg catcaaggtg aacttcaaga tccgccacaa catcgaggac    3240
ggcagcgtgc agctcgccga ccactaccag cagaacaccc ccatcggcga cggccccgtg    3300
ctgctgcccg acaaccacta cctgagcacc cagtccgccc tgagcaaaga ccccaacgag    3360
aagcgcgatc acatggtcct gctggagttc gtgaccgccg ccgggatcac tctcggcatg    3420
gacgagctgt acaagtga                                                  3438

<210> SEQ ID NO 36
<211> LENGTH: 411
<212> TYPE: PRT
<213> ORGANISM: Artificial sequence
<220> FEATURE:
<223> OTHER INFORMATION: Anti-CD20-(GA101)-crossFab VH-CL light
      chain-ATD-CD28ATD-CD28CSD-CD3zSSD fusion pETR17098

<400> SEQUENCE: 36
```

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser Ala Ser Val Ala Ala Pro Ser Val Phe
        115                 120                 125

Ile Phe Pro Pro Ser Asp Glu Gln Leu Lys Ser Gly Thr Ala Ser Val
    130                 135                 140

Val Cys Leu Leu Asn Asn Phe Tyr Pro Arg Glu Ala Lys Val Gln Trp
145                 150                 155                 160

Lys Val Asp Asn Ala Leu Gln Ser Gly Asn Ser Gln Glu Ser Val Thr
                165                 170                 175

Glu Gln Asp Ser Lys Asp Ser Thr Tyr Ser Leu Ser Ser Thr Leu Thr
            180                 185                 190

Leu Ser Lys Ala Asp Tyr Glu Lys His Lys Val Tyr Ala Cys Glu Val
            195                 200                 205

Thr His Gln Gly Leu Ser Ser Pro Val Thr Lys Ser Phe Asn Arg Gly
        210                 215                 220

Glu Cys Gly Gly Gly Ser Phe Trp Val Leu Val Val Val Gly Gly
225                 230                 235                 240

Val Leu Ala Cys Tyr Ser Leu Leu Val Thr Val Ala Phe Ile Ile Phe
                245                 250                 255

Trp Val Arg Ser Lys Arg Ser Arg Leu Leu His Ser Asp Tyr Met Asn
            260                 265                 270

Met Thr Pro Arg Arg Pro Gly Pro Thr Arg Lys His Tyr Gln Pro Tyr
        275                 280                 285

Ala Pro Pro Arg Asp Phe Ala Ala Tyr Arg Ser Arg Val Lys Phe Ser
    290                 295                 300

Arg Ser Ala Asp Ala Pro Ala Tyr Gln Gln Gly Gln Asn Gln Leu Tyr
305                 310                 315                 320

Asn Glu Leu Asn Leu Gly Arg Arg Glu Glu Tyr Asp Val Leu Asp Lys
                325                 330                 335

Arg Arg Gly Arg Asp Pro Glu Met Gly Gly Lys Pro Arg Arg Lys Asn
            340                 345                 350

Pro Gln Glu Gly Leu Tyr Asn Glu Leu Gln Lys Asp Lys Met Ala Glu
        355                 360                 365

Ala Tyr Ser Glu Ile Gly Met Lys Gly Glu Arg Arg Arg Gly Lys Gly
    370                 375                 380

His Asp Gly Leu Tyr Gln Gly Leu Ser Thr Ala Thr Lys Asp Thr Tyr
385                 390                 395                 400

Asp Ala Leu His Met Gln Ala Leu Pro Pro Arg
                405                 410

<210> SEQ ID NO 37
<211> LENGTH: 226
<212> TYPE: PRT
<213> ORGANISM: Artificial sequence
<220> FEATURE:
<223> OTHER INFORMATION: Anti-CD20-(GA101)-crossFab VH-CL light chain
      pETR17098

<400> SEQUENCE: 37

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
                100                 105                 110

Thr Leu Val Thr Val Ser Ser Ala Ser Val Ala Ala Pro Ser Val Phe
            115                 120                 125

Ile Phe Pro Pro Ser Asp Glu Gln Leu Lys Ser Gly Thr Ala Ser Val

```
                    130                 135                 140
Val Cys Leu Leu Asn Asn Phe Tyr Pro Arg Glu Ala Lys Val Gln Trp
145                 150                 155                 160

Lys Val Asp Asn Ala Leu Gln Ser Gly Asn Ser Gln Glu Ser Val Thr
                165                 170                 175

Glu Gln Asp Ser Lys Asp Ser Thr Tyr Ser Leu Ser Ser Thr Leu Thr
                180                 185                 190

Leu Ser Lys Ala Asp Tyr Glu Lys His Lys Val Tyr Ala Cys Glu Val
                195                 200                 205

Thr His Gln Gly Leu Ser Ser Pro Val Thr Lys Ser Phe Asn Arg Gly
                210                 215                 220

Glu Cys
225

<210> SEQ ID NO 38
<211> LENGTH: 217
<212> TYPE: PRT
<213> ORGANISM: Artificial sequence
<220> FEATURE:
<223> OTHER INFORMATION: Anti-CD20-(GA101)-crossFab VL-CH1 heavy chain-
      pETR17098

<400> SEQUENCE: 38

Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
                20                  25                  30

Asn Gly Ile Thr Tyr Leu Tyr Trp Tyr Leu Gln Lys Pro Gly Gln Ser
            35                  40                  45

Pro Gln Leu Leu Ile Tyr Gln Met Ser Asn Leu Val Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
                100                 105                 110

Ser Ser Ala Ser Thr Lys Gly Pro Ser Val Phe Pro Leu Ala Pro Ser
            115                 120                 125

Ser Lys Ser Thr Ser Gly Gly Thr Ala Ala Leu Gly Cys Leu Val Lys
        130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
                180                 185                 190

Gln Thr Tyr Ile Cys Asn Val Asn His Lys Pro Ser Asn Thr Lys Val
            195                 200                 205

Asp Lys Lys Val Glu Pro Lys Ser Cys
        210                 215

<210> SEQ ID NO 39
<211> LENGTH: 107
<212> TYPE: PRT
<213> ORGANISM: Artificial sequence
<220> FEATURE:
```

<223> OTHER INFORMATION: crossFab CL

<400> SEQUENCE: 39

```
Ala Ser Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 40
<211> LENGTH: 105
<212> TYPE: PRT
<213> ORGANISM: Artificial sequence
<220> FEATURE:
<223> OTHER INFORMATION: crossFab CH1

<400> SEQUENCE: 40

```
Ser Ser Ala Ser Thr Lys Gly Pro Ser Val Phe Pro Leu Ala Pro Ser
1               5                   10                  15

Ser Lys Ser Thr Ser Gly Gly Thr Ala Ala Leu Gly Cys Leu Val Lys
            20                  25                  30

Asp Tyr Phe Pro Glu Pro Val Thr Val Ser Trp Asn Ser Gly Ala Leu
        35                  40                  45

Thr Ser Gly Val His Thr Phe Pro Ala Val Leu Gln Ser Ser Gly Leu
    50                  55                  60

Tyr Ser Leu Ser Ser Val Val Thr Val Pro Ser Ser Ser Leu Gly Thr
65                  70                  75                  80

Gln Thr Tyr Ile Cys Asn Val Asn His Lys Pro Ser Asn Thr Lys Val
                85                  90                  95

Asp Lys Lys Val Glu Pro Lys Ser Cys
            100                 105
```

<210> SEQ ID NO 41
<211> LENGTH: 402
<212> TYPE: PRT
<213> ORGANISM: Artificial sequence
<220> FEATURE:
<223> OTHER INFORMATION: Anti-CD20-(GA101)-crossFab VL-CH1
    heavy-chain-ATD-CD28ATD-CD28CSD-CD3zSSD fusion

<400> SEQUENCE: 41

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Val Ser Gly Val Pro
    50                  55                  60
```

```
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ala Gln Asn
                 85                  90                  95

Leu Glu Leu Pro Tyr Thr Phe Gly Gly Gly Thr Lys Val Glu Ile Lys
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Gly Gly Gly Ser Phe Trp
    210                 215                 220

Val Leu Val Val Gly Gly Val Leu Ala Cys Tyr Ser Leu Leu Val
225                 230                 235                 240

Thr Val Ala Phe Ile Ile Phe Trp Val Arg Ser Lys Arg Ser Arg Leu
                245                 250                 255

Leu His Ser Asp Tyr Met Asn Met Thr Pro Arg Arg Pro Gly Pro Thr
            260                 265                 270

Arg Lys His Tyr Gln Pro Tyr Ala Pro Pro Arg Asp Phe Ala Ala Tyr
        275                 280                 285

Arg Ser Arg Val Lys Phe Ser Arg Ser Ala Asp Ala Pro Ala Tyr Gln
    290                 295                 300

Gln Gly Gln Asn Gln Leu Tyr Asn Glu Leu Asn Leu Gly Arg Arg Glu
305                 310                 315                 320

Glu Tyr Asp Val Leu Asp Lys Arg Arg Gly Arg Asp Pro Glu Met Gly
                325                 330                 335

Gly Lys Pro Arg Arg Lys Asn Pro Gln Glu Gly Leu Tyr Asn Glu Leu
            340                 345                 350

Gln Lys Asp Lys Met Ala Glu Ala Tyr Ser Glu Ile Gly Met Lys Gly
        355                 360                 365

Glu Arg Arg Arg Gly Lys Gly His Asp Gly Leu Tyr Gln Gly Leu Ser
    370                 375                 380

Thr Ala Thr Lys Asp Thr Tyr Asp Ala Leu His Met Gln Ala Leu Pro
385                 390                 395                 400

Pro Arg

<210> SEQ ID NO 42
<211> LENGTH: 217
<212> TYPE: PRT
<213> ORGANISM: Artificial sequence
<220> FEATURE:
<223> OTHER INFORMATION: Anti-CD20-(GA101)-crossFab VL-CH1 heavy chain

<400> SEQUENCE: 42

Asp Ile Val Met Thr Gln Thr Pro Leu Ser Leu Pro Val Thr Pro Gly
 1               5                  10                  15

Glu Pro Ala Ser Ile Ser Cys Arg Ser Ser Lys Ser Leu Leu His Ser
```

```
            20                  25                  30
Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys
    210                 215

<210> SEQ ID NO 43
<211> LENGTH: 226
<212> TYPE: PRT
<213> ORGANISM: Artificial sequence
<220> FEATURE:
<223> OTHER INFORMATION: Anti-CD20-(GA101)-crossFab VH-CL light chain

<400> SEQUENCE: 43

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser Ala Ser Val Ala Ala Pro Ser Val Phe
        115                 120                 125

Ile Phe Pro Pro Ser Asp Glu Gln Leu Lys Ser Gly Thr Ala Ser Val
    130                 135                 140

Val Cys Leu Leu Asn Asn Phe Tyr Pro Arg Glu Ala Lys Val Gln Trp
145                 150                 155                 160

Lys Val Asp Asn Ala Leu Gln Ser Gly Asn Ser Gln Glu Ser Val Thr
```

```
                    165                 170                 175
Glu Gln Asp Ser Lys Asp Ser Thr Tyr Ser Leu Ser Ser Thr Leu Thr
                180                 185                 190

Leu Ser Lys Ala Asp Tyr Glu Lys His Lys Val Tyr Ala Cys Glu Val
            195                 200                 205

Thr His Gln Gly Leu Ser Ser Pro Val Thr Lys Ser Phe Asn Arg Gly
        210                 215                 220

Glu Cys
225

<210> SEQ ID NO 44
<211> LENGTH: 107
<212> TYPE: PRT
<213> ORGANISM: Artificial sequence
<220> FEATURE:
<223> OTHER INFORMATION: crossFab CL

<400> SEQUENCE: 44

Ala Ser Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 45
<211> LENGTH: 105
<212> TYPE: PRT
<213> ORGANISM: Artificial sequence
<220> FEATURE:
<223> OTHER INFORMATION: crossFab CH1

<400> SEQUENCE: 45

Ser Ser Ala Ser Thr Lys Gly Pro Ser Val Phe Pro Leu Ala Pro Ser
1               5                   10                  15

Ser Lys Ser Thr Ser Gly Gly Thr Ala Ala Leu Gly Cys Leu Val Lys
            20                  25                  30

Asp Tyr Phe Pro Glu Pro Val Thr Val Ser Trp Asn Ser Gly Ala Leu
        35                  40                  45

Thr Ser Gly Val His Thr Phe Pro Ala Val Leu Gln Ser Ser Gly Leu
    50                  55                  60

Tyr Ser Leu Ser Ser Val Val Thr Val Pro Ser Ser Ser Leu Gly Thr
65                  70                  75                  80

Gln Thr Tyr Ile Cys Asn Val Asn His Lys Pro Ser Asn Thr Lys Val
                85                  90                  95

Asp Lys Lys Val Glu Pro Lys Ser Cys
            100                 105

<210> SEQ ID NO 46
<211> LENGTH: 2664
```

```
<212> TYPE: DNA
<213> ORGANISM: Artificial sequence
<220> FEATURE:
<223> OTHER INFORMATION: Anti-CD20-(GA101)-crossFabVH-CL CD28ATD-
      CD28CSD-CD3zSSD pETR17098

<400> SEQUENCE: 46
atgggatgga gctgtatcat cctcttcttg gtagcaacag ctaccggtgt gcattcccag      60
gtgcaattgg tgcagtctgg cgctgaagtt aagaagcctg ggagttcagt gaaggtctcc     120
tgcaaggctt ccggatacgc cttcagctat tcttggatca attgggtgcg gcaggcgcct     180
ggacaagggc tcgagtggat gggacggatc tttcccggcg atgggggatac tgactacaat     240
gggaaattca agggcagagt cacaattacc gccgacaaat ccactagcac agcctatatg     300
gagctgagca gcctgagatc tgaggacacg gccgtgtatt actgtgcaag aaatgtcttt     360
gatggttact ggcttgttta ctggggccag ggaaccctgg tcaccgtctc ctcagctagc     420
gtggccgctc cctccgtgtt catcttccca ccttccgacg agcagctgaa gtccggcacc     480
gcttctgtcg tgtgcctgct gaacaacttc taccccccgcg aggccaaggt gcagtggaag     540
gtggacaacg ccctgcagtc cggcaacagc aggaatccg tgaccgagca ggactccaag     600
gacagcacct actccctgtc ctccaccctg accctgtcca aggccgacta cgagaagcac     660
aaggtgtacg cctgcgaagt gacccaccag ggcctgtcta gcccgtgac caagtctttc     720
aaccggggcg agtgctgata aggaattccc cgaagtaact tagaagctgt aaatcaacga     780
tcaatagcag gtgtggcaca ccagtcatac cttgatcaag cacttctgtt tccccggact     840
gagtatcaat aggctgctcg cgcggctgaa ggagaaaacg ttcgttaccc gaccaactac     900
ttcgagaagc ttagtaccac catgaacgag gcagggtgtt tcgctcagca acccccagt     960
gtagatcagg ctgatgagtc actgcaaccc ccatgggcga ccatggcagt ggctgcgttg    1020
gcggcctgcc catggagaaa tccatgggac gctctaattc tgacatggtg tgaagtgcct    1080
attgagctaa ctggtagtcc tccggcccct gattgcggct aatcctaact gcggagcaca    1140
tgctcacaaa ccagtgggtg gtgtgtcgta acgggcaact ctgcagcgga accgactact    1200
ttgggtgtcc gtgtttcctt ttattcctat attggctgct tatggtgaca atcaaaaagt    1260
tgttaccata tagctattgg attggccatc cggtgtgcaa cagggcaact gtttacctat    1320
ttattggttt tgtaccatta tcactgaagt ctgtgatcac tctcaaattc attttgaccc    1380
tcaacacaat caaacgccac catgggatgg agctgtatca tcctcttctt ggtagcaaca    1440
gctaccggtg tgcactccga catcgtgatg acccagactc cactctccct gcccgtcacc    1500
cctggagagc ccgccagcat tagctgcagg tctagcaaga gcctcttgca cagcaatggc    1560
atcacttatt tgtattggta cctgcaaaag ccagggcagt ctccacagct cctgatttat    1620
caaatgtcca accttgtctc tggcgtccct gatcggttct ccggttccgg tcaggcact    1680
gatttcacac tgaaaatcag cagggtggag gctgaggatg ttggagttta ttactgcgct    1740
cagaatctag aacttcctta caccttcggc ggagggacca aggtggagat caaatccagc    1800
gctagcacca agggcccctc cgtgttcccc ctggccccca gcagcaagag caccagcggc    1860
ggcacagccg ctctgggctg cctggtcaag gactacttcc ccgagcccgt gaccgtgtcc    1920
tggaacagcg gagccctgac ctccggcgtg cacaccttcc ccgccgtgct gcagagttct    1980
ggcctgtata gcctgagcag cgtggtcacc gtgccttcta gcagcctggg cacccagacc    2040
tacatctgca acgtgaacca caagcccagc aacaccaagg tggacaagaa ggtggagccc    2100
aagagctgcg gaggggggcgg atccttctgg gtgctggtgg tggtgggcgg cgtgctggcc    2160
```

```
tgctacagcc tgctggtgac cgtggccttc atcatcttct gggtgaggag caagaggagc    2220
aggctgctgc acagcgacta catgaacatg accccaggag ggcccggccc caccaggaag    2280
cactaccagc cctacgcccc ccccagggac ttcgccgcct acaggagcag ggtgaagttc    2340
agcaggagcg ccgacgcccc cgcctaccag cagggccaga accagctgta taacgagctg    2400
aacctgggca ggagggagga gtacgacgtg ctggacaaga ggaggggcag ggaccccgag    2460
atgggcggca agcccaggag gaagaacccc caggagggcc tgtataacga gctgcagaag    2520
gacaagatgg ccgaggccta cagcgagatc ggcatgaagg gcgagaggag gaggggcaag    2580
ggccacgacg gcctgtacca gggcctgagc accgccacca aggacaccta cgacgccctg    2640
cacatgcagg ccctgccccc cagg                                           2664

<210> SEQ ID NO 47
<211> LENGTH: 324
<212> TYPE: DNA
<213> ORGANISM: Artificial sequence
<220> FEATURE:
<223> OTHER INFORMATION: crossFab CL

<400> SEQUENCE: 47
gctagcgtgg ccgctccctc cgtgttcatc ttcccacctt ccgacgagca gctgaagtcc     60
ggcaccgctt ctgtcgtgtg cctgctgaac aacttctacc ccgcgaggc caaggtgcag    120 tggaaggtgg acaacgccct gcagtccggc aacagccagg aatccgtgac cgagcaggac    180
tccaaggaca gcacctactc cctgtcctcc accctgaccc tgtccaaggc cgactacgag    240
aagcacaagg tgtacgcctg cgaagtgacc caccagggcc tgtctagccc cgtgaccaag    300
tctttcaacc ggggcgagtg ctga                                           324

<210> SEQ ID NO 48
<211> LENGTH: 315
<212> TYPE: DNA
<213> ORGANISM: Artificial sequence
<220> FEATURE:
<223> OTHER INFORMATION: crossFab CH1

<400> SEQUENCE: 48
tccagcgcta gcaccaaggg ccctccgtg ttcccctgg ccccagcag caagagcacc        60 agcggcggca cagccgctct gggctgcctg gtcaaggact acttccccga gcccgtgacc    120
gtgtcctgga cagcggagc cctgacctcc ggcgtgcaca ccttcccgc cgtgctgcag      180 agttctggc tgtatagcct gagcagcgtg gtcaccgtgc cttctagcag cctgggcacc    240
cagacctaca tctgcaacgt gaaccacaag cccagcaaca ccaaggtgga caagaaggtg    300
gagcccaaga gctgc                                                     315

<210> SEQ ID NO 49
<211> LENGTH: 3444
<212> TYPE: DNA
<213> ORGANISM: Artificial sequence
<220> FEATURE:
<223> OTHER INFORMATION: Anti-CD20-(GA101)-crossFabVH-CL CD28ATD-
      CD28CSD-CD3zSSD-eGFP pETR17098

<400> SEQUENCE: 49
atgggatgga gctgtatcat cctcttcttg gtagcaacag ctaccggtgt gcattcccag     60
gtgcaattgg tgcagtctgg cgctgaagtt aagaagcctg ggagttcagt gaaggtctcc    120
tgcaaggctt ccggatacgc cttcagctat tcttggatca attgggtgcg gcaggcgcct    180
```

```
ggacaagggc tcgagtggat gggacggatc tttcccggcg atggggatac tgactacaat    240
gggaaattca agggcagagt cacaattacc gccgacaaat ccactagcac agcctatatg    300
gagctgagca gcctgagatc tgaggacacg ccgtgtatt actgtgcaag aaatgtcttt    360
gatggttact ggcttgttta ctggggccag ggaaccctgg tcaccgtctc ctcagctagc    420
gtggccgctc cctccgtgtt catcttccca ccttccgacg agcagctgaa gtccggcacc    480
gcttctgtcg tgtgcctgct gaacaacttc taccccgcg aggccaaggt gcagtggaag    540
gtggacaacg ccctgcagtc cggcaacagc caggaatccg tgaccgagca ggactccaag    600
gacagcacct actccctgtc ctccaccctg accctgtcca aggccgacta cgagaagcac    660
aaggtgtacg cctgcgaagt gacccaccag ggcctgtcta gccccgtgac caagtctttc    720
aaccggggcg agtgctgata aggaattccc cgaagtaact tagaagctgt aaatcaacga    780
tcaatagcag gtgtggcaca ccagtcatac cttgatcaag cacttctgtt tccccggact    840
gagtatcaat aggctgctcg cgcggctgaa ggagaaaacg ttcgttaccc gaccaactac    900
ttcgagaagc ttagtaccac catgaacgag gcagggtgtt tcgctcagca caaccccagt    960
gtagatcagg ctgatgagtc actgcaaccc ccatgggcga ccatggcagt ggctgcgttg   1020
gcggcctgcc catggagaaa tccatgggac gctctaattc tgacatggtg tgaagtgcct   1080
attgagctaa ctggtagtcc tccggcccct gattgcggct aatcctaact gcggagcaca   1140
tgctcacaaa ccagtgggtg gtgtgtcgta acggcaact ctgcagcgga accgactact   1200
ttgggtgtcc gtgtttcctt ttattccat attggctgct tatggtgaca atcaaaaagt   1260
tgttaccata tagctattgg attggccatc cggtgtgcaa cagggcaact gtttacctat   1320
ttattggttt tgtaccatta tcactgaagt ctgtgatcac tctcaaattc attttgaccc   1380
tcaacacaat caaacgccac catgggatgg agctgtatca tcctcttctt ggtagcaaca   1440
gctaccggtg tgcactccga catcgtgatg acccagactc cactctccct gcccgtcacc   1500
cctggagagc ccgccagcat tagctgcagg tctagcaaga gcctcttgca cagcaatggc   1560
atcacttatt tgtattggta cctgcaaaag ccagggcagt ctccacagct cctgatttat   1620
caaatgtcca accttgtctc tggcgtccct gatcggttct ccggttccgg tcaggcact   1680 gatttcacac tgaaaatcag cagggtggag gctgaggatg ttggagttta ttactgcgct   1740
cagaatctag aacttcctta caccttcggc ggagggacca aggtggagat caaatccagc   1800
gctagcacca agggcccctc cgtgttcccc ctggcccca gcagcaagag caccagcggc   1860
ggcacagccg ctctgggctg cctggtcaag gactacttcc ccgagcccgt gaccgtgtcc   1920
tggaacagcg gagccctgac ctccggcgtg cacaccttcc ccgccgtgct gcagagttct   1980
ggcctgtata gcctgagcag cgtggtcacc gtgccttcta gcagcctggg cacccagacc   2040
tacatctgca acgtgaacca caagcccagc aacaccaagg tggacaagaa ggtggagccc   2100
aagagctgcg aggggggcgg atccttctgg gtgctggtgg tggtgggcgg cgtgctggcc   2160
tgctacagcc tgctggtgac cgtggccttc atcatcttct gggtgaggag caagaggagc   2220
aggctgctgc acagcgacta catgaacatg acccccagga ggcccggccc caccaggaag   2280
cactaccagc cctacgcccc ccccagggac ttcgccgcct acaggagcag ggtgaagttc   2340
agcaggagcg ccgacgcccc cgcctaccag cagggccaga accagctgta taacgagctg   2400
aacctgggca ggagggagga gtacgacgtg ctggacaaga gggggggcag ggaccccgag   2460
atgggcggca agcccaggag gaagaacccc caggagggcc tgtataacga gctgcagaag   2520
```

-continued

```
gacaagatgg ccgaggccta cagcgagatc ggcatgaagg gcgagaggag gaggggcaag      2580
ggccacgacg gcctgtacca gggcctgagc accgccacca aggacaccta cgacgccctg      2640
cacatgcagg ccctgccccc caggtccgga gagggcagag gaagtcttct aacatgcggt      2700
gacgtggagg agaatcccgg ccctagggtg agcaagggcg aggagctgtt caccggggtg      2760
gtgcccatcc tggtcgagct ggacggcgac gtaaacggcc acaagttcag cgtgtccggc      2820
gagggcgagg gcgatgccac ctacggcaag ctgaccctga agttcatctg caccaccggc      2880
aagctgcccg tgccctggcc caccctcgtg accaccctga cctacggcgt gcagtgcttc      2940
agccgctacc ccgaccacat gaagcagcac gacttcttca gtccgccat gcccgaaggc       3000 tacgtccagg agcgcaccat cttcttcaag gacgacggca actacaagac ccgcgccgag      3060
gtgaagttcg agggcgacac cctggtgaac cgcatcgagc tgaagggcat cgacttcaag      3120
gaggacggca acatcctggg gcacaagctg gagtacaact acaacagcca caacgtctat      3180
atcatggccg acaagcagaa gaacggcatc aaggtgaact tcaagatccg ccacaacatc      3240
gaggacggca gcgtgcagct cgccgaccac taccagcaga cacccccat cggcgacggc       3300 cccgtgctgc tgcccgacaa ccactacctg agcacccagt ccgccctgag caaagacccc      3360
aacgagaagc gcgatcacat ggtcctgctg gagttcgtga ccgccgccgg gatcactctc      3420
ggcatggacg agctgtacaa gtga                                             3444
```

```
<210> SEQ ID NO 50
<211> LENGTH: 404
<212> TYPE: PRT
<213> ORGANISM: Artificial sequence
<220> FEATURE:
<223> OTHER INFORMATION: Anti-CD20-(GA101)-Fab VL-CL light chain-
      CD28ATD-CD28CSD-CD3zSSD fusion

<400> SEQUENCE: 50
```

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190
```

-continued

```
Lys His Lys Val Tyr Ala Cys Glu Val Thr His Gln Gly Leu Ser Ser
            195                 200                 205

Pro Val Thr Lys Ser Phe Asn Arg Gly Glu Cys Gly Gly Gly Gly Ser
        210                 215                 220

Phe Trp Val Leu Val Val Gly Gly Val Leu Ala Cys Tyr Ser Leu
225                 230                 235                 240

Leu Val Thr Val Ala Phe Ile Ile Phe Trp Val Arg Ser Lys Arg Ser
                245                 250                 255

Arg Leu Leu His Ser Asp Tyr Met Asn Met Thr Pro Arg Arg Pro Gly
            260                 265                 270

Pro Thr Arg Lys His Tyr Gln Pro Tyr Ala Pro Pro Arg Asp Phe Ala
        275                 280                 285

Ala Tyr Arg Ser Arg Val Lys Phe Ser Arg Ser Ala Asp Ala Pro Ala
    290                 295                 300

Tyr Gln Gln Gly Gln Asn Gln Leu Tyr Asn Glu Leu Asn Leu Gly Arg
305                 310                 315                 320

Arg Glu Glu Tyr Asp Val Leu Asp Lys Arg Arg Gly Arg Asp Pro Glu
                325                 330                 335

Met Gly Gly Lys Pro Arg Arg Lys Asn Pro Gln Glu Gly Leu Tyr Asn
            340                 345                 350

Glu Leu Gln Lys Asp Lys Met Ala Glu Ala Tyr Ser Glu Ile Gly Met
        355                 360                 365

Lys Gly Glu Arg Arg Arg Gly Lys Gly His Asp Gly Leu Tyr Gln Gly
    370                 375                 380

Leu Ser Thr Ala Thr Lys Asp Thr Tyr Asp Ala Leu His Met Gln Ala
385                 390                 395                 400

Leu Pro Pro Arg

<210> SEQ ID NO 51
<211> LENGTH: 658
<212> TYPE: PRT
<213> ORGANISM: Artificial sequence
<220> FEATURE:
<223> OTHER INFORMATION: Anti-CD20-(GA101)-scFab-CD28ATD-CD28CSD-CD3zSSD
      fusion pETR17101

<400> SEQUENCE: 51

Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140
```

```
Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
        180                 185                 190

Lys His Lys Val Tyr Ala Cys Glu Val Thr His Gln Gly Leu Ser Ser
    195                 200                 205

Pro Val Thr Lys Ser Phe Asn Arg Gly Glu Cys Gly Gly Gly Gly Ser
210                 215                 220

Gly Gly Gly Gly Ser Gly Gly Gly Ser Gly Gly Gly Gly Ser Gly
225                 230                 235                 240

Gly Gly Gly Ser Gly Gly Gly Ser Gly Gly Gln Val Gln Leu Val
            245                 250                 255

Gln Ser Gly Ala Glu Val Lys Lys Pro Gly Ser Ser Val Lys Val Ser
        260                 265                 270

Cys Lys Ala Ser Gly Tyr Ala Phe Ser Tyr Ser Trp Ile Asn Trp Val
    275                 280                 285

Arg Gln Ala Pro Gly Gln Gly Leu Glu Trp Met Gly Arg Ile Phe Pro
290                 295                 300

Gly Asp Gly Asp Thr Asp Tyr Asn Gly Lys Phe Lys Gly Arg Val Thr
305                 310                 315                 320

Ile Thr Ala Asp Lys Ser Thr Ser Thr Ala Tyr Met Glu Leu Ser Ser
            325                 330                 335

Leu Arg Ser Glu Asp Thr Ala Val Tyr Tyr Cys Ala Arg Asn Val Phe
        340                 345                 350

Asp Gly Tyr Trp Leu Val Tyr Trp Gly Gln Gly Thr Leu Val Thr Val
    355                 360                 365

Ser Ser Ala Ser Thr Lys Gly Pro Ser Val Phe Pro Leu Ala Pro Ser
370                 375                 380

Ser Lys Ser Thr Ser Gly Gly Thr Ala Ala Leu Gly Cys Leu Val Lys
385                 390                 395                 400

Asp Tyr Phe Pro Glu Pro Val Thr Val Ser Trp Asn Ser Gly Ala Leu
            405                 410                 415

Thr Ser Gly Val His Thr Phe Pro Ala Val Leu Gln Ser Ser Gly Leu
        420                 425                 430

Tyr Ser Leu Ser Ser Val Val Thr Val Pro Ser Ser Ser Leu Gly Thr
    435                 440                 445

Gln Thr Tyr Ile Cys Asn Val Asn His Lys Pro Ser Asn Thr Lys Val
450                 455                 460

Asp Lys Lys Val Glu Pro Lys Ser Cys Gly Gly Gly Ser Phe Trp
465                 470                 475                 480

Val Leu Val Val Val Gly Gly Val Leu Ala Cys Tyr Ser Leu Leu Val
            485                 490                 495

Thr Val Ala Phe Ile Ile Phe Trp Val Arg Ser Lys Arg Ser Arg Leu
        500                 505                 510

Leu His Ser Asp Tyr Met Asn Met Thr Pro Arg Arg Pro Gly Pro Thr
    515                 520                 525

Arg Lys His Tyr Gln Pro Tyr Ala Pro Pro Arg Asp Phe Ala Ala Tyr
530                 535                 540

Arg Ser Arg Val Lys Phe Ser Arg Ser Ala Asp Ala Pro Ala Tyr Gln
545                 550                 555                 560

Gln Gly Gln Asn Gln Leu Tyr Asn Glu Leu Asn Leu Gly Arg Arg Glu
```

```
                    565                 570                 575
Glu Tyr Asp Val Leu Asp Lys Arg Arg Gly Arg Asp Pro Glu Met Gly
                580                 585                 590

Gly Lys Pro Arg Arg Lys Asn Pro Gln Glu Gly Leu Tyr Asn Glu Leu
            595                 600                 605

Gln Lys Asp Lys Met Ala Glu Ala Tyr Ser Glu Ile Gly Met Lys Gly
        610                 615                 620

Glu Arg Arg Arg Gly Lys Gly His Asp Gly Leu Tyr Gln Gly Leu Ser
625                 630                 635                 640

Thr Ala Thr Lys Asp Thr Tyr Asp Ala Leu His Met Gln Ala Leu Pro
                645                 650                 655

Pro Arg

<210> SEQ ID NO 52
<211> LENGTH: 473
<212> TYPE: PRT
<213> ORGANISM: Artificial sequence
<220> FEATURE:
<223> OTHER INFORMATION: Anti-CD20-(GA101)-scFab

<400> SEQUENCE: 52

Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Gly Gly Gly Gly Ser
    210                 215                 220

Gly Gly Gly Gly Ser Gly Gly Gly Ser Gly Gly Gly Gly Ser Gly
225                 230                 235                 240

Gly Gly Gly Ser Gly Gly Gly Ser Gly Gly Gln Val Gln Leu Val
                245                 250                 255

Gln Ser Gly Ala Glu Val Lys Lys Pro Gly Ser Ser Val Lys Val Ser
            260                 265                 270
```

```
Cys Lys Ala Ser Gly Tyr Ala Phe Ser Tyr Ser Trp Ile Asn Trp Val
        275                 280                 285

Arg Gln Ala Pro Gly Gln Gly Leu Glu Trp Met Gly Arg Ile Phe Pro
    290                 295                 300

Gly Asp Gly Asp Thr Asp Tyr Asn Gly Lys Phe Lys Gly Arg Val Thr
305                 310                 315                 320

Ile Thr Ala Asp Lys Ser Thr Ser Thr Ala Tyr Met Glu Leu Ser Ser
                325                 330                 335

Leu Arg Ser Glu Asp Thr Ala Val Tyr Tyr Cys Ala Arg Asn Val Phe
            340                 345                 350

Asp Gly Tyr Trp Leu Val Tyr Trp Gly Gln Gly Thr Leu Val Thr Val
        355                 360                 365

Ser Ser Ala Ser Thr Lys Gly Pro Ser Val Phe Pro Leu Ala Pro Ser
    370                 375                 380

Ser Lys Ser Thr Ser Gly Gly Thr Ala Ala Leu Gly Cys Leu Val Lys
385                 390                 395                 400

Asp Tyr Phe Pro Glu Pro Val Thr Val Ser Trp Asn Ser Gly Ala Leu
                405                 410                 415

Thr Ser Gly Val His Thr Phe Pro Ala Val Leu Gln Ser Ser Gly Leu
            420                 425                 430

Tyr Ser Leu Ser Ser Val Val Thr Val Pro Ser Ser Ser Leu Gly Thr
        435                 440                 445

Gln Thr Tyr Ile Cys Asn Val Asn His Lys Pro Ser Asn Thr Lys Val
    450                 455                 460

Asp Lys Lys Val Glu Pro Lys Ser Cys
465                 470

<210> SEQ ID NO 53
<211> LENGTH: 106
<212> TYPE: PRT
<213> ORGANISM: Artificial sequence
<220> FEATURE:
<223> OTHER INFORMATION: scFab-CL

<400> SEQUENCE: 53

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu
            100                 105

<210> SEQ ID NO 54
<211> LENGTH: 32
<212> TYPE: PRT
<213> ORGANISM: Artificial sequence
<220> FEATURE:
<223> OTHER INFORMATION: (G4S)6G2 linker
```

<400> SEQUENCE: 54

Gly Gly Gly Gly Ser Gly Gly Gly Ser Gly Gly Gly Ser Gly
1               5                   10                  15

Gly Gly Gly Ser Gly Gly Gly Ser Gly Gly Gly Ser Gly Gly
                20                  25                  30

<210> SEQ ID NO 55
<211> LENGTH: 2031
<212> TYPE: DNA
<213> ORGANISM: Artificial sequence
<220> FEATURE:
<223> OTHER INFORMATION: Anti-CD20-(GA101)-scFab-CD28ATD-CD28CSD-CD3zSSD
      fusion pETR170101

<400> SEQUENCE: 55

| | | | |
|---|---|---|---|
| atgggatgga | gctgtatcat | cctcttcttg gtagcaacag | ctacgggtgt gcattccgac | 60 |
| atcgtgatga | cccagactcc | actctccctg cccgtcaccc | ctggagagcc cgccagcatt | 120 |
| agctgcaggt | ctagcaagag | cctcttgcac agcaatggca | tcacttattt gtattggtac | 180 |
| ctgcaaaagc | cagggcagtc | tccacagctc ctgatttatc | aaatgtccaa ccttgtctct | 240 |
| ggcgtccctg | atcggttctc | cggttccggg tcaggcactg | atttcacact gaaaatcagc | 300 |
| agggtggagg | ctgaggatgt | tggagtttat tactgcgctc | agaatctaga acttccttac | 360 |
| accttcggcg | agggaccaa | ggtggagatc aaacgtacgg | tggctgcacc atctgtcttc | 420 |
| atcttcccgc | catctgatga | gcagttgaaa tctggaactg | cctctgttgt gtgcctgctg | 480 |
| aataacttct | atcccagaga | ggccaaagta cagtggaagg | tggataacgc cctccaatcg | 540 |
| ggtaactccc | aggagagtgt | cacagagcag gacagcaagg | acagcaccta cagcctcagc | 600 |
| agcaccctga | cgctgagcaa | agcagactac gagaaacaca | agtctacgc ctgcgaagtc | 660 |
| acccatcagg | gcctgagctc | gcccgtcaca aagagcttca | cagggagaga gtgtggcggc | 720 |
| ggaggatctg | gtggcggagg | tagtggtggt ggtggatctg | gcggaggcgg ctccggcgga | 780 |
| ggtggaagcg | gaggtggtgg | ttccggagga caggtgcaat | tggtgcagtc tggcgctgaa | 840 |
| gttaagaagc | ctgggagttc | agtgaaggtc tcctgcaagg | cttcgggata cgccttcagc | 900 |
| tattcttgga | tcaattgggt | gcggcaggcg cctggacaag | gctcgagtg gatgggacgg | 960 |
| atctttcccg | gcgatgggga | tactgactac aatgggaaat | tcaagggcag agtcacaatt | 1020 |
| accgccgaca | aatccactag | cacagcctat atggagctga | gcagcctgag atctgaggac | 1080 |
| acggccgtgt | attactgtgc | aagaaatgtc tttgatggtt | actggcttgt ttactggggc | 1140 |
| cagggaaccc | tggtcaccgt | ctcctcagct agcaccaagg | gcccctccgt gttccccctg | 1200 |
| gccccagca | gcaagagcac | cagcggcggc acagccgctc | tgggctgcct ggtcaaggac | 1260 |
| tacttccccg | agcccgtgac | cgtgtcctgg aacagcggag | ccctgacctc cggcgtgcac | 1320 |
| accttccccg | ccgtgctgca | gagttctggc ctgtatagcc | tgagcagcgt ggtcaccgtg | 1380 |
| ccttctagca | gcctgggcac | ccagacctac atctgcaacg | tgaaccacaa gcccagcaac | 1440 |
| accaaggtgg | acaagaaggt | ggagcccaag agctgcggag | gggcggatc cttctgggtg | 1500 |
| ctggtggtgg | tgggcggcgt | gctggcctgc tacagcctgc | tggtgaccgt ggccttcatc | 1560 |
| atcttctggg | tgaggagcaa | gaggagcagg ctgctgcaca | gcgactacat gaacatgacc | 1620 |
| cccaggaggc | ccggccccac | caggaagcac taccagccct | acgcccccc cagggacttc | 1680 |
| gccgcctaca | ggagcagggt | gaagttcagc aggagcgccg | acgcccccgc ctaccagcag | 1740 |
| ggccagaacc | agctgtataa | cgagctgaac ctgggcagga | gggaggagta cgacgtgctg | 1800 |

```
gacaagagga ggggcaggga ccccgagatg ggcggcaagc ccaggaggaa gaaccccccag   1860 gagggcctgt ataacgagct gcagaaggac aagatggccg aggcctacag cgagatcggc   1920
atgaagggcg agaggaggag gggcaagggc cacgacggcc tgtaccaggg cctgagcacc   1980
gccaccaagg acacctacga cgccctgcac atgcaggccc tgccccccag g            2031

<210> SEQ ID NO 56
<211> LENGTH: 336
<212> TYPE: DNA
<213> ORGANISM: Artificial sequence
<220> FEATURE:
<223> OTHER INFORMATION: scFab-VL

<400> SEQUENCE: 56
gacatcgtga tgacccagac tccactctcc ctgcccgtca cccctggaga gcccgccagc    60
attagctgca ggtctagcaa gagcctcttg cacagcaatg gcatcactta tttgtattgg   120
tacctgcaaa agccagggca gtctccacag ctcctgattt atcaaatgtc aaccttgtc    180 tctggcgtcc ctgatcggtt ctccggttcc gggtcaggca ctgatttcac actgaaaatc   240
agcagggtgg aggctgagga tgttggagtt tattactgcg ctcagaatct agaacttcct   300 tacacccttcg gcggagggac caaggtggag atcaaa                            336

<210> SEQ ID NO 57
<211> LENGTH: 321
<212> TYPE: DNA
<213> ORGANISM: Artificial sequence
<220> FEATURE:
<223> OTHER INFORMATION: scFab-CL

<400> SEQUENCE: 57
cgtacggtgg ctgcaccatc tgtcttcatc ttcccgccat ctgatgagca gttgaaatct    60
ggaactgcct ctgttgtgtg cctgctgaat aacttctatc ccagagaggc caaagtacag   120
tggaaggtgg ataacgccct ccaatcgggt aactcccagg agagtgtcac agagcaggac   180
agcaaggaca gcacctacag cctcagcagc accctgacgc tgagcaaagc agactacgag   240
aaacacaaag tctacgcctg cgaagtcacc catcagggcc tgagctcgcc cgtcacaaag   300
agcttcaaca ggggagagtg t                                             321

<210> SEQ ID NO 58
<211> LENGTH: 357
<212> TYPE: DNA
<213> ORGANISM: Artificial sequence
<220> FEATURE:
<223> OTHER INFORMATION: Anti-CD20-(GA101)- scFab-VH

<400> SEQUENCE: 58
caggtgcaat ggtgcagtc tggcgctgaa gttaagaagc ctgggagttc agtgaaggtc     60
tcctgcaagg cttcgggata cgccttcagc tattcttgga tcaattgggt gcggcaggcg   120
cctggacaag gctcgagtg gatgggacgg atctttcccg gcgatgggga tactgactac    180
aatgggaaat tcaagggcag agtcacaatt accgccgaca aatccactag cacagcctat   240
atggagctga gcagcctgag atctgaggac acggccgtgt attactgtgc aagaaatgtc   300
tttgatggtt actggcttgt ttactgggggc cagggaaccc tggtcaccgt ctcctca     357

<210> SEQ ID NO 59
<211> LENGTH: 2806
<212> TYPE: DNA
<213> ORGANISM: Artificial sequence
```

<220> FEATURE:
<223> OTHER INFORMATION: Anti-CD20-(GA101)-scFab-CD28ATD-CD28CSD-
CD3zSSD-eGFP fusion pETR170101

<400> SEQUENCE: 59

| | | |
|---|---|---|
| atggagctgt atcatcctct tcttggtagc aacagctacg ggtgtgcatt ccgacatcgt | 60 |
| gatgacccag actccactct ccctgcccgt caccctggga gagcccgcca gcattagctg | 120 |
| caggtctagc aagagcctct tgcacagcaa tggcatcact tatttgtatt ggtacctgca | 180 |
| aaagccaggg cagtctccac agctcctgat ttatcaaatg tccaaccttg tctctggcgt | 240 |
| ccctgatcgg ttctccggtt ccgggtcagg cactgatttc acactgaaaa tcagcagggt | 300 |
| ggaggctgag gatgttggag tttattactg cgctcagaat ctagaacttc cttacacctt | 360 |
| cggcggaggg accaaggtgg agatcaaacg tacggtggct gcaccatctg tcttcatctt | 420 |
| cccgccatct gatgagcagt tgaaatctgg aactgcctct gttgtgtgcc tgctgaataa | 480 |
| cttctatccc agagaggcca agtacagtg aaggtggat aacgccctcc aatcgggtaa | 540 |
| ctcccaggag agtgtcacag agcaggacag caaggacagc acctacagcc tcagcagcac | 600 |
| cctgacgctg agcaaagcag actacgagaa acacaaagtc tacgcctgcg aagtcaccca | 660 |
| tcagggcctg agctcgcccg tcacaaagag cttcaacagg ggagagtgtg gcggcggagg | 720 |
| atctggtggc ggaggtagtg gtggtggtgg atcggcgga gcggctccg gcggaggtgg | 780 |
| aagcggaggt ggtggttccg gaggacaggt gcaattggtg cagtctggcg ctgaagttaa | 840 |
| gaagcctggg agttcagtga aggtctcctg caaggcttcg ggatacgcct tcagctattc | 900 |
| ttggatcaat tgggtgcggc aggcgcctgg acaaggctc gagtggatgg gacggatctt | 960 |
| tcccggcgat ggggatactg actacaatgg gaaattcaag ggcagagtca caattaccgc | 1020 |
| cgacaaatcc actagcacag cctatatgga gctgagcagc tgagatctg aggacacggc | 1080 |
| cgtgtattac tgtgcaagaa atgtctttga tggttactgg cttgtttact ggggccaggg | 1140 |
| aaccctggtc accgtctcct cagctagcac caagggcccc tccgtgttcc cctggcccc | 1200 |
| cagcagcaag agcaccagcg gcggcacagc cgctctgggc tgcctggtca aggactactt | 1260 |
| ccccgagccc gtgaccgtgt cctggaacag cggagccctg acctccggcg tgcacacctt | 1320 |
| ccccgccgtg ctgcagagtt ctggcctgta gcctgagc agcgtggtca ccgtgccttc | 1380 |
| tagcagcctg gcacccaga cctacatctg aacgtgaac cacaagccca gcaacaccaa | 1440 |
| ggtggacaag aagtggagc caagagctg cggaggggc ggatccttct gggtgctggt | 1500 |
| ggtggtgggc ggcgtgctgg cctgctacag cctgctggtg accgtggcct tcatcatctt | 1560 |
| ctgggtgagg agcaagagga gcaggctgct gcacagcgac tacatgaaca tgaccccag | 1620 |
| gaggcccggc cccaccagga agcactacca gcccctacgcc cccccagggg acttcgccgc | 1680 |
| ctacaggagc agggtgaagt tcagcaggag cgccgacgcc cccgcctacc agcagggcca | 1740 |
| gaaccagctg tataacgagc tgaacctggg caggagggag gagtacgacg tgctggacaa | 1800 |
| gaggagggc agggaccccg agatgggcgg caagcccagg aggaagaacc cccaggaggg | 1860 |
| cctgtataac gagctgcaga aggacaagat ggccgaggcc tacagcgaga tcggcatgaa | 1920 |
| gggcgagagg aggagggca agggccacga cggcctgtac cagggcctga gcaccgccac | 1980 |
| caaggacacc tacgacgccc tgcacatgca ggccctgccc cccaggtccg agagggcag | 2040 |
| aggaagtctt ctaacatgcg gtgacgtgga ggagaatccc ggccctaggg tgagcaaggg | 2100 |
| cgaggagctg ttcaccgggg tggtgcccat cctggtcgag ctggacgcg acgtaaacgg | 2160 |
| ccacaagttc agcgtgtccg gcgaggggcga gggcgatgcc acctacggca agctgaccct | 2220 |

```
gaagttcatc tgcaccaccg gcaagctgcc cgtgccctgg cccacccctcg tgaccaccct    2280 gacctacggc gtgcagtgct tcagccgcta ccccgaccac atgaagcagc acgacttctt    2340
caagtccgcc atgcccgaag gctacgtcca ggagcgcacc atcttcttca aggacgacgg    2400
caactacaag acccgcgccg aggtgaagtt cgagggcgac accctggtga accgcatcga    2460
gctgaagggc atcgacttca aggaggacgg caacatcctg ggcacaagc tggagtacaa    2520 ctacaacagc cacaacgtct atatcatggc cgacaagcag aagaacggca tcaaggtgaa    2580
cttcaagatc cgccacaaca tcgaggacgg cagcgtgcag ctcgccgacc actaccagca    2640
gaacaccccc atcggcgacg gccccgtgct gctgcccgac aaccactacc tgagcaccca    2700
gtccgccctg agcaaagacc ccaacgagaa gcgcgatcac atggtcctgc tggagttcgt    2760
gaccgccgcc gggatcactc tcggcatgga cgagctgtac aagtga    2806
```

<210> SEQ ID NO 60
<211> LENGTH: 436
<212> TYPE: PRT
<213> ORGANISM: Artificial sequence
<220> FEATURE:
<223> OTHER INFORMATION: Anti-CD20-(GA101)-ds-scFv-CD28ATD-CD28CSD-
    CD3zSSD fusion pETR17162

<400> SEQUENCE: 60

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Cys Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Gly Gly Gly Gly Ser Asp Ile Val Met Thr
    130                 135                 140

Gln Thr Pro Leu Ser Leu Pro Val Thr Pro Gly Glu Pro Ala Ser Ile
145                 150                 155                 160

Ser Cys Arg Ser Ser Lys Ser Leu Leu His Ser Asn Gly Ile Thr Tyr
                165                 170                 175

Leu Tyr Trp Tyr Leu Gln Lys Pro Gly Gln Ser Pro Gln Leu Leu Ile
            180                 185                 190

Tyr Gln Met Ser Asn Leu Val Ser Gly Val Pro Asp Arg Phe Ser Gly
        195                 200                 205

Ser Gly Ser Gly Thr Asp Phe Thr Leu Lys Ile Ser Arg Val Glu Ala
    210                 215                 220

Glu Asp Val Gly Val Tyr Tyr Cys Ala Gln Asn Leu Glu Leu Pro Tyr
225                 230                 235                 240

Thr Phe Gly Cys Gly Thr Lys Val Glu Ile Lys Gly Gly Gly Gly Ser
                245                 250                 255
```

```
Phe Trp Val Leu Val Val Gly Gly Val Leu Ala Cys Tyr Ser Leu
                260                 265                 270

Leu Val Thr Val Ala Phe Ile Ile Phe Trp Val Arg Ser Lys Arg Ser
            275                 280                 285

Arg Leu Leu His Ser Asp Tyr Met Asn Met Thr Pro Arg Arg Pro Gly
        290                 295                 300

Pro Thr Arg Lys His Tyr Gln Pro Tyr Ala Pro Pro Arg Asp Phe Ala
305                 310                 315                 320

Ala Tyr Arg Ser Arg Val Lys Phe Ser Arg Ser Ala Asp Ala Pro Ala
                325                 330                 335

Tyr Gln Gln Gly Gln Asn Gln Leu Tyr Asn Glu Leu Asn Leu Gly Arg
            340                 345                 350

Arg Glu Glu Tyr Asp Val Leu Asp Lys Arg Arg Gly Arg Asp Pro Glu
        355                 360                 365

Met Gly Gly Lys Pro Arg Arg Lys Asn Pro Gln Glu Gly Leu Tyr Asn
    370                 375                 380

Glu Leu Gln Lys Asp Lys Met Ala Glu Ala Tyr Ser Glu Ile Gly Met
385                 390                 395                 400

Lys Gly Glu Arg Arg Arg Gly Lys Gly His Asp Gly Leu Tyr Gln Gly
                405                 410                 415

Leu Ser Thr Ala Thr Lys Asp Thr Tyr Asp Ala Leu His Met Gln Ala
            420                 425                 430

Leu Pro Pro Arg
        435

<210> SEQ ID NO 61
<211> LENGTH: 251
<212> TYPE: PRT
<213> ORGANISM: Artificial sequence
<220> FEATURE:
<223> OTHER INFORMATION: Anti-CD20-(GA101)-ds-scFv

<400> SEQUENCE: 61

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Cys Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Gly Gly Gly Ser Asp Ile Val Met Thr
    130                 135                 140

Gln Thr Pro Leu Ser Leu Pro Val Thr Pro Gly Glu Pro Ala Ser Ile
145                 150                 155                 160

Ser Cys Arg Ser Ser Lys Ser Leu Leu His Ser Asn Gly Ile Thr Tyr
                165                 170                 175
```

```
Leu Tyr Trp Tyr Leu Gln Lys Pro Gly Gln Ser Pro Gln Leu Leu Ile
            180                 185                 190

Tyr Gln Met Ser Asn Leu Val Ser Gly Val Pro Asp Arg Phe Ser Gly
            195                 200                 205

Ser Gly Ser Gly Thr Asp Phe Thr Leu Lys Ile Ser Arg Val Glu Ala
        210                 215                 220

Glu Asp Val Gly Val Tyr Tyr Cys Ala Gln Asn Leu Glu Leu Pro Tyr
225                 230                 235                 240

Thr Phe Gly Cys Gly Thr Lys Val Glu Ile Lys
                245                 250

<210> SEQ ID NO 62
<211> LENGTH: 119
<212> TYPE: PRT
<213> ORGANISM: Artificial sequence
<220> FEATURE:
<223> OTHER INFORMATION: Anti-CD20-(GA101)- ds-Fab VH

<400> SEQUENCE: 62

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Cys Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 63
<211> LENGTH: 112
<212> TYPE: PRT
<213> ORGANISM: Artificial sequence
<220> FEATURE:
<223> OTHER INFORMATION: Anti-CD20-(GA101)- ds-Fab VL

<400> SEQUENCE: 63

Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Cys Gly Thr Lys Val Glu Ile Lys
```

<210> SEQ ID NO 64
<211> LENGTH: 1364
<212> TYPE: DNA
<213> ORGANISM: Artificial sequence
<220> FEATURE:
<223> OTHER INFORMATION: Anti-CD20-(GA101)-ds-Fab-CD28ATD-CD28CSD-
CD3zSSD fusion pETR17162

<400> SEQUENCE: 64

```
atgggatgga gctgtatcat cctcttcttg gtagcaacag ctaccggtgt gcattcccag      60
gtgcaattgg tgcagtctgg cgctgaagtt aagaagcctg ggagttcagt gaaggtctcc    120
tgcaaggctt ccggttacgc cttcagctat tcttggatca attgggtgcg gcaggcgcct    180
ggacaatgtc tcgagtggat gggacggatc tttcccggcg atgggatac tgactacaat     240
gggaaattca aggcagagt cacaattacc gccgacaaat ccactagcac agcctatatg     300
gagctgagca gcctgagatc tgaggacacg gccgtgtatt actgtgcaag aaatgtcttt    360
gatggttact ggcttgttta ctggggccag ggaaccctgg tcaccgtctc ctcaggaggg    420
ggcggaagtg gtggcggggg aagcggcggg ggtggcagcg gaggggcgg atctgacatc     480
gtgatgaccc agactccact ctccctgccc gtcaccctg gagagcccgc cagcattagc    540
tgcaggtcta gcaagagcct cttgcacagc aatggcatca cttatttgta ttggtacctg    600
caaaagccag gcagtctcc acagctcctg atttatcaaa tgtccaacct tgtctctggc    660
gtccctgacc gcttctccgg ttccgggtca ggcactgatt tcacactgaa aatcagcagg    720
gtggaggctg aggatgttgg agtttattac tgcgctcaga tctagaact tccttacacc    780
ttcggctgtg ggaccaaggt ggagatcaag gaggggcgg atccttctgg gtgctggtgg    840
tggtgggcgg cgtgctggcc tgctacagcc tgctggtgac cgtggccttc atcatcttct    900
gggtgaggag caagaggagc aggctgctgc acagcgacta catgaacatg accccccagga   960
ggcccggccc caccaggaag cactaccagc cctacgcccc cccagggac ttcgccgcct    1020
acaggagcag ggtgaagttc agcaggagcg ccgacgcccc cgcctaccag cagggccaga   1080
accagctgta taacgagctg aacctgggca ggagggagga gtacgacgtg ctggacaaga   1140
ggaggggcag ggaccccgag atgggcggca gcccaggag aagaacccc caggagggcc    1200
tgtataacga gctgcagaag acaagatgg ccgaggccta cagcgagatc ggcatgaagg   1260
gcgagaggag gaggggcaag ggccacgacg gcctgtacca gggcctgagc accgccacca   1320
aggacaccta cgacgccctg cacatgcagg ccctgccccc cagg                    1364
```

<210> SEQ ID NO 65
<211> LENGTH: 357
<212> TYPE: DNA
<213> ORGANISM: Artificial sequence
<220> FEATURE:
<223> OTHER INFORMATION: Anti-CD20-(GA101)- ds-Fab VH

<400> SEQUENCE: 65

```
caggtgcaat ggtgcagtc tggcgctgaa gttaagaagc ctgggagttc agtgaaggtc      60
tcctgcaagg cttccggtta cgccttcagc tattcttgga tcaattgggt gcggcaggcg    120
cctggacaat gtctcgagtg gatgggacgg atctttcccg gcgatgggga tactgactac    180
aatgggaaat caagggcag agtcacaatt accgccgaca aatccactag cacagcctat    240
atggagctga gcagcctgag atctgaggac acggccgtgt attactgtgc aagaaatgtc    300
```

```
tttgatggtt actggcttgt ttactggggc cagggaaccc tggtcaccgt ctcctca        357
```

```
<210> SEQ ID NO 66
<211> LENGTH: 336
<212> TYPE: DNA
<213> ORGANISM: Artificial sequence
<220> FEATURE:
<223> OTHER INFORMATION: Anti-CD20-(GA101)- ds-Fab VL

<400> SEQUENCE: 66
gacatcgtga tgacccagac tccactctcc ctgcccgtca cccctggaga gcccgccagc     60
attagctgca ggtctagcaa gagcctcttg cacagcaatg gcatcactta tttgtattgg    120
tacctgcaaa agccagggca gtctccacag ctcctgattt atcaaatgtc caaccttgtc    180
tctggcgtcc ctgaccgctt ctccggttcc gggtcaggca ctgatttcac actgaaaatc    240
agcagggtgg aggctgagga tgttggagtt tattactgcg ctcagaatct agaacttcct    300
tacaccttcg gctgtgggac caaggtggag atcaaa                              336
```

```
<210> SEQ ID NO 67
<211> LENGTH: 2151
<212> TYPE: DNA
<213> ORGANISM: Artificial sequence
<220> FEATURE:
<223> OTHER INFORMATION: Anti-CD20-(GA101)-ds-scFv-CD28ATD-CD28CSD-
      CD3zSSD-eGFP fusion pETR17162

<400> SEQUENCE: 67
gccaccatgg gatggagctg tatcatcctc ttcttggtag caacagctac cggtgtgcat      60
tcccaggtgc aattggtgca gtctggcgct gaagttaaga agcctgggag ttcagtgaag     120
gtctcctgca aggcttccgg ttacgccttc agctattctt ggatcaattg ggtgcggcag     180
gcgcctggac aatgtctcga gtggatggga cggatctttc ccggcgatgg ggatactgac     240
tacaatggga aattcaaggg cagagtcaca attaccgccg acaaatccac tagcacagcc     300
tatatggagc tgagcagcct gagatctgag gacacggccg tgtattactg tgcaagaaat     360
gtctttgatg gttactggct tgtttactgg ggccagggaa ccctggtcac cgtctcctca     420
ggaggggggcg gaagtggtgg cggggggaagc ggcgggggtg gcagcggagg gggcggatct     480
gacatcgtga tgacccagac tccactctcc ctgcccgtca cccctggaga gcccgccagc     540
attagctgca ggtctagcaa gagcctcttg cacagcaatg gcatcactta tttgtattgg     600
tacctgcaaa agccagggca gtctccacag ctcctgattt atcaaatgtc caaccttgtc     660
tctggcgtcc ctgaccgctt ctccggttcc gggtcaggca ctgatttcac actgaaaatc     720
agcagggtgg aggctgagga tgttggagtt tattactgcg ctcagaatct agaacttcct     780
tacaccttcg gctgtgggac caaggtggag atcaaaggag ggggcggatc cttctgggtg     840
ctggtggtgg tgggcggcgt gctggcctgc tacagcctgc tggtgaccgt ggccttcatc     900
atcttctggg tgaggagcaa gaggagcagg ctgctgcaca cgcgactaca tgaacatgacc     960
cccaggaggc ccggccccac caggaagcac taccagccct acgcccccccc cagggacttc    1020
gccgcctaca ggagcagggt gaagttcagc aggagcgccg acgcccccgc ctaccagcag    1080
ggccagaacc agctgtataa cgagctgaac ctggcagga ggaggagta cgacgtgctg      1140
gacaagagga ggggcaggga ccccgagatg ggcggcaagc caggaggaa gaacccccag    1200
gagggcctgt ataacgagct gcagaaggac aagatggccg aggcctacag cgagatcggc    1260
atgaagggcg agaggaggag gggcaagggc cacgacggcc tgtaccaggg cctgagcacc    1320
```

```
gccaccaagg acacctacga cgccctgcac atgcaggccc tgccccccag gtccggagag    1380
ggcagaggaa gtcttctaac atgcggtgac gtggaggaga atcccggccc tagggtgagc    1440
aagggcgagg agctgttcac cggggtggtg cccatcctgg tcgagctgga cggcgacgta    1500
aacggccaca gttcagcgt gtccggcgag ggcgagggcg atgccaccta cggcaagctg     1560
accctgaagt tcatctgcac caccggcaag ctgcccgtgc cctggcccac cctcgtgacc    1620
accctgacct acggcgtgca gtgcttcagc cgctaccccg accacatgaa gcagcacgac    1680
ttcttcaagt ccgccatgcc cgaaggctac gtccaggagc gcaccatctt cttcaaggac    1740
gacggcaact acaagacccg cgccgaggtg aagttcgagg gcgacaccct ggtgaaccgc    1800
atcgagctga agggcatcga cttcaaggag gacggcaaca tcctgggca caagctggag    1860 tacaactaca cagccacaa cgtctatatc atggccgaca gcagaagaa cggcatcaag     1920 gtgaacttca agatccgcca caacatcgag gacggcagcg tgcagctcgc cgaccactac    1980
cagcagaaca cccccatcgg cgacggcccc gtgctgctgc ccgacaacca ctacctgagc    2040
acccagtccg ccctgagcaa agaccccaac gagaagcgcg atcacatggt cctgctggag    2100
ttcgtgaccg ccgccgggat cactctcggc atggacgagc tgtacaagtg a             2151
```

<210> SEQ ID NO 68
<211> LENGTH: 164
<212> TYPE: PRT
<213> ORGANISM: Homo sapiens

<400> SEQUENCE: 68

```
Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
    50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Gly Arg Asp Pro Glu Met
                85                  90                  95

Gly Gly Lys Pro Gln Arg Arg Lys Asn Pro Gln Glu Gly Leu Tyr Asn
            100                 105                 110

Glu Leu Gln Lys Asp Lys Met Ala Glu Ala Tyr Ser Glu Ile Gly Met
        115                 120                 125

Lys Gly Glu Arg Arg Arg Gly Lys Gly His Asp Gly Leu Tyr Gln Gly
    130                 135                 140

Leu Ser Thr Ala Thr Lys Asp Thr Tyr Asp Ala Leu His Met Gln Ala
145                 150                 155                 160

Leu Pro Pro Arg
```

<210> SEQ ID NO 69
<211> LENGTH: 492
<212> TYPE: DNA
<213> ORGANISM: Homo sapiens

<400> SEQUENCE: 69

```
atgaagtgga aggcgctttt caccgcggcc atcctgcagg cacagttgcc gattacagag    60
gcacagagct ttggcctgct ggatcccaaa ctctgctacc tgctggatgg aatcctcttc   120
```

```
atctatggtg tcattctcac tgccttgttc ctgagagtga agttcagcag gagcgcagag    180
ccccccgcgt accagcaggg ccagaaccag ctctataacg agctcaatct aggacgaaga    240
gaggagtacg atgttttgga caagagacgt ggccgggacc ctgagatggg gggaaagccg    300
agaaggaaga accctcagga aggcctgtac aatgaactgc agaaagataa gatggcggag    360
gcctacagtg agattgggat gaaaggcgag cgccggaggg gcaaggggca cgatggcctt    420
taccagggtc tcagtacagc caccaaggac acctacgacg cccttcacat gcaggccctg    480 cccccctcgct aa                                                      492
```

```
<210> SEQ ID NO 70
<211> LENGTH: 164
<212> TYPE: PRT
<213> ORGANISM: Mus musculus

<400> SEQUENCE: 70

Met Lys Trp Lys Val Ser Val Leu Ala Cys Ile Leu His Val Arg Phe
1               5                   10                  15

Pro Gly Ala Glu Ala Gln Ser Phe Gly Leu Leu Asp Pro Lys Leu Cys
                20                  25                  30

Tyr Leu Leu Asp Gly Ile Leu Phe Ile Tyr Gly Val Ile Ile Thr Ala
            35                  40                  45

Leu Tyr Leu Arg Ala Lys Phe Ser Arg Ser Ala Glu Thr Ala Ala Asn
        50                  55                  60

Leu Gln Asp Pro Asn Gln Leu Tyr Asn Glu Leu Asn Leu Gly Arg Arg
65                  70                  75                  80

Glu Glu Tyr Asp Val Leu Glu Lys Lys Arg Ala Arg Asp Pro Glu Met
                85                  90                  95

Gly Gly Lys Gln Gln Arg Arg Arg Asn Pro Gln Glu Gly Val Tyr Asn
                100                 105                 110

Ala Leu Gln Lys Asp Lys Met Ala Glu Ala Tyr Ser Glu Ile Gly Thr
            115                 120                 125

Lys Gly Glu Arg Arg Arg Gly Lys Gly His Asp Gly Leu Tyr Gln Gly
        130                 135                 140

Leu Ser Thr Ala Thr Lys Asp Thr Tyr Asp Ala Leu His Met Gln Thr
145                 150                 155                 160

Leu Ala Pro Arg
```

```
<210> SEQ ID NO 71
<211> LENGTH: 495
<212> TYPE: DNA
<213> ORGANISM: Mus musculus

<400> SEQUENCE: 71
atgaagtgga aagtgtctgt tctcgcctgc atcctccacg tgcggttccc aggagcagag     60
gcacagagct tggtctgctg gatcccaaa ctctgctact tgctagatgg aatcctcttc    120
atctacggag tcatcatcac agccctgtac ctgagagcaa aattcagcag gagtgcagag    180
actgctgcca acctgcagga ccccaaccag ctctacaatg agctcaatct agggcgaaga    240
gaggaatatg acgtcttgga gaagaagcgg gctcgggatc cagagatggg aggcaaacag    300
cagaggagga ggaaccccca ggaaggcgta tacaatgcac tgcagaaaga caagatggca    360
gaagcctaca gtgagatcgg cacaaaaggc gagaggcgga gaggcaaggg gcacgatggc    420
ctttaccagg gtctcagcac tgccaccaag gacacctatg atgccctgca tatgcagacc    480
```

-continued

```
ctggcccctc gctaa                                                495
```

<210> SEQ ID NO 72
<211> LENGTH: 660
<212> TYPE: DNA
<213> ORGANISM: Homo sapiens

<400> SEQUENCE: 72

```
atgctgcgcc tgctgctggc gctgaacctg tttccgagca ttcaggtgac cggcaacaaa      60
attctggtga acagagccc gatgctggtg gcgtatgata cgcggtgaa cctgagctgc      120
aaatatagct ataacctgtt tagccgcgaa tttcgcgcga gcctgcataa aggcctggat      180
agcgcggtgg aagtgtgcgt ggtgtatggc aactatagcc agcagctgca ggtgtatagc      240
aaaaccggct ttaactgcga tggcaaactg ggcaacgaaa gcgtgacctt ttatctgcag      300
aacctgtatg tgaaccagac cgatatttat ttttgcaaaa ttgaagtgat gtatccgccg      360
ccgtatctgg ataacgaaaa agcaacggc accattattc atgtgaaagg caaacatctg      420
tgcccgagcc cgctgtttcc gggcccgagc aaaccgtttt gggtgctggt ggtggtgggc      480
ggcgtgctgg cgtgctatag cctgctggtg accgtggcgt ttattatttt ttgggtgcgc      540
agcaaacgca gccgcctgct gcatagcgat tatatgaaca tgaccccgcg ccgcccgggc      600
ccgacccgca acattatca gccgtatgcg ccgccgcgcg attttgcggc gtatcgcagc      660
```

<210> SEQ ID NO 73
<211> LENGTH: 220
<212> TYPE: PRT
<213> ORGANISM: Homo sapiens

<400> SEQUENCE: 73

```
Met Leu Arg Leu Leu Leu Ala Leu Asn Leu Phe Pro Ser Ile Gln Val
 1               5                  10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
        35                  40                  45

Arg Glu Phe Arg Ala Ser Leu His Lys Gly Leu Asp Ser Ala Val Glu
    50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
        115                 120                 125

Asn Gly Thr Ile Ile His Val Lys Gly Lys His Leu Cys Pro Ser Pro
    130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
        195                 200                 205
```

```
Tyr Ala Pro Pro Arg Asp Phe Ala Ala Tyr Arg Ser
    210                 215                 220
```

```
<210> SEQ ID NO 74
<211> LENGTH: 654
<212> TYPE: DNA
<213> ORGANISM: Mus musculus

<400> SEQUENCE: 74
atgaccctgc gcctgctgtt tctggcgctg aacttttta gcgtgcaggt gaccgaaaac      60
aaaattctgg tgaaacagag cccgctgctg gtggtggata gcaacgaagt gagcctgagc    120
tgccgctata gctataacct gctggcgaaa gaatttcgcg cgagcctgta taaaggcgtg    180
aacagcgatg tggaagtgtg cgtgggcaac ggcaactttt acctatcagcc gcagtttcgc    240 agcaacgcgg aatttaactg cgatggcgat tttgataacg aaaccgtgac ctttcgcctg    300
tggaacctgc atgtgaacca taccgatatt tattttgca aaattgaatt tatgtatccg    360
ccgccgtatc tggataacga acgcagcaac ggcaccatta ttcatattaa agaaaaacat    420
ctgtgccata cccagagcag cccgaaactg ttttgggcgc tggtggtggt ggcgggcgtg    480
ctgttttgct atggcctgct ggtgaccgtg gcgctgtgcg tgatttggac caacagccgc    540
cgcaaccgcc tgctgcagag cgattatatg aacatgaccc cgcgccgccc gggcctgacc    600
cgcaaaccgt atcagccgta tgcgccggcg cgcgattttg cggcgtatcg cccg          654
```

```
<210> SEQ ID NO 75
<211> LENGTH: 218
<212> TYPE: PRT
<213> ORGANISM: Mus musculus

<400> SEQUENCE: 75

Met Thr Leu Arg Leu Leu Phe Leu Ala Leu Asn Phe Phe Ser Val Gln
1               5                   10                  15

Val Thr Glu Asn Lys Ile Leu Val Lys Gln Ser Pro Leu Leu Val Val
            20                  25                  30

Asp Ser Asn Glu Val Ser Leu Ser Cys Arg Tyr Ser Tyr Asn Leu Leu
        35                  40                  45

Ala Lys Glu Phe Arg Ala Ser Leu Tyr Lys Gly Val Asn Ser Asp Val
    50                  55                  60

Glu Val Cys Val Gly Asn Gly Asn Phe Thr Tyr Gln Pro Gln Phe Arg
65                  70                  75                  80

Ser Asn Ala Glu Phe Asn Cys Asp Gly Asp Phe Asp Asn Glu Thr Val
                85                  90                  95

Thr Phe Arg Leu Trp Asn Leu His Val Asn His Thr Asp Ile Tyr Phe
            100                 105                 110

Cys Lys Ile Glu Phe Met Tyr Pro Pro Tyr Leu Asp Asn Glu Arg
        115                 120                 125

Ser Asn Gly Thr Ile Ile His Ile Lys Glu Lys His Leu Cys His Thr
    130                 135                 140

Gln Ser Ser Pro Lys Leu Phe Trp Ala Leu Val Val Val Ala Gly Val
145                 150                 155                 160

Leu Phe Cys Tyr Gly Leu Leu Val Thr Val Ala Leu Cys Val Ile Trp
                165                 170                 175

Thr Asn Ser Arg Arg Asn Arg Leu Leu Gln Ser Asp Tyr Met Asn Met
            180                 185                 190

Thr Pro Arg Arg Pro Gly Leu Thr Arg Lys Pro Tyr Gln Pro Tyr Ala
        195                 200                 205
```

Pro Ala Arg Asp Phe Ala Ala Tyr Arg Pro
    210                 215

<210> SEQ ID NO 76
<211> LENGTH: 4
<212> TYPE: PRT
<213> ORGANISM: Artificial sequence
<220> FEATURE:
<223> OTHER INFORMATION: CD28 YMNM

<400> SEQUENCE: 76

Tyr Met Asn Met
1

<210> SEQ ID NO 77
<211> LENGTH: 4
<212> TYPE: PRT
<213> ORGANISM: Artificial sequence
<220> FEATURE:
<223> OTHER INFORMATION: CD28 PYAP

<400> SEQUENCE: 77

Pro Tyr Ala Pro
1

<210> SEQ ID NO 78
<211> LENGTH: 21
<212> TYPE: PRT
<213> ORGANISM: Artificial sequence
<220> FEATURE:
<223> OTHER INFORMATION: Signal peptide

<400> SEQUENCE: 78

Ala Thr Met Gly Trp Ser Cys Ile Ile Leu Phe Leu Val Ala Thr Ala
1               5                   10                  15

Thr Gly Val His Ser
            20

<210> SEQ ID NO 79
<211> LENGTH: 57
<212> TYPE: DNA
<213> ORGANISM: Artificial sequence
<220> FEATURE:
<223> OTHER INFORMATION: Signal peptide DNA sequence

<400> SEQUENCE: 79
atgggatgga gctgtatcat cctcttcttg gtagcaacag ctaccggtgt gcactcc      57

<210> SEQ ID NO 80
<211> LENGTH: 116
<212> TYPE: PRT
<213> ORGANISM: Artificial sequence
<220> FEATURE:
<223> OTHER INFORMATION: Anti-WT1 (33F05) VH

<400> SEQUENCE: 80

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Asn Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

```
Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Ser Tyr Tyr Glu Ala Phe Asp Tyr Trp Gly Gln Gly Thr Leu Val
            100                 105                 110

Thr Val Ser Ser
        115

<210> SEQ ID NO 81
<211> LENGTH: 107
<212> TYPE: PRT
<213> ORGANISM: Artificial sequence
<220> FEATURE:
<223> OTHER INFORMATION: Anti-WT1 (33F05) VL

<400> SEQUENCE: 81

Ser Ser Glu Leu Thr Gln Asp Pro Ala Val Ser Val Ala Leu Gly Gln
 1               5                  10                  15

Thr Val Arg Ile Thr Cys Gln Gly Asp Ser Leu Arg Ser Tyr Tyr Ala
             20                  25                  30

Ser Trp Tyr Gln Gln Lys Pro Gly Gln Ala Pro Val Leu Val Ile Tyr
         35                  40                  45

Gly Lys Asn Asn Arg Pro Ser Gly Ile Pro Asp Arg Phe Ser Gly Ser
 50                  55                  60

Ser Ser Gly Asn Thr Ala Ser Leu Thr Ile Thr Gly Ala Gln Ala Glu
 65                  70                  75                  80

Asp Glu Ala Asp Tyr Tyr Cys Asn Ser Pro Asp Met Asn Gly Asn Ala
                 85                  90                  95

Val Phe Gly Gly Gly Thr Lys Leu Thr Val Leu
            100                 105

<210> SEQ ID NO 82
<211> LENGTH: 120
<212> TYPE: PRT
<213> ORGANISM: Artificial sequence
<220> FEATURE:
<223> OTHER INFORMATION: Anti-WT1 (11D06) VH

<400> SEQUENCE: 82

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
             20                  25                  30

Ala Ile Ser Trp Val Arg Gln Ala Pro Gly Gln Gly Leu Glu Trp Met
         35                  40                  45

Gly Gly Ile Ile Pro Ile Phe Gly Thr Ala Asn Tyr Ala Gln Lys Phe
 50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Ile Glu Leu Trp Trp Gly Gly Phe Asp Tyr Trp Gly Gln
            100                 105                 110

Gly Thr Thr Val Thr Val Ser Ser
        115                 120
```

```
<210> SEQ ID NO 83
<211> LENGTH: 106
<212> TYPE: PRT
<213> ORGANISM: Artificial sequence
<220> FEATURE:
<223> OTHER INFORMATION: Anti-WT1 (11D06) VL

<400> SEQUENCE: 83

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
50                  55                  60

Ser Gly Ser Gly Thr Glu Phe Thr Leu Thr Ile Gly Ser Leu Gln Pro
65                  70                  75                  80

Asp Asp Phe Ala Thr Tyr Tyr Cys Gln Gln Tyr Glu Asp Tyr Thr Thr
                85                  90                  95

Phe Gly Gln Gly Thr Lys Val Glu Ile Lys
            100                 105

<210> SEQ ID NO 84
<211> LENGTH: 119
<212> TYPE: PRT
<213> ORGANISM: Artificial sequence
<220> FEATURE:
<223> OTHER INFORMATION: Anti-WT1 (33H09) VH

<400> SEQUENCE: 84

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Asp Leu Phe Ser Leu Asp Tyr Trp Gly Gln Gly
            100                 105                 110

Thr Thr Val Thr Val Ser Ser
        115

<210> SEQ ID NO 85
<211> LENGTH: 106
<212> TYPE: PRT
<213> ORGANISM: Artificial sequence
<220> FEATURE:
<223> OTHER INFORMATION: Anti-WT1 (33H09) VL

<400> SEQUENCE: 85

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30
```

```
Leu Ala Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Tyr Asp Gly Ile Thr
                85                  90                  95

Phe Gly Gln Gly Thr Lys Val Glu Ile Lys
            100                 105
```

<210> SEQ ID NO 86
<211> LENGTH: 119
<212> TYPE: PRT
<213> ORGANISM: Artificial sequence
<220> FEATURE:
<223> OTHER INFORMATION: Anti-WT1 (5E11) VH

<400> SEQUENCE: 86

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ser Tyr Asp Leu Tyr Ser Phe Asp Tyr Trp Gly Gln Gly
            100                 105                 110

Thr Thr Val Thr Val Ser Ser
        115
```

<210> SEQ ID NO 87
<211> LENGTH: 108
<212> TYPE: PRT
<213> ORGANISM: Artificial sequence
<220> FEATURE:
<223> OTHER INFORMATION: Anti-WT1 (5E11) VL

<400> SEQUENCE: 87

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ser Phe Pro Pro Met
                85                  90                  95

Ile Thr Phe Gly Gln Gly Thr Lys Val Glu Ile Lys
```

<210> SEQ ID NO 88
<211> LENGTH: 5
<212> TYPE: PRT
<213> ORGANISM: Artificial sequence
<220> FEATURE:
<223> OTHER INFORMATION: Anti-CD3 HCDR1 Kabat

<400> SEQUENCE: 88

Thr Tyr Ala Met Asn
1               5

<210> SEQ ID NO 89
<211> LENGTH: 19
<212> TYPE: PRT
<213> ORGANISM: Artificial sequence
<220> FEATURE:
<223> OTHER INFORMATION: Anti-CD3 HCDR2 Kabat

<400> SEQUENCE: 89

Arg Ile Arg Ser Lys Tyr Asn Asn Tyr Ala Thr Tyr Tyr Ala Asp Ser
1               5                   10                  15

Val Lys Gly

<210> SEQ ID NO 90
<211> LENGTH: 14
<212> TYPE: PRT
<213> ORGANISM: Artificial sequence
<220> FEATURE:
<223> OTHER INFORMATION: Anti-CD3 HCDR3 Kabat

<400> SEQUENCE: 90

His Gly Asn Phe Gly Asn Ser Tyr Val Ser Trp Phe Ala Tyr
1               5                   10

<210> SEQ ID NO 91
<211> LENGTH: 14
<212> TYPE: PRT
<213> ORGANISM: Artificial sequence
<220> FEATURE:
<223> OTHER INFORMATION: Anti-CD3 LCDR1 Kabat

<400> SEQUENCE: 91

Gly Ser Ser Thr Gly Ala Val Thr Thr Ser Asn Tyr Ala Asn
1               5                   10

<210> SEQ ID NO 92
<211> LENGTH: 7
<212> TYPE: PRT
<213> ORGANISM: Artificial sequence
<220> FEATURE:
<223> OTHER INFORMATION: Anti-CD3 LCDR2 Kabat

<400> SEQUENCE: 92

Gly Thr Asn Lys Arg Ala Pro
1               5

<210> SEQ ID NO 93
<211> LENGTH: 9
<212> TYPE: PRT
<213> ORGANISM: Artificial sequence
<220> FEATURE:
<223> OTHER INFORMATION: Anti-CD3 LCDR3 Kabat

```
<400> SEQUENCE: 93

Ala Leu Trp Tyr Ser Asn Leu Trp Val
1               5
```

CAR-T CELL ASSAY FOR SPECIFICITY TEST OF NOVEL ANTIGEN BINDING MOIETIES

CROSS-REFERENCE TO RELATED APPLICATIONS

This application is a continuation of International Application No. PCT/EP2018/086067, filed Dec. 20, 2018, which claims benefit to European Patent Application No. 17209198.5, filed Dec. 21, 2017; all of which are hereby expressly incorporated by reference in their entirety as though fully set forth herein.

SEQUENCE LISTING

This application contains a Sequence Listing which has been submitted via EFS-Web and is hereby incorporated by reference in its entirety. Said ASCII copy, created on Jun. 10, 2020, is named P34478-US Sequence Listing.txt and is 122,601 bytes in size.

FIELD OF THE INVENTION

The present invention generally relates to specificity assays using cell cultures, in particular to chimeric antigen receptor (CAR) expressing reporter T (CAR-T cell) assays to test antigen binding moieties in different formats. Furthermore, the present invention relates to the use of CAR-T cells, transfected/transduced with an engineered chimeric antigen receptor (CAR) comprising a target antigen binding moiety capable of specific binding to a target antigen, e.g., tumor associated antigens.

BACKGROUND

Chemotherapy is until now still one of the most commonly used treatments for cancer. Additionally, antibody based therapies have evolved over the last 15 years and represent now a valuable combination or alternative to chemotherapeutic approaches in the treatment of hematological malignancies and solid tumors. Unlike chemotherapy, antibody therapies target specific antigens on cancer cells thus allowing a more site-directed treatment thereby reducing the side effects on healthy tissue. In the process of developing an antibody-based therapeutic reagent, various assays are required to identify the best candidates to bring into clinical trials and eventually to the market. In a first early preclinical phase, the antibodies and, especially, their antigen binding moieties have to be generated and analyzed for their target-specificity, as well as their affinity to the target.

Binding properties can be analyzed using various protein-protein interaction assays, such as FRET-based methods, Surface Plasmon Resonance (SPR) or fluorescence-activated cell sorting (FACS). However, available assay formats might not always reproduce the in vivo situation comprehensively and integrative. For example targeting of cancer cells with therapeutic antibodies binding to cell surface receptors can have impacts on multiple levels, e.g., intracellular signaling via the binding and cross-linking of surface molecules as well as marking the tumor cells to engage immune cells. Furthermore, the recognition cascade from antigen binding to establishing of an effector function, e.g., T cell cytotoxicity, requires a well-orchestrated sequence of cell surface interactions, wherein binding affinity of an antigen binding moiety is one among several factors. Plain protein-protein affinity interaction assays may therefore not result with the complete picture, although these assays are a very valuable tool for early candidate development.

Conclusively, there remains a need to develop binding assays which do more closely mimic the situation in vivo in a more comprehensive setup minimizing non-specific effects on target-antibody binding as far as possible. Furthermore, designing combination assays which allow assessment of binding and functionality at an early state in the development process of an antibody therapeutic molecule would be of great benefit.

The inventors of the present invention developed a novel assay which is applicable to a wide variety of different cancer cell types to assess binding of antibodies to their target. The innovative assay includes modified T cells as reporter cells combining straight-forward readout with a comprehensive and inclusive result. Furthermore, the present invention provides assays which combine the assessment of binding and functionality of antibodies and antibody-like constructs (e.g., ligands). The novel assay is useful for example for screening or characterization purposes of therapeutic antibody drug candidates, e.g., in high-throughput formats.

This new assay represents a valuable tool for early and late screening and characterization of antibody binding to the native target and assessing functionality which will allow identifying the best binders at an early stage in the development of the drug candidate.

SUMMARY OF THE INVENTION

The present invention generally relates to a method for selecting novel antigen binding moieties, particularly in the drug development process, and combines the assessment of binding to a target antigen, e.g., on a tumor cell, with the activation of T cells in response to the antibody-target binding.

Accordingly, herein provided is a method for assessing the specificity of an antigen binding moiety comprising the steps of:
a. providing an antigen binding moiety specific for a target antigen;
b. generating a chimeric antigen receptor (CAR) expressing reporter T (CAR-T) cell by:
   i. transferring the antigen binding moiety into a CAR vector system operationally coupled to a response element;
   ii. transferring the CAR vector system into a reporter T cell comprising a reporter gene under the control of the response element;
c. contacting the reporter CAR-T cell with a target cell comprising the target antigen on the surface, in particular wherein the target cell is a cancer cell; and
d. determining T cell activation by determining the expression of the reporter gene to establish the specificity of the antigen binding moiety.

In one embodiment, the antigen binding moiety is a Fab fragment, in particular a Fab fragment deriving from a phage display library screening.

In one embodiment, the antigen binding moiety comprises a variable heavy chain domain (VH) and a variable light chain domain (VL). In one embodiment, the VH and VL domains of the antigen binding moiety are transferred to the CAR.

In one embodiment, the CAR vector system encodes a CAR comprising a Fab or a crossFab fragment, an anchoring transmembrane domain and at least one intracellular signaling and/or co-signaling domain.

In one embodiment, binding of the target antigen to the reporter CAR-T cell leads to activation of the intracellular signaling and/or co-signaling domain.

In one embodiment, activation of the intracellular signaling domain leads to activation of the response element.

In one embodiment, the response element controls the expression of the reporter gene.

In one embodiment, activation of the response element leads to expression of the reporter gene.

In one embodiment, the response element is part of the NFAT pathway, the NF-κB pathway or the AP-1 pathway.

In one embodiment, the reporter gene is coding for a luminescent protein, in particular for a fluorescent protein.

In one embodiment, the reporter gene is coding for green fluorescent protein (GFP) or luciferase.

In one embodiment, the target antigen is a cell surface receptor.

In one embodiment, the target antigen is a peptide bound to a molecule of the human major histocompatibility complex (MHC).

In one embodiment, the antigen binding moiety is a T cell receptor like (TCRL) antigen binding moiety.

In one embodiment, the method additionally comprises the step of:
e) comparing the level of expression of the reporter gene to a reference.

In one embodiment, the reference is expression of the reporter gene in absence of the target cell.

In one embodiment, the expression of the reporter gene is at least 2×, 3×, 4×, 5×, 10×, 100×, 1000×, or 10000×, higher compared to the expression of the reporter gene in absence of the target cell.

In one embodiment, the method additionally comprises the step of:
f) selecting the novel antigen binding moiety if the level of expression of the reporter gene in the presence of the target cell in relation to the expression of the reporter gene in absence of the target cell is higher than a predefined threshold value.

In one embodiment, the threshold value is 2, 3, 4, 5, 10, 100, 1000, or 10000.

In one embodiment, high level of expression of the reporter gene in the presence of the target cell and low level of expression of the reporter gene in the absence of the target cell is indicative for high specificity of the antigen binding moiety, in particular for high specificity of a T cell bispecific (TCB) antibody comprising the antigen binding moiety.

In one embodiment, the method is an in vitro method.

In one embodiment, provided is a method for generating a TCB antibody, wherein the TCB antibody format comprises a first antigen binding moiety specific for a target antigen and a second antigen binding moiety capable of specific binding to a T cell activating receptor, wherein the first antigen binding moiety is selected according to the method as described herein.

In one embodiment, the T cell activating receptor is CD3.

SHORT DESCRIPTION OF THE FIGURES

FIG. 1 shows a schematic representation of a Jurkat NFAT reporter CAR-T cell assay. A tumor associated antigen (TAA) can be recognized by the anti-TAA antigen binding receptor expressing Jurkat NFAT reporter CAR-T cell. This recognition leads to the activation of the cell which can be detected by measuring luminescence (cps).

FIG. 2A-2F depicts the architecture of different CAR formats used in the present invention.

FIG. 2A shows the architecture of the Fab format. Depicted is the extracellular domain comprising an antigen binding moiety which consists of an Ig heavy chain fragment and an Ig light chain. Attached to the heavy chain, a linker connects the antigen recognition domain with an anchoring transmembrane domain (ATD) which is fused to an intracellular co-stimulatory signaling domain (CSD) which in turn is fused to a stimulatory signaling domain (SSD).

FIG. 2B shows the architecture of the Fab format with heavy and light chain swap. Depicted is the extracellular domain comprising an antigen binding moiety which consists of an Ig heavy chain fragment and an Ig light chain. Attached to the light chain constant domain, a linker connects the antigen recognition domain with an anchoring transmembrane domain (ATD) which is fused to an intracellular co-stimulatory signaling domain (CSD) which in turn is fused to a stimulatory signaling domain (SSD).

FIG. 2C shows the architecture of the scFab format. Depicted is the extracellular domain comprising an antigen binding moiety which consists of an Ig heavy chain fragment and an Ig light chain, both connected by a linker. Attached to the heavy chain, a linker connects the antigen recognition domain with an anchoring transmembrane domain (ATD) which is fused to an intracellular co-stimulatory signaling domain (CSD) which in turn is fused to a stimulatory signaling domain (SSD).

FIG. 2D shows the architecture of the crossFab format with VH-VL swap. Depicted is the extracellular domain comprising an antigen binding moiety which consists of an Ig heavy chain fragment and an Ig light chain wherein the VH and VL domains are exchanged. Attached to the heavy chain constant domain, a linker connects the antigen recognition domain with an anchoring transmembrane domain (ATD) which is fused to an intracellular co-stimulatory signaling domain (CSD) which in turn is fused to a stimulatory signaling domain (SSD).

FIG. 2E shows the architecture of the crossFab format with CH-CL swap. Depicted is the extracellular domain comprising an antigen binding moiety which consists of an Ig heavy chain fragment and an Ig light chain wherein the CH and CL domains are exchanged. Attached to the light chain constant domain, a linker connects the antigen recognition domain with an anchoring transmembrane domain (ATD) which is fused to an intracellular co-stimulatory signaling domain (CSD) which in turn is fused to a stimulatory signaling domain (SSD).

FIG. 2F shows the architecture of the classic scFv format with an extracellular antigen recognition domain, consisting of a variable heavy and variable light chain, both connected by a linker. Attached to the variable light chain, a linker connects the antigen recognition domain with an anchoring transmembrane domain (ATD) which is fused to an intracellular co-stimulatory signaling domain (CSD) which in turn is fused to a stimulatory signaling domain (SSD).

FIG. 3A-3F depicts a schematic representation illustrating the modular composition of exemplary expression constructs encoding CARs used according to the invention.

FIG. 3A and FIG. 3B depict exemplary Fab formats.

FIG. 3C depicts an exemplary scFab format. FIG. 3D and FIG. 3E depict exemplary crossFab formats. FIG. 3F depicts a classic scFv format.

Figure 1:
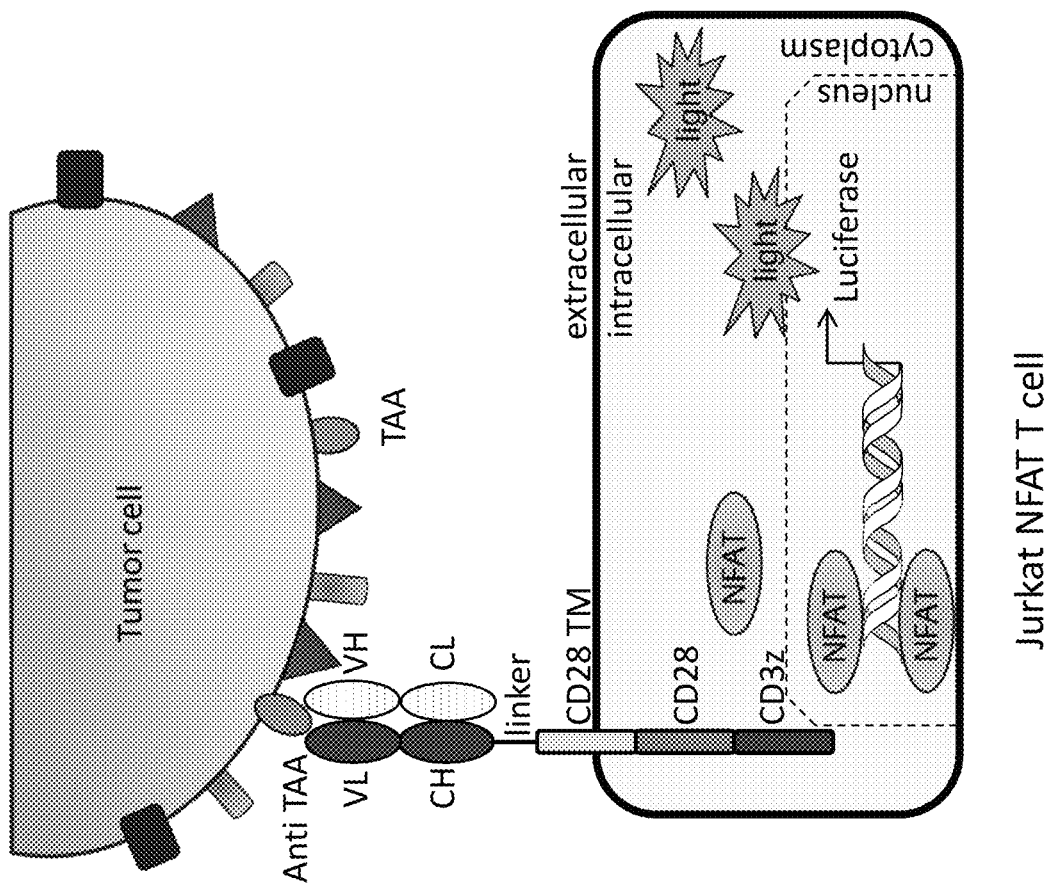
Figure 4:
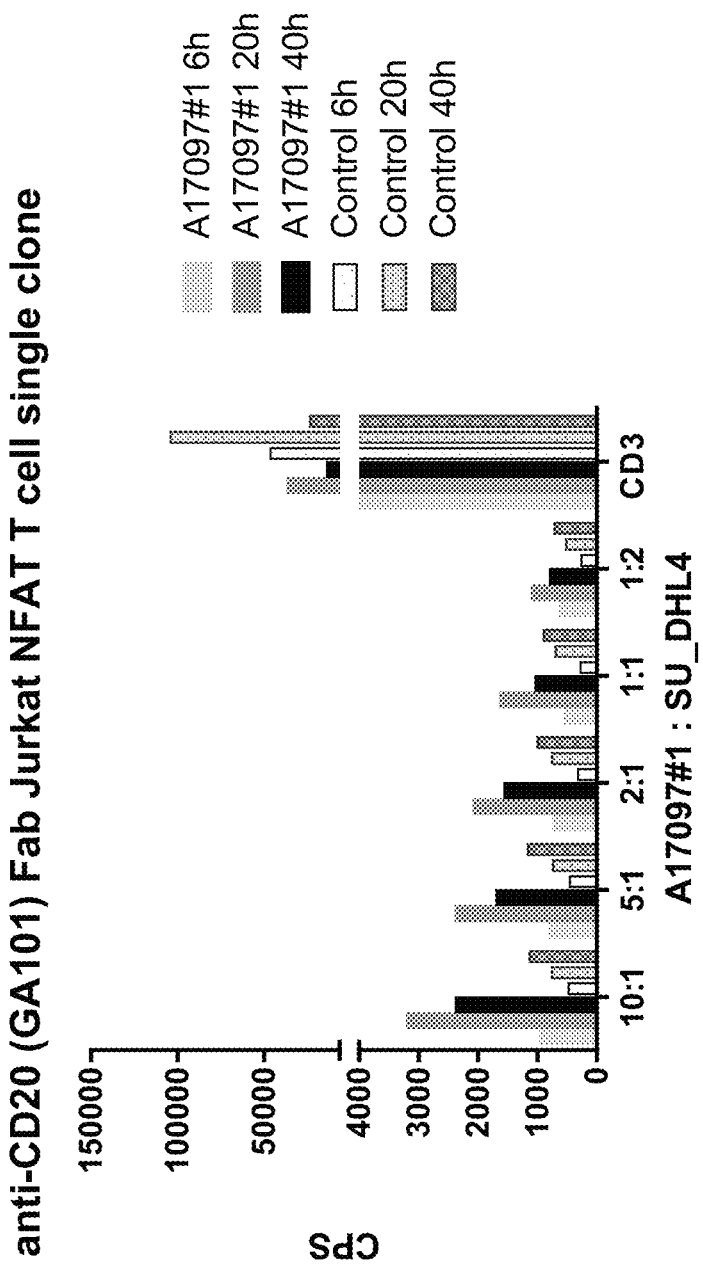

FIG. 4 depicts a Jurkat NFAT reporter CAR-T cell assay using CD20 expressing SUDHDL4 tumor cells as target cells. A single clone of anti-CD20-Fab-CD28ATD- CD28CSD-CD3zSSD expressing Jurkat NFAT reporter CAR-T cells was used as reporter cells.

Figure 5:
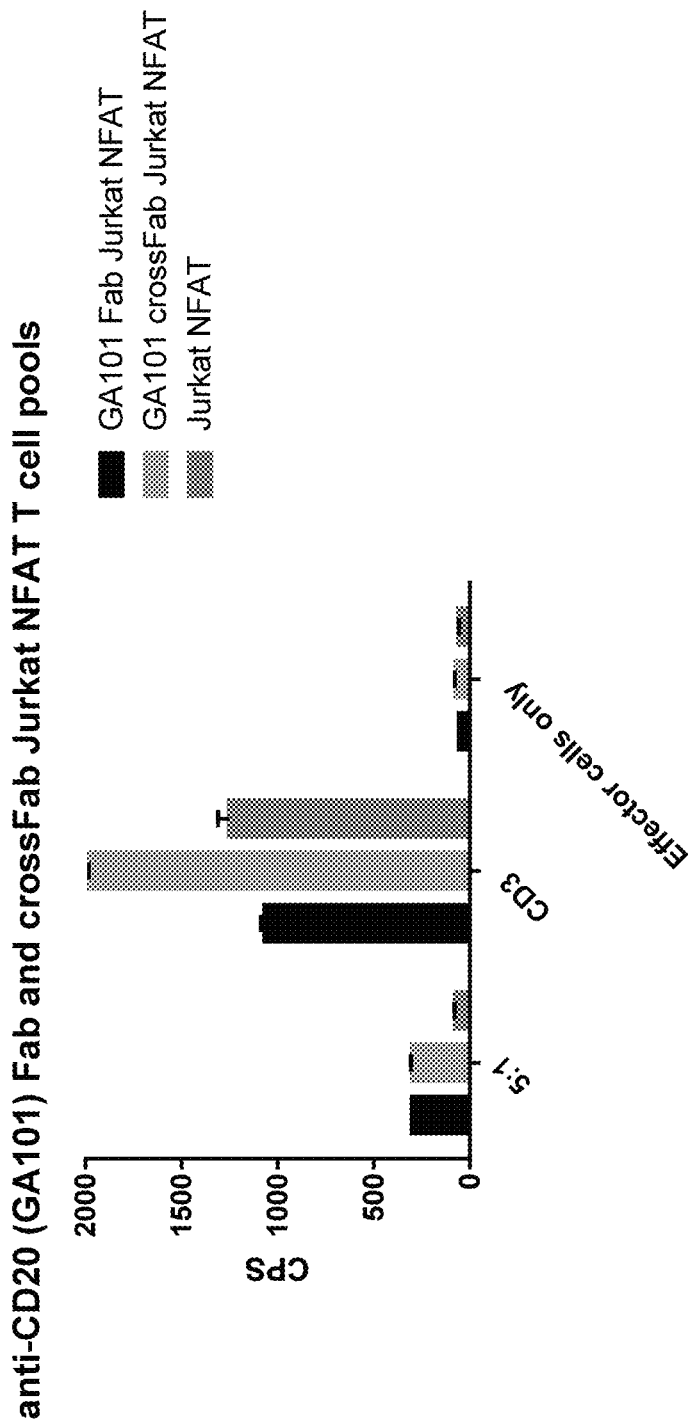

FIG. 5 depicts a Jurkat NFAT reporter CAR-T cell assay using CD20 expressing SUDHDL4 tumor cells as target cells. A pool of anti-CD20-Fab-CD28ATD-CD28CSD-CD3zSSD or anti-CD20-crossFab-CD28ATD-CD28CSD-CD3zSSD expressing Jurkat NFAT reporter CAR-T cells was used as reporter cells.

Figure 6:
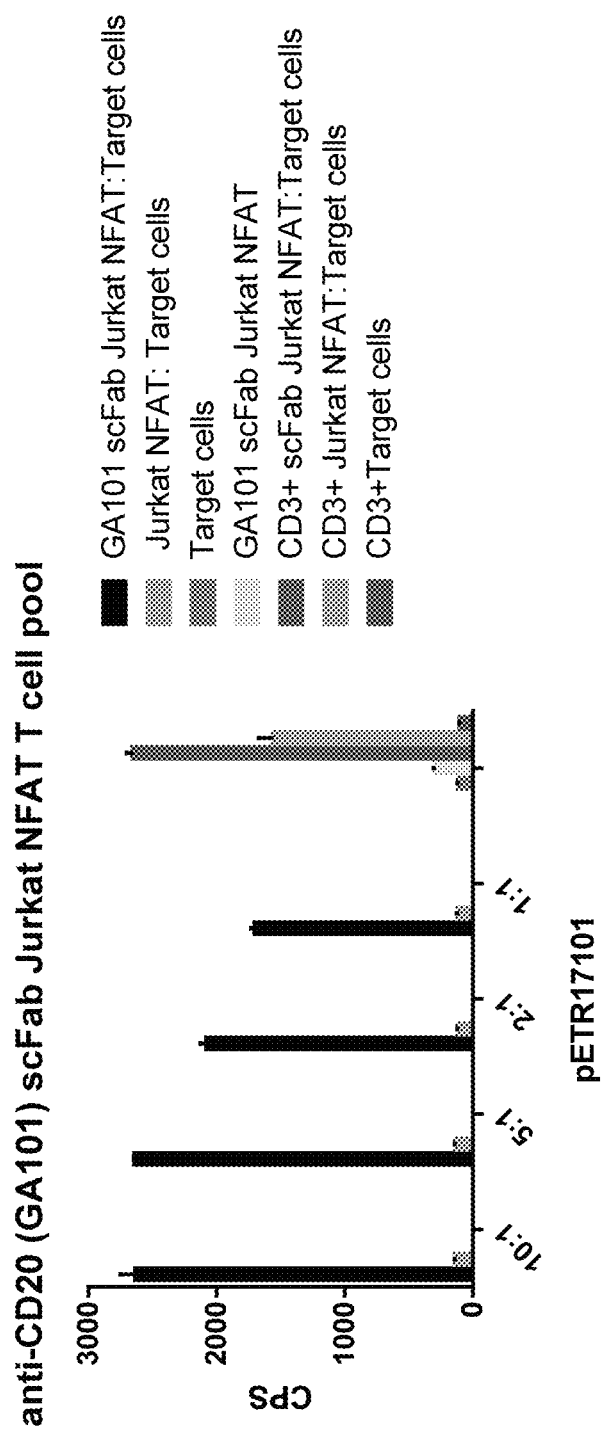

FIG. 6 depicts a Jurkat NFAT reporter CAR-T cell assay using CD20 expressing SUDHDL4 tumor cells as target cells. A pool of anti-CD20-scFab-CD28ATD-CD28CSD-CD3zSSD expressing Jurkat NFAT reporter CAR-T cells was used as reporter cells.

Figure 7:
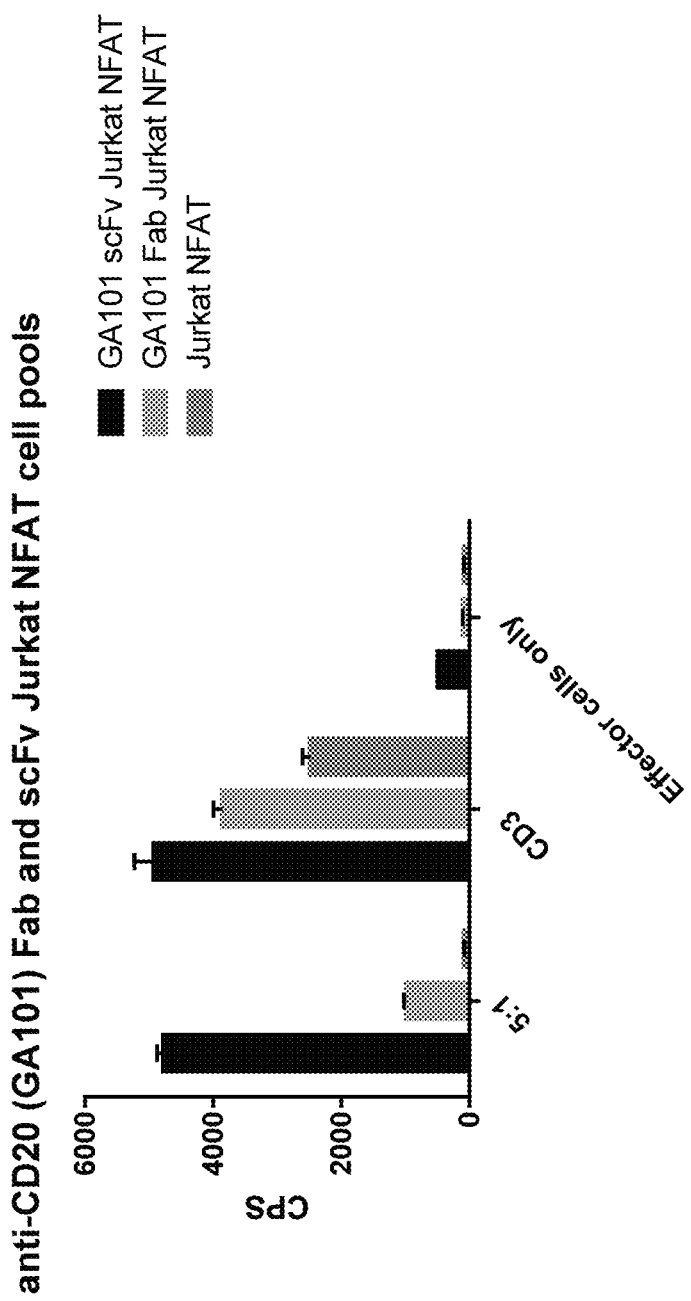

FIG. 7 depicts a Jurkat NFAT reporter CAR-T cell reporter assay using CD20 expressing SUDHDL4 tumor cells as target cells. A pool of anti-CD20-Fab-CD28ATD-CD28CSD-CD3zSSD or anti-CD20-scFv-CD28ATD-CD28CSD-CD3zSSD expressing Jurkat NFAT reporter CAR-T cells was used as reporter cells.

Figure 8A:
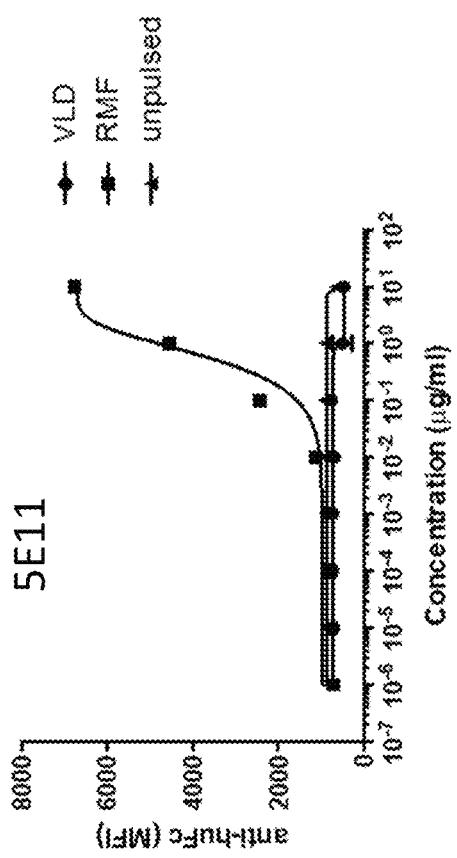
Figure 8B:
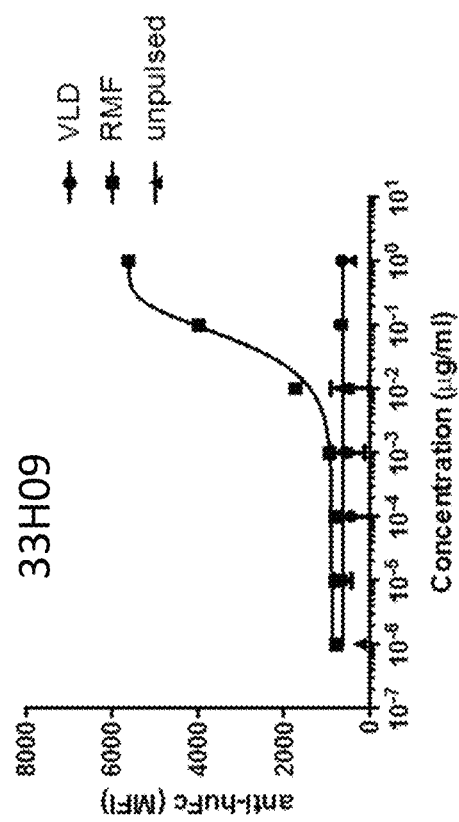

FIG. 8A and FIG. 8B depict assessment of specificity of WT1/HLA-binders 5E11 and 33H09 by FACS with T2 cells pulsed with RMF-peptide or VLD-peptide.

Figure 9:
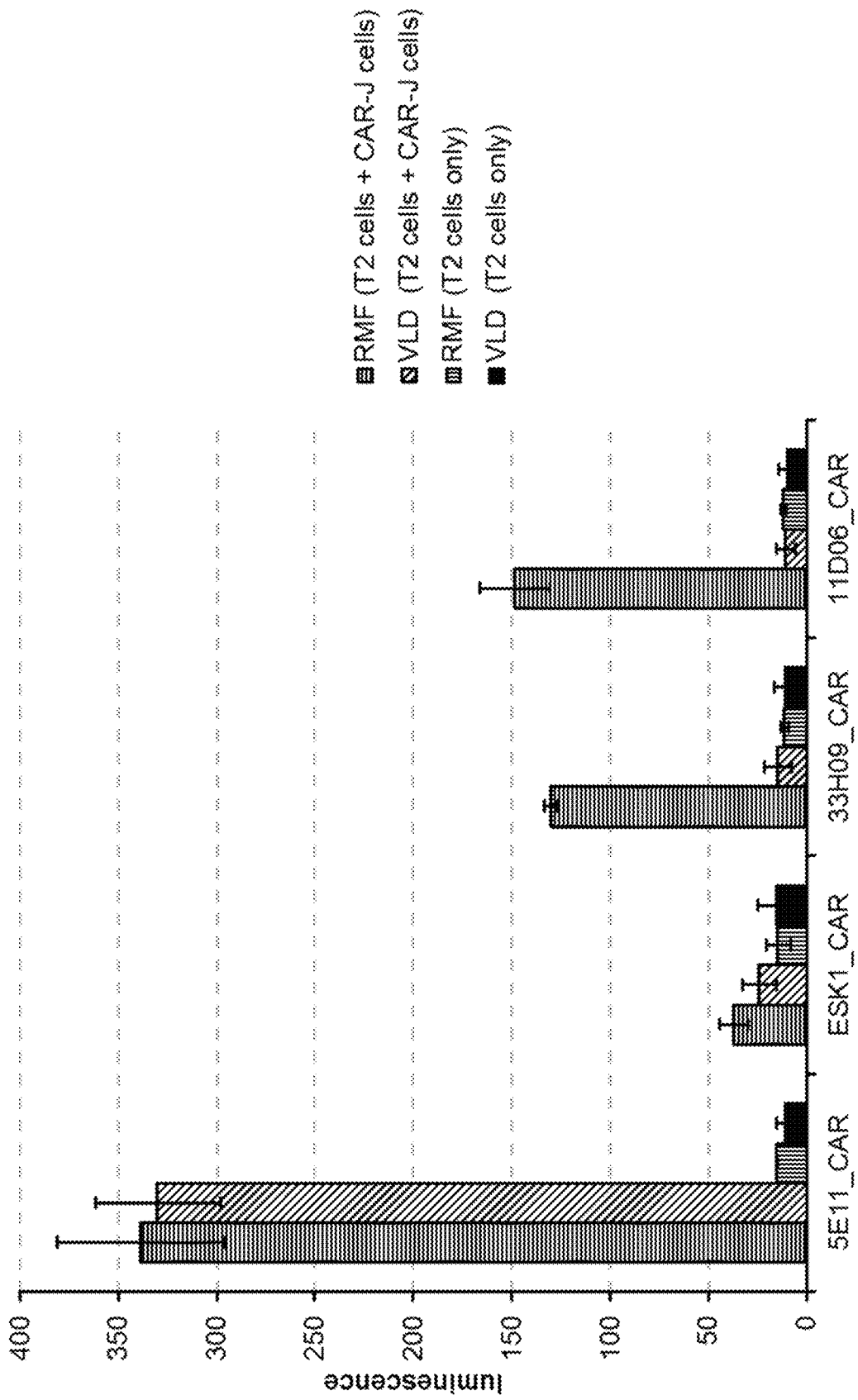

FIG. 9 depicts activation of CAR-NFAT-signaling in a Jurkat NFAT reporter anti-WT1/HLA-Fab-CAR-T cell pool upon co-incubation with RMF- or VLD-peptide-pulsed T2 cells. Comparison of signals on RMF-peptide (target) vs. VLD-peptide (off-target) helps to assess specificity of activation.

Figure 10:
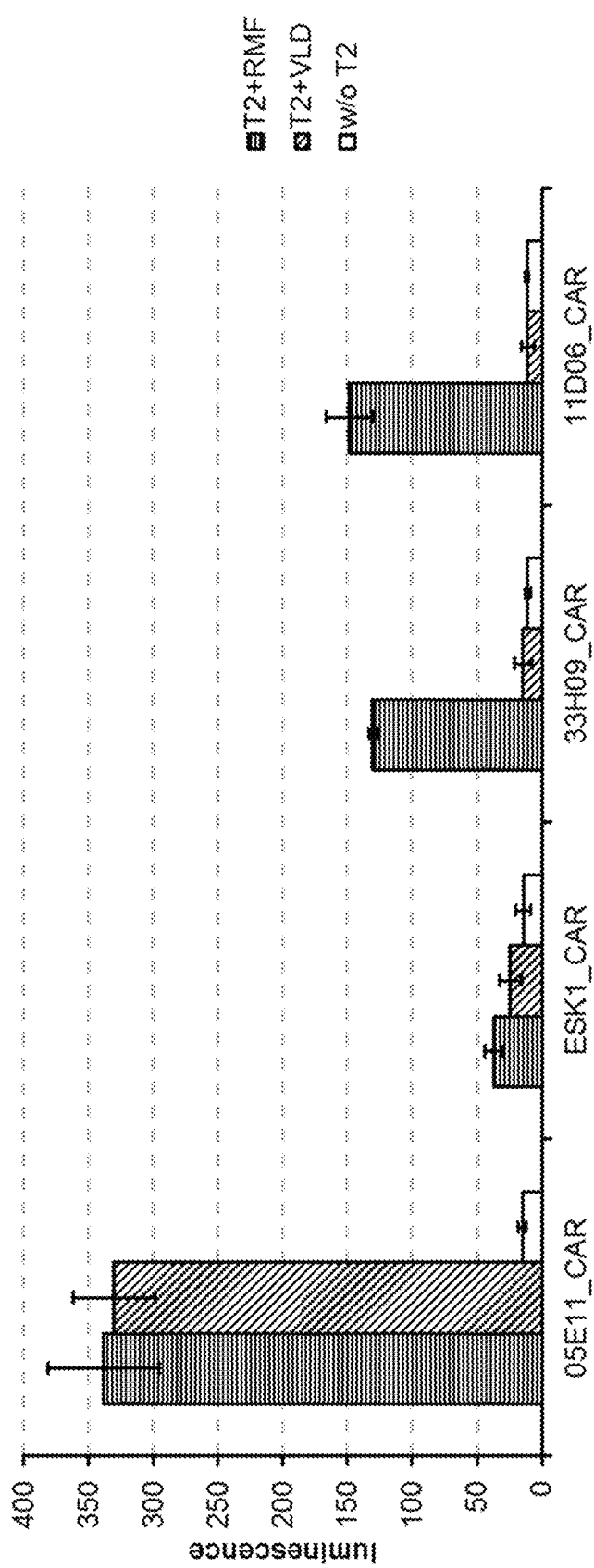

FIG. 10 depicts activation of CAR-NFAT-signaling in Jurkat NFAT reporter anti-WT1/HLA-Fab-CAR-T cell pools upon co-incubation with RMF- or VLD-peptide-pulsed T2 cells. Comparison of signals on RMF-peptide (target) vs. VLD-peptide (off-target) helps to assess specificity of activation. Signals of NFAR reporter CAR-T cell pools incubated without target cells illustrate the low background of the assay.

Figure 11:
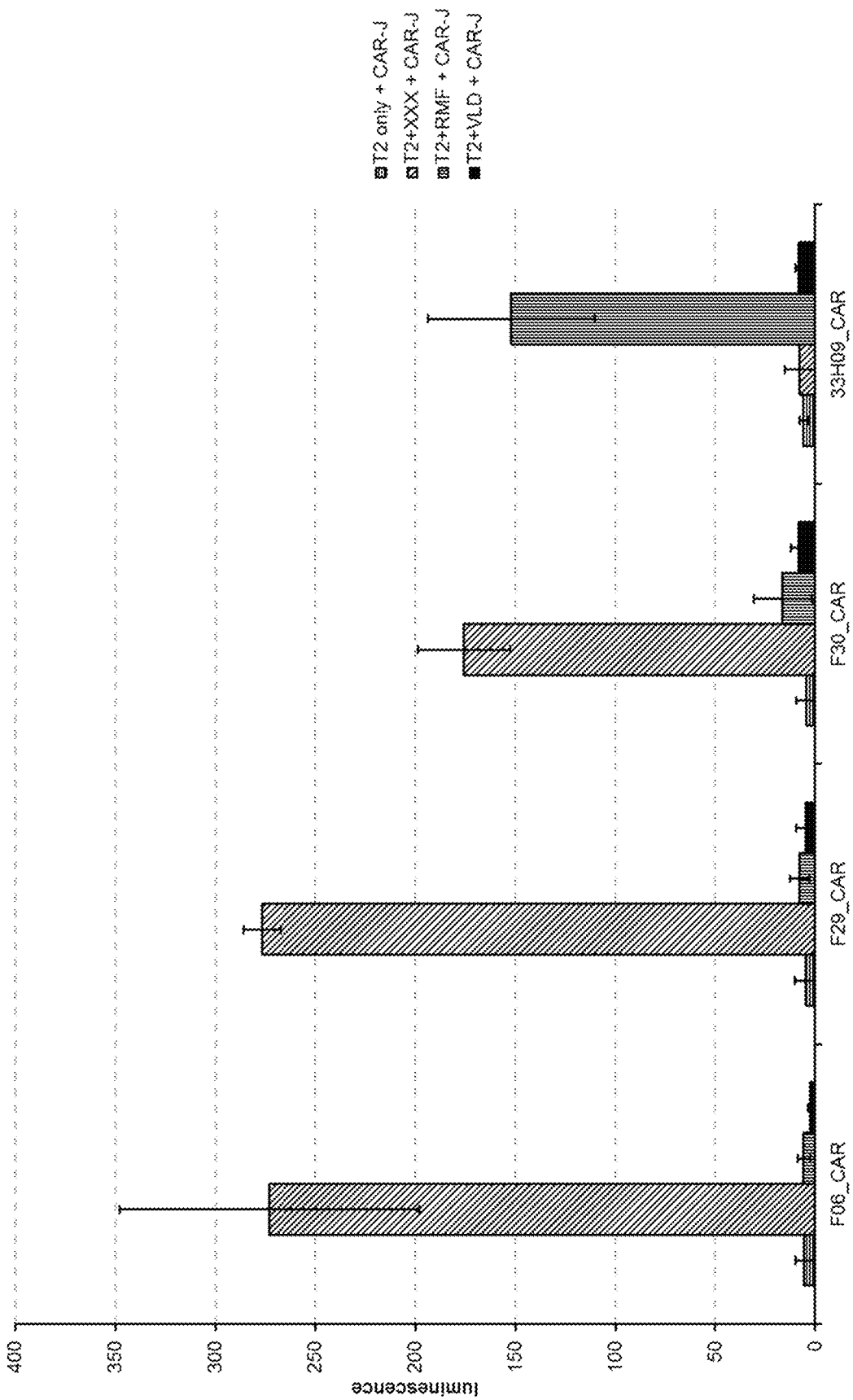

FIG. 11 depicts activation of CAR-NFAT-signaling in Jurkat NFAT Fab-CAR-T cell pools expressing CAR-binders to different peptide/HLA-targets. Jurkat NFJAT CAR-T cell pools F06, F29 and F30 bind to a blinded peptide/HLA-target with an unrelated peptide.

DETAILED DESCRIPTION

Definitions

Terms are used herein as generally used in the art, unless otherwise defined in the following.

An "activating Fc receptor" is an Fc receptor that following engagement by an Fc domain of an antibody elicits signaling events that stimulate the receptor-bearing cell to perform effector functions. Human activating Fc receptors include FcγRIIIa (CD16a), FcγRI (CD64), FcγRIIa (CD32), and FcαRI (CD89).

An "effective amount" of an agent refers to the amount that is necessary to result in a physiological change in the cell or tissue to which it is administered.

"Affinity" refers to the strength of the sum total of non-covalent interactions between a single binding site of a molecule (e.g., a receptor) and its binding partner (e.g., a ligand). Unless indicated otherwise, as used herein, "binding affinity" refers to intrinsic binding affinity which reflects a 1:1 interaction between members of a binding pair (e.g., an antigen binding moiety and an antigen and/or a receptor and its ligand). The affinity of a molecule X for its partner Y can generally be represented by the dissociation constant (KD), which is the ratio of dissociation and association rate constants ($k_{off}$ and $k_{on}$, respectively). Thus, equivalent affinities may comprise different rate constants, as long as the ratio of the rate constants remains the same. Affinity can be measured by well-established methods known in the art, including those described herein. A preferred method for measuring affinity is Surface Plasmon Resonance (SPR) and a preferred temperature for the measurement is 25° C.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, y-carboxyglutamate, and O-phosphoserine. Amino acid analogs refer to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid. Amino acids may be referred to herein by either their commonly known three letter symbols or by the one-letter symbols recommended by the IUPAC-IUB Biochemical Nomenclature Commission.

The term "amino acid mutation" as used herein is meant to encompass amino acid substitutions, deletions, insertions, and modifications. Any combination of substitution, deletion, insertion, and modification can be made to arrive at the final construct, provided that the final construct possesses the desired characteristics. Amino acid sequence deletions and insertions include amino- and/or carboxy-terminal deletions and insertions of amino acids. Particular amino acid mutations are amino acid substitutions. For the purpose of altering e.g., the binding characteristics of an antigen binding moiety, non-conservative amino acid substitutions, i.e. replacing one amino acid with another amino acid having different structural and/or chemical properties, are particularly preferred. Amino acid substitutions include replacement by non-naturally occurring amino acids or by naturally occurring amino acid derivatives of the twenty standard amino acids (e.g., 4-hydroxyproline, 3-methylhistidine, ornithine, homoserine, 5-hydroxylysine). Amino acid mutations can be generated using genetic or chemical methods well known in the art. Genetic methods may include site-directed mutagenesis, PCR, gene synthesis and the like. It is contemplated that methods of altering the side chain group of an amino acid by methods other than genetic engineering, such as chemical modification, may also be useful.

Various designations may be used herein to indicate the same amino acid mutation.

The term "antibody" herein is used in the broadest sense and encompasses various antibody structures, including but not limited to monoclonal antibodies, polyclonal antibodies, and antibody fragments so long as they exhibit the desired antigen-binding activity. Accordingly, in the context of the present invention, the term antibody relates to full immunoglobulin molecules as well as to parts of such immunoglobulin molecules. Furthermore, the term relates, as discussed herein, to modified and/or altered antibody molecules, in particular to mutated antibody molecules. The term also relates to recombinantly or synthetically generated/synthesized antibodies. In the context of the present invention the term antibody is used interchangeably with the term immunoglobulin.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$, diabodies, linear antibodies, single-chain antibody molecules (e.g., scFv), and single-domain antibodies.

For a review of certain antibody fragments, see Hudson et al., Nat Med 9, 129-134 (2003). For a review of scFv fragments, see e.g., Phickthun, in The Pharmacology of Monoclonal Antibodies, vol. 113, Rosenburg and Moore eds., Springer-Verlag, New York, pp. 269-315 (1994); see also WO 93/16185; and U.S. Pat. Nos. 5,571,894 and 5,587,458. Diabodies are antibody fragments with two antigen-binding sites that may be bivalent or bispecific. See, for example, EP 404,097; WO 1993/01161; Hudson et al., Nat Med 9, 129-134 (2003); and Hollinger et al., Proc Natl Acad Sci USA 90, 6444-6448 (1993). Triabodies and tetrabodies are also described in Hudson et al., Nat Med 9, 129-134 (2003). Single-domain antibodies are antibody fragments comprising all or a portion of the heavy chain variable domain or all or a portion of the light chain variable domain of an antibody (Domantis, Inc., Waltham, MA; see e.g., U.S. Pat. No. 6,248,516 B1). Antibody fragments can be made by various techniques, including but not limited to proteolytic digestion of an intact antibody as well as production by recombinant host cells (e.g., E. coli or phage), as described herein.

As used herein, the term "antigen binding molecule" refers in its broadest sense to a molecule that specifically binds an antigenic determinant. Examples of antigen binding molecules are immunoglobulins and derivatives, e.g., fragments, thereof as well as antigen binding receptors, e.g., CARs, and derivatives thereof.

As used herein, the term "antigen binding moiety" refers to a polypeptide molecule that specifically binds to an antigenic determinant. In one embodiment, an antigen binding moiety is able to direct the entity to which it is attached (e.g., an immunoglobulin or a CAR) to a target site, for example to a specific type of tumor cell or tumor stroma bearing the antigenic determinant. In another embodiment an antigen binding moiety is able to activate signaling through its target antigen, for example signaling is activated upon binding of an antigenic determinant to a CAR on a T cell. In the context of the present invention, antigen binding moieties may be included in antibodies and fragments thereof as well as in CARs and fragments thereof as further defined herein. Antigen binding moieties include an antigen binding domain, comprising an immunoglobulin heavy chain variable region and an immunoglobulin light chain variable region. In certain embodiments, the antigen binding moieties may comprise immunoglobulin constant regions as further defined herein and known in the art. Useful heavy chain constant regions include any of the five isotypes: $\alpha$, $\delta$, $\epsilon$, $\gamma$, or $\mu$. Useful light chain constant regions include any of the two isotypes: $\kappa$ and $\lambda$.

In the context of the present invention the term "antigen binding receptor" relates to an antigen binding molecule comprising an anchoring transmembrane domain and an extracellular domain comprising at least one antigen binding moiety. An antigen binding receptor (e.g., a CAR) can be made of polypeptide parts from different sources. Accordingly, it may be also understood as a "fusion protein" and/or a "chimeric protein". Usually, fusion proteins are proteins created through the joining of two or more genes (or preferably cDNAs) that originally coded for separate proteins. Translation of this fusion gene (or fusion cDNA) results in a single polypeptide, preferably with functional properties derived from each of the original proteins.

Recombinant fusion proteins are created artificially by recombinant DNA technology for use in biological research or therapeutics. In the context of the present invention a CAR (chimeric antigen receptor) is understood to be an antigen binding receptor comprising an extracellular portion comprising an antigen binding moiety fused by a spacer sequence to an anchoring transmembrane domain which is itself fused to the intracellular signaling domains of CD3z and CD28.

An "antigen binding site" refers to the site, i.e. one or more amino acid residues, of an antigen binding molecule which provides interaction with the antigen. For example, the antigen binding site of an antibody or a CAR comprises amino acid residues from the complementarity determining regions (CDRs). A native immunoglobulin molecule typically has two antigen binding sites, a Fab or a scFv molecule typically has a single antigen binding site.

The term "antigen binding domain" refers to the part of an antibody or an antigen binding receptor (e.g., a CAR) that comprises the area which specifically binds to and is complementary to part or all of an antigen. An antigen binding domain may be provided by, for example, one or more immunoglobulin variable domains (also called variable regions). Particularly, an antigen binding domain comprises an immunoglobulin light chain variable region (VL) and an immunoglobulin heavy chain variable region (VH).

The term "variable region" or "variable domain" refers to the domain of an immunoglobulin heavy or light chain that is involved in binding the antigen. The variable domains of the heavy chain and light chain (VH and VL, respectively) of a native antibody generally have similar structures, with each domain comprising four conserved framework regions (FRs) and three hypervariable regions (HVRs). See, e.g., Kindt et al., Kuby Immunology, 6th ed., W.H. Freeman and Co, page 91 (2007). A single VH or VL domain is usually sufficient to confer antigen-binding specificity.

The term "ATD" as used herein refers to "anchoring transmembrane domain" which defines a polypeptide stretch capable of integrating in (the) cellular membrane(s) of a cell. The ATD can be fused to further extracellular and/or intracellular polypeptide domains wherein these extracellular and/or intracellular polypeptide domains will be confined to the cell membrane as well. In the context of the antigen binding receptors as used in the present invention the ATD confers membrane attachment and confinement of the antigen binding receptor, e.g., a CAR used according to the present invention.

The term "binding to" as used in the context of the antigen binding receptors (e.g., CARs) used according to the present invention defines a binding (interaction) of an "antigen-interaction-site" and an antigen with each other. The term "antigen-interaction-site" defines a motif of a polypeptide which shows the capacity of specific interaction with a specific antigen or a specific group of antigens. Said binding/interaction is also understood to define a "specific recognition".

The term "specifically recognizing" means in accordance with this invention that the antigen binding receptor is capable of specifically interacting with and/or binding to a tumor associated antigen (TAA) molecule as defined herein. The antigen binding moiety of an antigen binding receptor (e.g., a CAR) can recognize, interact and/or bind to different epitopes on the same molecule. This term relates to the specificity of the antigen binding receptor, i.e., to its ability to discriminate between the specific regions of a molecule as defined herein. The specific interaction of the antigen-interaction-site with its specific antigen may result in an initiation of a signal, e.g., due to the induction of a change of the conformation of the polypeptide comprising the antigen, an oligomerization of the polypeptide comprising the antigen, an oligomerization of the antigen binding receptor, etc. Thus, a specific motif in the amino acid sequence of the antigen-interaction-site and the antigen bind to each other as a result of their primary, secondary or tertiary structure as well as the result of secondary modifications of said structure.

Accordingly, the term binding to does not only relate to a linear epitope but may also relate to a conformational epitope, a structural epitope or a discontinuous epitope consisting of two regions of the target molecules or parts thereof. In the context of this invention, a conformational epitope is defined by two or more discrete amino acid sequences separated in the primary sequence which comes together on the surface of the molecule when the polypeptide folds to the native protein (Sela, Science 166 (1969), 1365 and Laver, Cell 61 (1990), 553-536). Moreover, the term "binding to" is interchangeably used in the context of the present invention with the term "interacting with". The ability of the antigen binding moiety (e.g., a Fab, or scFv domain) of a CAR or an antibody to bind to a specific target antigenic determinant can be measured either through an enzyme-linked immunosorbent assay (ELISA) or other techniques familiar to one of skill in the art, e.g., surface plasmon resonance (SPR) technique (analyzed on a BIAcore instrument) (Liljeblad et al., Glyco J 17, 323-329 (2000)), and traditional binding assays (Heeley, Endocr Res 28, 217-229 (2002)). In one embodiment, the extent of binding of an antigen binding moiety to an unrelated protein is less than about 10% of the binding of the antigen binding moiety to the target antigen as measured, in particular by SPR. In certain embodiments, an antigen binding moiety that binds to the target antigen, has a dissociation constant (KD) of ≤1 µM, ≤100 nM, ≤10 nM, ≤1 nM, ≤0.1 nM, ≤0.01 nM, or ≤0.001 nM (e.g., $10^{-8}$ M or less, e.g., from $10^{-8}$ M to $10^{-13}$ M, e.g., from $10^{-9}$ M to $10^{-13}$ M). The term "specific binding" as used in accordance with the present invention means that the molecules used in the invention do not or do not essentially cross-react with (poly-) peptides of similar structures. Cross-reactivity of a panel of constructs under investigation may be tested, for example, by assessing binding of a panel of antigen binding moieties under conventional conditions (see, e.g., Harlow and Lane, Antibodies: A Laboratory Manual, Cold Spring Harbor Laboratory Press, (1988) and Using Antibodies: A Laboratory Manual, Cold Spring Harbor Laboratory Press, (1999)) to the antigen of interest as well as to unrelated antigens. Only those constructs (i.e. Fab fragments, scFvs and the like) that bind to the antigen of interest but do not or do not essentially bind to unrelated antigens are considered specific for the antigen of interest and selected for further studies in accordance with the method provided herein. These methods may comprise, inter alia, binding studies, blocking and competition studies with structurally and/or functionally closely related polypeptides. The binding studies also comprise FACS analysis, surface plasmon resonance (SPR, e.g., with BIAcore®), analytical ultracentrifugation, isothermal titration calorimetry, fluorescence anisotropy, fluorescence spectroscopy or by radiolabeled ligand binding assays.

The term "CDR" as employed herein relates to "complementary determining region", which is well known in the art. The CDRs are parts of immunoglobulins or antigen binding receptors (e.g., CARs) that determine the specificity of said molecules and make contact with a specific ligand. The CDRs are the most variable part of the molecule and contribute to the antigen binding diversity of these molecules. There are three CDR regions CDR1, CDR2 and CDR3 in each V domain. CDR-H depicts a CDR region of a variable heavy chain and CDR-L relates to a CDR region of a variable light chain. VH means the variable heavy chain and VL means the variable light chain. The CDR regions of an Ig-derived region may be determined as described in "Kabat" (Sequences of Proteins of Immunological Interest", 5th edit. NIH Publication no. 91-3242 U.S. Department of Health and Human Services (1991); Chothia J. Mol. Biol. 196 (1987), 901-917) or "Chothia" (Nature 342 (1989), 877-883).

The term "CD3z" refers to T-cell surface glycoprotein CD3 zeta chain, also known as "T-cell receptor T3 zeta chain" and "CD247".

The term "chimeric antigen receptor" or "chimeric receptor" or "CAR" refers to an antigen binding receptor constituted of an extracellular portion of an antigen binding moiety (e.g., a scFv or a Fab) fused by a spacer sequence to intracellular signaling domains (e.g., of CD3z and CD28). The term "CAR" is understood in its broadest form and comprises antigen binding receptors constituted of an extracellular portion comprising an antigen binding moiety fused to CD3z and fragment thereof and to CD28 and fragments thereof, optionally through one or several peptide linkers.

The "class" of an antibody or immunoglobulin refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and respectively.

By a "crossover Fab molecule" (also termed "crossFab" or "crossover Fab fragment") is meant a Fab molecule wherein either the variable regions or the constant regions of the Fab heavy and light chain are exchanged, i.e. the crossFab fragment comprises a peptide chain composed of the light chain variable region and the heavy chain constant region, and a peptide chain composed of the heavy chain variable region and the light chain constant region. For clarity, in a crossFab fragment wherein the variable regions of the Fab light chain and the Fab heavy chain are exchanged, the peptide chain comprising the heavy chain constant region is referred to herein as the heavy chain of the crossover Fab molecule. Conversely, in a crossFab fragment wherein the constant regions of the Fab light chain and the Fab heavy chain are exchanged, the peptide chain comprising the heavy chain variable region is referred to herein as the heavy chain of the crossFab fragment. Accordingly, a crossFab fragment comprises a heavy or light chain composed of the heavy chain variable and the light chain constant regions (VH-CL), and a heavy or light chain composed of the light chain variable and the heavy chain constant regions (VL-CH1).

In contrast thereto, by a "Fab" or "conventional Fab" molecule is meant a Fab molecule in its natural format, i.e. comprising a heavy chain composed of the heavy chain variable and constant regions (VH-CH1), and a light chain composed of the light chain variable and constant regions (VL-CL).

The term "CSD" as used herein refers to co-stimulatory signaling domain.

The term "effector functions" refers to those biological activities attributable to the Fc region of an antibody, which vary with the antibody isotype. Examples of antibody effector functions include: C1q binding and complement dependent cytotoxicity (CDC), Fc receptor binding, antibody-dependent cell-mediated cytotoxicity (ADCC), antibody-dependent cellular phagocytosis (ADCP), cytokine secretion, immune complex-mediated antigen uptake by antigen presenting cells, down regulation of cell surface receptors (e.g., B cell receptor), and B cell activation.

As used herein, the terms "engineer", "engineered", "engineering", are considered to include any manipulation of the peptide backbone or the post-translational modifications of a naturally occurring or recombinant polypeptide or fragment thereof. Engineering includes modifications of the amino acid sequence, of the glycosylation pattern, or of the side chain group of individual amino acids, as well as combinations of these approaches.

The term "expression cassette" refers to a polynucleotide generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment.

Typically, the recombinant expression cassette portion of an expression vector includes, among other sequences, a nucleic acid sequence to be transcribed and a promoter.

A "Fab molecule" refers to a protein consisting of the VH and CH1 domain of the heavy chain (the "Fab heavy chain") and the VL and CL domain of the light chain (the "Fab light chain") of an antigen binding molecule.

The term "Fc domain" or "Fc region" herein is used to define a C-terminal region of an immunoglobulin heavy chain that contains at least a portion of the constant region. The term includes native sequence Fc regions and variant Fc regions. Although the boundaries of the Fc region of an IgG heavy chain might vary slightly, the human IgG heavy chain Fc region is usually defined to extend from Cys226, or from Pro230, to the carboxyl-terminus of the heavy chain. However, the C-terminal lysine (Lys447) of the Fc region may or may not be present.

Unless otherwise specified herein, numbering of amino acid residues in the Fc region or constant region is according to the "EU numbering" system, also called the EU index, as described in Kabat et al., Sequences of Proteins of Immunological Interest, 5th Ed. Public Health Service, National Institutes of Health, Bethesda, Md., 1991. A subunit of an Fc domain as used herein refers to one of the two polypeptides forming the dimeric Fc domain, i.e. a polypeptide comprising C-terminal constant regions of an immunoglobulin heavy chain, capable of stable self-association. For example, a subunit of an IgG Fc domain comprises an IgG CH2 and an IgG CH3 constant domain.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The term "full length antibody" denotes an antibody consisting of two "full length antibody heavy chains" and two "full length antibody light chains". A "full length antibody heavy chain" is a polypeptide consisting in N-terminal to C-terminal direction of an antibody heavy chain variable domain (VH), an antibody constant heavy chain domain 1 (CH1), an antibody hinge region (HR), an antibody heavy chain constant domain 2 (CH2), and an antibody heavy chain constant domain 3 (CH3), abbreviated as VH-CH1-HR-CH2-CH3; and optionally an antibody heavy chain constant domain 4 (CH4) in case of an antibody of the subclass IgE. Preferably the "full length antibody heavy chain" is a polypeptide consisting in N-terminal to C-terminal direction of VH, CH1, HR, CH2 and CH3. A "full length antibody light chain" is a polypeptide consisting in N-terminal to C-terminal direction of an antibody light chain variable domain (VL), and an antibody light chain constant domain (CL), abbreviated as VL-CL. The antibody light chain constant domain (CL) can be κ (kappa) or λ (lambda). The two full length antibody chains are linked together via inter-polypeptide disulfide bonds between the CL domain and the CH1 domain and between the hinge regions of the full length antibody heavy chains. Examples of typical full length antibodies are natural antibodies like IgG (e.g., IgG 1 and IgG2), IgM, IgA, IgD, and IgE)

By "fused" is meant that the components (e.g., a Fab and a transmembrane domain) are linked by peptide bonds, either directly or via one or more peptide linkers.

The terms "host cell", "host cell line" and "host cell culture" are used interchangeably and refer to cells into which exogenous nucleic acid has been introduced, including the progeny of such cells. Host cells include "transformants" and "transformed cells" which include the primary transformed cell and progeny derived therefrom without regard to the number of passages.

Progeny may not be completely identical in nucleic acid content to a parent cell, but may contain mutations. Mutant progeny that have the same function or biological activity as screened or selected for in the originally transformed cell are included herein. Host cells include cultured cells, e.g., mammalian cultured cells, such as CHO cells, BHK cells, NSO cells, SP2/0 cells, YO myeloma cells, P3X63 mouse myeloma cells, PER cells, PER.C6 cells or hybridoma cells, yeast cells, insect cells, and plant cells, to name only a few, but also cells comprised within a transgenic animal, transgenic plant or cultured plant or animal tissue.

The term "hypervariable region" or "HVR", as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the complementarity determining regions (CDRs), the latter being of highest sequence variability and/or involved in antigen recognition. With the exception of CDR1 in VH, CDRs generally comprise the amino acid residues that form the hypervariable loops. Hypervariable regions (HVRs) are also referred to as complementarity determining regions (CDRs), and these terms are used herein interchangeably in reference to portions of the variable region that form the antigen binding regions. This particular region has been described by Kabat et al., U.S. Dept. of Health and Human Services, Sequences of Proteins of Immunological Interest (1983) and by Chothia et al., J Mol Biol 196:901-917 (1987), where the definitions include overlapping or subsets of amino acid residues when compared against each other. Nevertheless, application of either definition to refer to a CDR of an antibody and/or an antigen binding receptor or variants thereof is intended to be within the scope of the term as defined and used herein. The appropriate amino acid residues which encompass the CDRs as defined by each of the above cited references are set forth below in Table 1 as a comparison. The exact residue numbers which encompass a particular CDR will vary depending on the sequence and size of the CDR. Those skilled in the art can routinely determine which residues comprise a particular CDR given the variable region amino acid sequence of the antibody.

TABLE 1

CDR Definitions[1]

| CDR | Kabat | Chothia | AbM[2] |
|---|---|---|---|
| $V_H$ CDR1 | 31-35 | 26-32 | 26-35 |
| $V_H$ CDR2 | 50-65 | 52-58 | 50-58 |
| $V_H$ CDR3 | 95-102 | 95-102 | 95-102 |
| $V_L$ CDR1 | 24-34 | 26-32 | 24-34 |
| $V_L$ CDR2 | 50-56 | 50-52 | 50-56 |
| $V_L$ CDR3 | 89-97 | 91-96 | 89-97 |

[1]Numbering of all CDR definitions in TABLE 1 is according to the numbering conventions set forth by Kabat et al. (see below).
[2]"AbM" with a lowercase "b" as used in TABLE 1 refers to the CDRs as defined by Oxford Molecular's "AbM" antibody modeling software.

Kabat et al. also defined a numbering system for variable region sequences that is applicable to any antibody. One of ordinary skill in the art can unambiguously assign this system of Kabat numbering to any variable region sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in an antigen binding moiety variable region are according to the Kabat numbering system. The polypeptide sequences of the sequence listing are not numbered according to the Kabat numbering system. However, it is well within the ordinary skill of one in the art to convert the numbering of the sequences of the Sequence Listing to Kabat numbering.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). Particularly, the individual or subject is a human.

By "isolated nucleic acid" molecule or polynucleotide is intended a nucleic acid molecule, DNA or RNA, which has been removed from its native environment. For example, a recombinant polynucleotide encoding a polypeptide contained in a vector is considered isolated for the purposes of the present invention. Further examples of an isolated polynucleotide include recombinant polynucleotides maintained in heterologous host cells or purified (partially or substantially) polynucleotides in solution. An isolated polynucleotide includes a polynucleotide molecule contained in cells that ordinarily contain the polynucleotide molecule, but the polynucleotide molecule is present extrachromosomally or at a chromosomal location that is different from its natural chromosomal location. Isolated RNA molecules include in vivo or in vitro RNA transcripts of the present invention, as well as positive and negative strand forms, and double-stranded forms. Isolated polynucleotides or nucleic acids according to the present invention further include such molecules produced synthetically. In addition, a polynucleotide or a nucleic acid may be or may include a regulatory element such as a promoter, ribosome binding site, or a transcription terminator.

By a nucleic acid or polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These alterations of the reference sequence may occur at the 5' or 3' terminal positions of the reference nucleotide sequence or anywhere between those terminal positions, interspersed either individually among residues in the reference sequence or in one or more contiguous groups within the reference sequence. As a practical matter, whether any particular polynucleotide sequence is at least 80%, 85%, 90%, 95%, 96%, 97%, 98% or 99% identical to a nucleotide sequence of the present invention can be determined conventionally using known computer programs, such as the ones discussed below for polypeptides (e.g., ALIGN-2).

By an "isolated polypeptide" or a variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for the purpose of the invention, as are native or recombinant polypeptides which have been separated, fractionated, or partially or substantially purified by any suitable technique.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "nucleic acid molecule" relates to the sequence of bases comprising purine- and pyrimidine bases which are comprised by polynucleotides, whereby said bases represent the primary structure of a nucleic acid molecule. Herein, the term nucleic acid molecule includes DNA, cDNA, genomic DNA, RNA, synthetic forms of DNA and mixed polymers comprising two or more of these molecules. In addition, the term nucleic acid molecule includes both, sense and antisense strands. Moreover, the herein described nucleic acid molecule may contain non-natural or derivatized nucleotide bases, as will be readily appreciated by those skilled in the art.

As used herein "NFAT" refers to the "nuclear factor of activated T-cells" and is a family of transcription factors which is expressed in most immune cells. Activation of transcription factors of the NFAT family is dependent on calcium signaling. As an example, T cell activation through the T cell synapse results in calcium influx. Increased intracellular calcium levels activate the calcium-sensitive phosphatase, calcineurin, which rapidly dephosphorylates the serine-rich region (SRR) and SP-repeats in the amino termini of NFAT proteins. This results in a conformational change that exposes a nuclear localization signal promoting NFAT nuclear import and activation of target genes.

As used herein "NFAT pathway" refers to the stimuli that lead to modulation of activity of member of the NFAT family of transcription factors. NFAT DNA elements are known in the art and are herein also referred to as "response element of the NFAT pathway". Hence, a "receptor of the NFAT pathway" refers to a receptor which can trigger the modulation of activity of NFAT: Examples of a "receptor of the NFAT pathway" are e.g., T cell receptor and B cell receptor.

As used herein "NF-κB" refers to the "nuclear factor kappa-light-chain-enhancer of activated B cells" and is a transcription factor which is implicated in the regulation of many genes that code for mediators of apoptosis, viral replication, tumorigenesis, various autoimmune diseases and inflammatory responses. NFκB is present in almost all eukaryotic cells. Generally, it is located in the cytosol in an inactive state, since it forms a complex with inhibitory kappa B (IκB) proteins. Through the binding of ligands to integral membrane receptors (also referred to as "receptors of the NF-κB pathway", the IκB kinase (IKK) is activated. IKK is an enzyme complex which consists of two kinases and a regulatory subunit. This complex phosphorylates the IκB proteins, which leads to ubiquitination and therefore degradation of those proteins by the proteasome. Finally, the free NFκB is in an active state, translocates to the nucleus and binds to the κB DNA elements and induces transcription of target genes.

As used herein "NF-κB pathway" refers to the stimuli that lead to modulation of activity of NF-κB. For example activation of the Toll-like receptor signaling, TNF receptor signaling, T cell receptor and B cell receptor signaling through either binding of a ligand or an antibody result in activation of NF-κB. Subsequently, phosphorylated dimers bind to κB DNA elements and induce transcription of target genes. κB DNA elements are known in the art and herein also referred to as "response element of the NF-κB pathway". Hence, a "receptor of the NF-κB pathway" refers to a receptor which can trigger the modulation of activity of NF-κB: Examples of a "receptor of the NF-κB pathway" are Toll-like receptors, TNF receptors, T cell receptor and B cell receptor.

As used herein "AP-1" refers to the "activator protein 1" and is a transcription factor which is involved in a number of cellular processes including differentiation, proliferation, and apoptosis. AP-1 functions are dependent on the specific Fos and Jun subunits contributing to AP-1 dimers. AP-1 binds to a palindromic DNA motif (5'-TGA G/C TCA-3') to regulate gene expression.

The term "pharmaceutical composition" refers to a preparation which is in such form as to permit the biological activity of an active ingredient contained therein to be effective, and which contains no additional components which are unacceptably toxic to a subject to which the formulation would be administered. A pharmaceutical composition usually comprises one or more pharmaceutically acceptable carrier(s).

A "pharmaceutically acceptable carrier" refers to an ingredient in a pharmaceutical composition, other than an active ingredient, which is nontoxic to a subject. A pharmaceutically acceptable carrier includes, but is not limited to, a buffer, excipient, stabilizer, or preservative.

As used herein, the term "polypeptide" refers to a molecule composed of monomers (amino acids) linearly linked by amide bonds (also known as peptide bonds). The term polypeptide refers to any chain of two or more amino acids, and does not refer to a specific length of the product. Thus, peptides, dipeptides, tripeptides, oligopeptides, protein, amino acid chain, or any other term used to refer to a chain of two or more amino acids, are included within the definition of polypeptide, and the term polypeptide may be used instead of, or interchangeably with any of these terms. The term polypeptide is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis. A polypeptide of the invention may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to as unfolded.

The term "polynucleotide" refers to an isolated nucleic acid molecule or construct, e.g., messenger RNA (mRNA), virally-derived RNA, or plasmid DNA (pDNA). A polynucleotide may comprise a conventional phosphodiester bond or a non-conventional bond (e.g., an amide bond, such as found in peptide nucleic acids (PNA). The term nucleic acid molecule refers to any one or more nucleic acid segments, e.g., DNA or RNA fragments, present in a polynucleotide.

The term "protein with intrinsic fluorescence" refers to a protein capable of forming a highly fluorescent, intrinsic chromophore either through the cyclization and oxidation of internal amino acids within the protein or via the enzymatic addition of a fluorescent co-factor. The term "protein with intrinsic fluorescence" includes wild-type fluorescent proteins and mutants that exhibit altered spectral or physical properties. The term does not include proteins that exhibit weak fluorescence by virtue only of the fluorescence contribution of non-modified tyrosine, tryptophan, histidine and phenylalanine groups within the protein. Proteins with intrinsic fluorescence are known in the art, e.g., green fluorescent protein (GFP),), red fluorescent protein (RFP), Blue fluorescent protein (BFP, Heim et al. 1994, 1996), a cyan fluorescent variant known as CFP (Heim et al. 1996; Tsien 1998); a yellow fluorescent variant known as YFP (Ormo et al. 1996; Wachter et al. 1998); a violet-excitable green fluorescent variant known as Sapphire (Tsien 1998; Zapata-Hommer et al. 2003); and a cyan-excitable green fluorescing variant known as enhanced green fluorescent protein or EGFP (Yang et al. 1996) and can be measured e.g., by live cell imaging (e.g., Incucyte) or fluorescent spectrophotometry. "Reduced binding" refers to a decrease in affinity for the respective interaction, as measured for example by SPR. For clarity the term includes also reduction of the affinity to zero (or below the detection limit of the analytic method), i.e. complete abolishment of the interaction.

Conversely, "increased binding" refers to an increase in binding affinity for the respective interaction.

The term "regulatory sequence" refers to DNA sequences, which are necessary to effect the expression of coding sequences to which they are ligated. The nature of such control sequences differs depending upon the organism. In prokaryotes, control sequences generally include promoter, ribosomal binding site, and terminators. In eukaryotes generally control sequences include promoters, terminators and, in some instances, enhancers, transactivators or transcription factors. The term "control sequence" is intended to include, at a minimum, all components the presence of which are necessary for expression, and may also include additional advantageous components.

As used herein, a "reporter gene" means a gene whose expression can be assayed. In one preferred embodiment a "reporter gene" is a gene that encodes a protein the production and detection of which is used as a surrogate to detect indirectly the activity of the antibody or ligand to be tested. The reporter protein is the protein encoded by the reporter gene. Preferably, the reporter gene encodes an enzyme whose catalytic activity can be detected by a simple assay method or a protein with a property such as intrinsic fluorescence or luminescence so that expression of the reporter gene can be detected in a simple and rapid assay requiring minimal sample preparation. Non-limiting examples of enzymes whose catalytic activity can be detected are Luciferase, beta Galactosidase, Alkaline Phosphatase. Luciferase is a monomeric enzyme with a molecular weight (MW) of 61 kDa. It acts as a catalysator and is able to convert D-luciferin in the presence of Adenosine triphosphate (ATP) and $Mg^{2+}$ to luciferyl adenylate. In addition, pyrophosphate (PPi) and adenosine monophosphate (AMP) are generated as byproducts. The intermediate luciferyl adenylate is then oxidized to oxyluciferin, carbon dioxide ($CO_2$) and light. Oxyluciferin is a bioluminescent product which can be quantitatively measured in a luminometer by the light released from the reaction. Luciferase reporter assays are commercially available and known in the art, e.g., Luciferase 1000 Assay System and ONE-Glo™ Luciferase Assay System.

A "response element" refers to a specific transcription factor binding element, or cis acting element which can be activated or silenced on binding of a certain transcription factor. In one embodiment the response element is a cis-acting enhancer element located upstream of a minimal promotor (e.g., a TATA box promotor) which drives expression of the reporter gene upon transcription factor binding.

As used herein, the term "single-chain" refers to a molecule comprising amino acid monomers linearly linked by peptide bonds. In certain embodiments, one of the antigen binding moieties is a scFv fragment, i.e. a VH domain and a VL domain connected by a peptide linker. In certain embodiments, one of the antigen binding moieties is a single-chain Fab molecule, i.e. a Fab molecule wherein the Fab light chain and the Fab heavy chain are connected by a peptide linker to form a single peptide chain. In a particular such embodiment, the C-terminus of the Fab light chain is connected to the N-terminus of the Fab heavy chain in the single-chain Fab molecule.

The term "SSD" as used herein refers to stimulatory signaling domain.

As used herein, "treatment" (and grammatical variations thereof such as "treat" or "treating") refers to clinical intervention in an attempt to alter the natural course of a disease in the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis.

As used herein, the term "target antigenic determinant" is synonymous with "target antigen", "target epitope", "tumor associated antigen" and "target cell antigen" and refers to a site (e.g., a contiguous stretch of amino acids or a conformational configuration made up of different regions of non-contiguous amino acids) on a polypeptide macromolecule to which an antibody binds, forming an antigen binding moiety-antigen complex. Useful antigenic determinants can be found, for example, on the surfaces of tumor cells, on the surfaces of virus-infected cells, on the surfaces of other diseased cells, on the surface of immune cells, free in blood serum, and/or in the extracellular matrix (ECM). The proteins referred to as antigens herein (e.g., CD20, CEA, FAP, TNC) can be any native form of the proteins from any vertebrate source, including mammals such as primates (e.g., humans) and rodents (e.g., mice and rats), unless otherwise indicated. In a particular embodiment the target antigen is a human protein. Where reference is made to a specific target protein herein, the term encompasses the "full-length", unprocessed target protein as well as any form of the target protein that results from processing in the target cell. The term also encompasses naturally occurring variants of the target protein, e.g., splice variants or allelic variants. Exemplary human target proteins useful as antigens include, but are not limited to: CD20, CEA, FAP, TNC, MSLN, FolR1, HER1 and HER2. The ability of an antigen binding receptor, e.g., a CAR, to bind to a specific target antigenic determinant can be measured either through an enzyme-linked immunosorbent assay (ELISA) or other techniques familiar to one of skill in the art, e.g., surface plasmon resonance (SPR) technique (analyzed on a BIAcore instrument) (Liljeblad et al., Glyco J 17, 323-329 (2000)), and traditional binding assays (Heeley, Endocr Res 28, 217-229 (2002)). In one embodiment, the extent of binding of the antigen binding receptor to an unrelated protein is less than about 10% of the binding of the antibody to the target antigen as measured, e.g., by SPR. In certain embodiments, the antigen binding receptro binds to the target antigen with an affinity dissociation constant (KD) of ≤1 µM, ≤100 nM, ≤10 nM, ≤1 nM, ≤0.1 nM, ≤0.01 nM, or ≤0.001 nM (e.g., $10^{-8}$ M or less, e.g., from $10^{-8}$ M to $10^{-13}$ M, e.g., from $10^{-9}$ M to $10^{-13}$ M). "T cell activation" as used herein refers to one or more cellular response of a T lymphocyte, particularly a cytotoxic T lymphocyte, selected from: proliferation, differentiation, cytokine secretion, cytotoxic effector molecule release, cytotoxic activity, and expression of activation markers. Suitable assays to measure T cell activation are known in the art described herein.

In accordance with this invention, the term "T cell receptor" or "TCR" is commonly known in the art. In particular, herein the term "T cell receptor" refers to any T cell receptor, provided that the following three criteria are fulfilled: (i) tumor specificity, (ii) recognition of (most) tumor cells, which means that an antigen or target should be expressed in (most) tumor cells and (iii) that the TCR matches to the HLA-type of the subjected to be treated. In this context, suitable T cell receptors which fulfill the above mentioned three criteria are known in the art such as receptors recognizing NY-ESO-1 (for sequence information(s) see, e.g., PCT/GB2005/001924) and/or HER2neu (for sequence information(s) see WO-A1 2011/0280894).

A "therapeutically effective amount" of an agent, e.g., a pharmaceutical composition, refers to an amount effective, at dosages and for periods of time necessary, to achieve the desired therapeutic or prophylactic result. A therapeutically effective amount of an agent for example eliminates, decreases, delays, minimizes or prevents adverse effects of a disease.

The term "vector" or "expression vector" is synonymous with "expression construct" and refers to a DNA molecule that is used to introduce and direct the expression of a specific gene to which it is operably associated in a target cell. The term includes the vector as a self-replicating nucleic acid structure as well as the vector incorporated into the genome of a host cell into which it has been introduced. The expression vector of the present invention comprises an expression cassette. Expression vectors allow transcription of large amounts of stable mRNA.

Once the expression vector is inside the target cell, the ribonucleic acid molecule or protein that is encoded by the gene is produced by the cellular transcription and/or translation machinery.

In one embodiment, the expression vector of the invention comprises an expression cassette that comprises polynucleotide sequences that encode antigen binding receptors of the invention or fragments thereof.

Provided herein are methods for selecting novel antigen binding moieties for further development according to their specificity, in particular in relation to activation of reporter cells (e.g., T cells) upon contact to a target cell. In this context the novel antigen binding moiety mediates the contact between a target cell, in particular a cancer cell, and an reporter cell, in particular a T cell. In one embodiment, provided is a method for assessing the specificity of an antigen binding moiety comprising the steps of:

a) providing an antigen binding moiety specific for a target antigen;
b) generating a chimeric antigen receptor (CAR) expressing reporter T (CAR-T) cell by:
 i. transferring the antigen binding moiety into a CAR vector system operationally coupled to a response element; and
 ii. transferring the CAR vector system into a reporter T cell comprising a reporter gene under the control of the response element
c) contacting the reporter CAR-T cell with a target cell comprising the target antigen on the surface, in particular wherein the target cell is a cancer cell; and
d) determining T cell activation by determining the expression of the reporter gene to establish the specificity of the antigen binding moiety.

Immunoglobulins typically comprise variable and constant domain capable of stable folding wherein the variable domains confer the specificity of the immunoglobulin molecule towards a target antigen. The specificity of a candidate antigen binding moiety, e.g., towards a target antigen on a tumor cell, can be transferred to a different antigen binding molecule, e.g., a CAR, by transferring the variable domains of the candidate antigen binding moiety. This transfer is known in the art and for example can be done by sub-cloning the coding regions for the candidate antigen binding moiety into a different DNA vector system, e.g., a CAR vector system as described herein. Towards this end, appropriate recombinant DNA techniques are widely used in the art, transfer from one vector system to another vector system is straight-forward.

However, it might be suitable to transfer the variable domains of an antigen binder, e.g., an immunoglobulin, particularly VH and VL domains, into the antigen binding moiety of an antigen binding receptor comprising a similar antigen binding format (e.g., Fab to Fab, crossFab or scFab) to preserve binding characteristics and to generate a meaningful assay system.

Accordingly, provided herein are methods using different CAR formats (e.g., scFv, Fab, crossFab and scFab; scFv to scFv) which can be selected according to the format of the source immunoglobulin. After the transfer of the VH and VL domains into the CAR vector system, cells transfected or transduced with the CAR vector system become reactive against the target antigen, e.g., against the target antigen on a tumor cell. Activation of CAR vector system upon binding of the antigen binding moiety of the CAR to the target antigen on a tumor cell will result in activation of a reporter gene, which can be assayed.

This approach bears significant advantages over conventional binding assays since the T cell based system as described herein, without being bound by theory, more closely resembles the in vivo situation encountered for or with, e.g., therapeutic antibodies engaging T cells (e.g., T cell bispecific antibodies).

Accordingly, the invention provides a versatile screening platform wherein engineered CARs comprising an antigen binding moiety may be used to assay novel antigen binding moieties to target cells (e.g., tumor cells). After binding to the target antigen on the surface of a tumor cell (e.g., a tumor associated antigen), the T cell becomes activated wherein the activation can be measured, e.g., by read-out of a fluorescent or luminescent signal. The platform is flexible and specific by allowing the use of diverse newly developed target antigen binding moieties.

In the context of the present invention, the CAR comprises an extracellular domain that does not naturally occur in or on T cells. Thus, the CAR is capable of providing tailored binding specificity to the recognition domain, e.g., a target antigen of a tumor cell, according to the methods as described herein for assessing the binding and functionality of novel antigen binding moieties. Cells, e.g., T cells, transduced with a CAR and used according to the invention become capable of specific binding to the target antigen, i.e. specificity for the target antigen domain is provided by the antigen binding moiety of the extracellular domain of the CAR.

In this context, antigen binding receptors, e.g., CARs are provided comprising an anchoring transmembrane domain and an extracellular domain comprising an antigen binding moiety, wherein the antigen binding moiety is a Fab, crossFab or a scFab fragment.

In certain embodiments, the antigen binding moiety is a Fab fragment, in particular a Fab fragment deriving from a phage display library screening. In this context, the antigen binding moiety of the CAR vector system, preferably, is also a Fab fragment. In such an embodiment, preferably, the CAR comprises an antigen binding moiety, in particular wherein the antigen binding moiety of the CAR is a Fab fragment. In one embodiment, the antigen binding moiety comprises a variable heavy chain domain (VH) and a variable light chain domain (VL). In one embodiment, the VH and VL domains of the antigen binding moiety are transferred to the CAR.

Accordingly, in one embodiment, at least one of the antigen binding moieties is a conventional Fab fragment, i.e. a Fab molecule consisting of a Fab light chain and a Fab heavy chain. In one embodiment, at least one of the antigen binding moieties is a crossFab fragment, i.e. a Fab molecule consisting of a Fab light chain and a Fab heavy chain, wherein either the variable regions or the constant regions of the Fab heavy and light chain are exchanged. In one embodiment, at least one of the antigen binding moieties is a scFv fragment. In a particular embodiment, the C-terminus of the variable heavy chain (VH) is connected to the N-terminus of the variable light chain (VL) in the scFv molecule, optionally through a peptide linker. In certain embodiments, at least one of the antigen binding moieties is a single-chain Fab molecule, i.e. a Fab molecule wherein the Fab light chain and the Fab heavy chain are connected by a peptide linker to form a single peptide chain. In a particular such embodiment, the C-terminus of the Fab light chain is connected to the N-terminus of the Fab heavy chain in the single-chain Fab molecule, optionally through a peptide linker.

Antigen binding moieties capable of specific binding to a target antigen, e.g., a tumor associated antigen, may be generated by immunization of, e.g., a mammalian immune system. Such methods are known in the art and, e.g., are described in Burns in Methods in Molecular Biology 295: 1-12 (2005). Alternatively, antigen binding moieties of the invention may be isolated by screening combinatorial libraries for antibodies with the desired activity or activities. Methods for screening combinatorial libraries are reviewed, e.g., in Lerner et al. in Nature Reviews 16:498-508 (2016).

For example, a variety of methods are known in the art for generating phage display libraries and screening such libraries for antigen binding moieties possessing the desired binding characteristics. Such methods are reviewed, e.g., in Frenzel et al. in mAbs 8:1177-1194 (2016); Bazan et al. in Human Vaccines and Immunotherapeutics 8:1817-1828 (2012) and Zhao et al. in Critical Reviews in Biotechnology 36:276-289 (2016) as well as in Hoogenboom et al. in Methods in Molecular Biology 178:1-37 (O'Brien et al., ed., Human Press, Totowa, NJ, 2001) and further described, e.g., in the McCafferty et al., Nature 348:552-554; Clackson et al., Nature 352: 624-628 (1991); Marks et al., J. Mol. Biol. 222: 581-597 (1992) and in Marks and Bradbury in Methods in Molecular Biology 248:161-175 (Lo, ed., Human Press, Totowa, NJ, 2003).; Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132(2004). In certain phage display methods, repertoires of VH and VL genes are separately cloned by polymerase chain reaction (PCR) and recombined randomly in phage libraries, which can then be screened for antigen-binding phage as described in Winter et al. in Annual Review of Immunology 12: 433-455 (1994). Phage typically display antibody fragments, either as single-chain Fv (scFv) fragments or as Fab fragments. Libraries from immunized sources provide high-affinity antigen binding moieties to the immunogen without the requirement of constructing hybridomas. Alternatively, the naive repertoire can be cloned (e.g., from human) to provide a single source of antigen binding moieties to a wide range of non-self and also self antigens without any immunization as described by Griffiths et al. in EMBO Journal 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter in Journal of Molecular Biology 227: 381-388 (1992). Patent publications describing human antibody phage libraries include, for example: U.S. Pat. Nos. 5,750,373; 7,985,840; 7,785,903 and 8,679,490 as well as US Patent Publication Nos. 2005/0079574, 2007/0117126, 2007/0237764 and 2007/0292936. and 2009/0002360. Further examples of methods known in the art for screening combinatorial libraries for antigen binding moieties with a desired activity or activities include ribosome and mRNA display, as well as methods for antibody display and selection on bacteria, mammalian cells, insect cells or yeast cells. Methods for yeast surface display are reviewed, e.g., in Scholler et al. in Methods in Molecular Biology 503:135-56 (2012) and in Cherf et al. in Methods in Molecular biology 1319:155-175 (2015) as well as in the Zhao et al. in Methods in Molecular Biology 889:73-84 (2012). Methods for ribosome display are described, e.g., in He et al. in Nucleic Acids Research 25:5132-5134 (1997) and in Hanes et al. in PNAS 94:4937-4942 (1997). A particular advantage of the method of the invention is the straight-forward integration and characterization of a library derived antigen binding moiety without changing the format, e.g., a Fab antigen binder deriving from screening a phage display library can be included in the Fab and/or crossFab format as described herein. Accordingly, antigen binding moieties deriving from Fab displaying phage libraries can be included in an antigen binding receptor, e.g., a CAR, herein described without changing the format to, e.g., a scFv format which might affect the binding properties of the library derived binder.

In the context of the present invention, provided herein are CARs comprising an antigen binding moiety capable of specific binding to a target antigen, i.e. a tumor associated antigen.

Accordingly, transduced cells, i.e. T cells, expressing a CAR as described herein are capable of specific binding to the tumor cell.

In an illustrative embodiment of the present invention, as a proof of concept, provided are CARs capable of specific binding CD20 and reporter cells expressing said antigen binding receptors.

The target cell is one which expresses a CD20 polypeptide and is of a cell type which specifically expresses or overexpresses a CD20 polypeptide. The cells may be cancerous or normal cells of the particular cell type. The cell may be a normal B cell involved in autoimmunity. In one embodiment the cell is a cancer cell, preferably a malignant B cell. Other tumor associated antigens can be targeted with CARs as described herein.

Accordingly, in one specific embodiment the extracellular domain of the CAR comprises an antigen binding moiety capable of specific binding to CD20, wherein the antigen binding moiety comprises:
(i) a heavy chain variable region (VH) comprising
  (a) the heavy chain complementarity-determining region (CDR H) 1 amino acid sequence YSWIN (SEQ ID NO:1);
  (b) the CDR H2 amino acid sequence RIFPGDGDTDYNGKFKG (SEQ ID NO:2); and
  (c) the CDR H3 amino acid sequence NVFDGYWLVY (SEQ ID NO:3); and
(ii) a light chain variable region (VL) comprising
  (d) the light chain complementary-determining region (CDR L) 1 amino acid sequence RSSKSLLHSNGITYLY (SEQ ID NO:4);
  (e) the CDR L2 amino acid sequence QMSNLVS (SEQ ID NO:5); and
  (f) the CDR L3 amino acid sequence AQNLELPYT (SEQ ID NO:6).

In one embodiment the extracellular domain of the CAR comprises an antigen binding moiety capable of specific binding to CD20, wherein the antigen binding moiety comprises a heavy chain variable region (VH) comprising an amino acid sequence that is at least about 95%, 96%, 97%, 98%, 99% or 100% identical to the amino acid of SEQ ID NO:12, and a light chain variable region (VL) comprising an amino acid sequence that is at least about 95%, 96%, 97%, 98%, 99% or 100% identical to the amino acid sequence of SEQ ID NO:10.

In one embodiment the extracellular domain of the CAR comprises an antigen binding moiety capable of specific binding CD20, wherein the antigen binding moiety comprises the heavy chain variable region (VH) of SEQ ID NO:12 and the light chain variable region (VL) of SEQ ID NO:10.

In one embodiment, the antigen binding moiety is a Fab, a crossFab or a scFab fragment.

In one preferred embodiment the extracellular domain of the CAR comprises an antigen binding moiety capable of specific binding to CD20, wherein the antigen binding moiety is a Fab fragment.

In one embodiment, the extracellular domain of the CAR comprises an antigen binding moiety capable of specific binding to CD20, wherein the Fab fragment comprising a heavy chain of SEQ ID NO:8 and a light chain of SEQ ID NO:9.

In one embodiment the antigen binding moiety of the CAR is a scFv fragment which is a polypeptide consisting of an heavy chain variable domain (VH), an light chain variable domain (VL) and a linker, wherein said variable domains and said linker have one of the following configurations in N-terminal to C-terminal direction: a) VH-linker-VL or b) VL-linker-VH. In a preferred embodiment, the scFv fragment has the configuration VH-linker-VL.

In certain embodiments, the CARs as used herein comprise an extracellular domain comprising an antigen binding moiety capable of specific binding to the target antigen, an anchoring transmembrane domain and at least one intracellular signaling and/or at least one co-stimulatory signaling domain. Accordingly, in one embodiment, the CAR vector system used according to the invention encodes a CAR comprising an antigen binding moiety, an anchoring transmembrane domain and at least one intracellular signaling and/or co-signaling domain. The anchoring transmembrane domain of the CAR may be characterized by not having a cleavage site for mammalian proteases. Proteases refer to proteolytic enzymes that are able to hydrolyze the amino acid sequence of a transmembrane domain comprising a cleavage site for the protease. The term proteases include both endopeptidases and exopeptidases. In the context of the present invention any anchoring transmembrane domain of a transmembrane protein as laid down among others by the CD-nomenclature may be used to generate the CARs used according to the invention, which activate T cells, preferably CD8+ T cells, upon binding to an antigen as defined herein.

Accordingly, in the context of the present invention, the anchoring transmembrane domain may comprise part of a murine/mouse or preferably of a human transmembrane domain. An example for such an anchoring transmembrane domain is a transmembrane domain of CD28, for example, having the amino acid sequence as shown herein in SEQ ID NO:14 (as encoded by the DNA sequence shown in SEQ ID NO:29). In the context of the present invention, the transmembrane domain of the CAR may comprise/consist of an amino acid sequence as shown in SEQ ID NO:14 (as encoded by the DNA sequence shown in SEQ ID NO:29).

In an illustrative embodiment of the present invention, as a proof of concept, an CAR is provided comprising an amino acid sequence of SEQ ID NO:7 (as encoded by the DNA sequence shown in SEQ ID NO:22), and comprising a fragment/polypeptide part of CD28 (the Uniprot Entry number of the human CD28 is P10747 (with the version number 173 and version 1 of the sequence)) as shown herein as SEQ ID NO:73 (as encoded by the DNA sequence shown in SEQ ID NO:72). Alternatively, any protein having a transmembrane domain, as provided among others by the CD nomenclature, may be used as an anchoring transmembrane domain of the antigen binding receptor protein of the invention. As described above, the herein provided CAR may comprise the anchoring transmembrane domain of CD28 which is located at amino acids 153 to 179, 154 to 179, 155 to 179, 156 to 179, 157 to 179, 158 to 179, 159 to 179, 160 to 179, 161 to 179, 162 to 179, 163 to 179, 164 to 179, 165 to 179, 166 to 179, 167 to 179, 168 to 179, 169 to 179, 170 to 179, 171 to 179, 172 to 179, 173 to 179, 174 to 179, 175 to 179, 176 to 179, 177 to 179 or 178 to 179 of the human full length CD28 protein as shown in SEQ ID NO:69 (as encoded by the cDNA shown in SEQ ID NO:68). Accordingly, in context of the present invention the anchoring transmembrane domain may comprise or consist of an amino acid sequence as shown in SEQ ID NO:14 (as encoded by the DNA sequence shown in SEQ ID NO:29).

As described herein, the CAR used according to the invention comprises at least one stimulatory signaling domain and/or at least one co-stimulatory signaling domain to transduce the binding of the antigen binding moiety of the CAR to its target antigen to an intracellular signal in the CAR-T cell. Accordingly, the herein described CAR preferably comprises a stimulatory signaling domain, which provides T cell activation. The herein described CAR may comprise a stimulatory signaling domain which is a fragment/polypeptide part of murine/mouse or human CD3z (the UniProt Entry of the human CD3z is P20963 (version number 177 with sequence number 2; the UniProt Entry of the murine/mouse CD3z is P24161 (primary citable accession number) or Q9D3G3 (secondary citable accession number) with the version number 143 and the sequence number 1)), FCGR3A (the UniProt Entry of the human FCGR3A is P08637 (version number 178 with sequence number 2)), or NKG2D (the UniProt Entry of the human NKG2D is P26718 (version number 151 with sequence number 1); the UniProt Entry of the murine/mouse NKG2D is 054709 (version number 132 with sequence number 2)).

Thus, the stimulatory signaling domain which is comprised in the herein described CAR may be a fragment/polypeptide part of the full length of CD3z, FCGR3A or NKG2D. The amino acid sequence of the murine/mouse full length of CD3z is shown herein as SEQ ID NO:70 (murine/mouse as encoded by the DNA sequence shown in SEQ ID NO:71). The amino acid sequences of the human full length CD3z is shown herein as SEQ ID NO:68 (human as encoded by the DNA sequence shown in SEQ ID NO:69). The CAR used according to the present invention may comprise fragments of CD3z, FCGR3A or NKG2D as stimulatory domain, provided that at least one signaling domain is comprised. In particular, any part/fragment of CD3z, FCGR3A, or NKG2D is suitable as stimulatory domain as long as at least one signaling motive is comprised. However, more preferably, the CAR of the present invention comprises polypeptides which are derived from human origin. Preferably, the described CAR comprises the amino acid sequences as shown herein as SEQ ID NO:68 (CD3z) (human as encoded by the DNA sequences shown in SEQ ID NO:69). For example, the fragment/polypeptide part of the human CD3z which may be comprised in the CAR used according to the present invention may comprise or consist of the amino acid sequence shown in SEQ ID NO:16 (as encoded by the DNA sequence shown in SEQ ID NO:31). Accordingly, in one embodiment the CAR comprises the sequence as shown in SEQ ID NO:16 or a sequence which has up to 1, 2, 3, 4, 5, 6, 7, 8, 9, 10, 11, 12, 13, 14, 15, 16, 17, 18, 19, 20, 21, 22, 23, 23, 24, 25, 26, 27, 28, 29 or 30 substitutions, deletions or insertions in comparison to SEQ ID NO:16 and which is characterized by having a stimulatory signaling activity. Specific configurations of CARs comprising a stimulatory signaling domain (SSD) are provided herein below and in the Examples and Figures. The stimulatory signaling activity can be determined; e.g., by enhanced cytokine release, as measured by ELISA (IL-2, IFNγ, TNFα), enhanced proliferative activity (as measured by enhanced cell numbers), or enhanced lytic activity as measured by LDH release assays.

The CAR used according to the present invention preferably comprises at least one co-stimulatory signaling domain which provides additional activity to the T cell. The herein described CAR may comprise a co-stimulatory signaling domain which is a fragment/polypeptide part of murine/mouse or human CD28 (the UniProt Entry of the human CD28 is P10747 (version number 173 with sequence number 1); the UniProt Entry of the murine/mouse CD28 is P31041 (version number 134 with sequence number 2)), CD137 (the UniProt Entry of the human CD137 is Q07011 (version number 145 with sequence number 1); the UniProt Entry of murine/mouse CD137 is P20334 (version number 139 with sequence number 1)), OX40 (the UniProt Entry of the human OX40 is P23510 (version number 138 with sequence number 1); the UniProt Entry of murine/mouse OX40 is P43488 (version number 119 with sequence number 1)), ICOS (the UniProt Entry of the human ICOS is Q9Y6W8 (version number 126 with sequence number 1)); the UniProt Entry of the murine/mouse ICOS is Q9WV40 (primary citable accession number) or Q9JL17 (secondary citable accession number) with the version number 102 and sequence version 2)), CD27 (the UniProt Entry of the human CD27 is P26842 (version number 160 with sequence number 2); the Uniprot Entry of the murine/mouse CD27 is P41272 (version number 137 with sequence version 1)), 4-1-BB (the UniProt Entry of the murine/mouse 4-1-BB is P20334 (version number 140 with sequence version 1); the UniProt Entry of the human 4-1-BB is Q07011 (version number 146 with sequence version)), DAP10 (the UniProt Entry of the human DAP10 is Q9UBJ5 (version number 25 with sequence number 1); the UniProt entry of the murine/mouse DAP10 is Q9QUJO (primary citable accession number) or Q9R1E7 (secondary citable accession number) with the version number 101 and the sequence number 1)) or DAP12 (the UniProt Entry of the human DAP12 is O43914 (version number 146 and the sequence number 1); the UniProt entry of the murine/mouse DAP12 is 0054885 (primary citable accession number) or Q9R1E7 (secondary citable accession number) with the version number 123 and the sequence number 1). In certain embodiments of the present invention the CAR used according to the present invention may comprise one or more, i.e. 1, 2, 3, 4, 5, 6 or 7 of the herein defined co-stimulatory signaling domains. Accordingly, in the context of the present invention, the CAR may comprise a fragment/polypeptide part of a murine/mouse or preferably of a human CD28 as first co-stimulatory signaling domain and the second co-stimulatory signaling domain is selected from the group consisting of the murine/mouse or preferably of the human CD27, CD28, CD137, OX40, ICOS, DAP10 and DAP12, or fragments thereof. Preferably, the CAR used according to the invention comprises a co-stimulatory signaling domain which is derived from a human origin. Thus, more preferably, the co-stimulatory signaling domain(s) which is (are) comprised in the CAR may comprise or consist of the amino acid sequence as shown in SEQ ID NO:15 (as encoded by the DNA sequence shown in SEQ ID NO:30).

Thus, the co-stimulatory signaling domain which may be optionally comprised in the herein described CAR is a fragment/polypeptide part of the full length CD27, CD28, CD137, OX40, ICOS, DAP10 and DAP12. The amino acid sequence of the murine/mouse full length CD28 is shown herein as SEQ ID NO:75 (murine/mouse as encoded by the DNA sequences shown in SEQ ID NO:74). However, because human sequences are most preferred in the context of the present invention, the co-stimulatory signaling domain which may be optionally comprised in the herein described CAR is a fragment/polypeptide part of the human full length CD27, CD28, CD137, OX40, ICOS, DAP10 or DAP12. The amino acid sequence of the human full length CD28 is shown herein as SEQ ID NO:73 (human as encoded by the DNA sequence shown in SEQ ID NO:72).

In one preferred embodiment, the CAR comprises CD28 or a fragment thereof as co-stimulatory signaling domain.

The herein described CAR may comprise a fragment of CD28 as co-stimulatory signaling domain, provided that at least one signaling domain of CD28 is comprised. In particular, any part/fragment of CD28 is suitable for the CAR as described herein as long as at least one of the signaling motives of CD28 is comprised. For example, the CD28 polypeptide which is comprised in the CAR used according to the present invention may comprise or consist of the amino acid sequence shown in SEQ ID NO:15 (as encoded by the DNA sequence shown in SEQ ID NO:30). The intracellular domain of CD28, which functions as a co-stimulatory signaling domain, may comprise a sequence derived from the intracellular domain of the CD28 polypeptide having the sequence(s) YMNM (SEQ ID NO:76) and/or PYAP (SEQ ID NO:77). Preferably, the CAR comprises polypeptides which are derived from human origin. For example, the fragment/polypeptide part of the human CD28 which may be comprised in the CAR may comprise or consist of the amino acid sequence shown in SEQ ID NO:15 (as encoded by the DNA sequence shown in SEQ ID NO:30). Accordingly, in one embodiment, the CAR comprises the sequence as shown in SEQ ID NO:15 or a sequence which has up to 1, 2, 3, 4, 5, 6, 7, 8, 9 or 10 substitutions, deletions or insertions in comparison to SEQ ID NO:15 and which is characterized by having a co-stimulatory signaling activity. Specific configurations of CARs comprising a co-stimulatory signaling domain (CSD) are provided herein below and in the Examples and Figures. The co-stimulatory signaling activity can be determined; e.g., by enhanced cytokine release, as measured by ELISA (IL-2, IFNγ, TNFα), enhanced proliferative activity (as measured by enhanced cell numbers), or enhanced lytic activity as measured by LDH release assays.

As mentioned above, in an embodiment of the present invention, the co-stimulatory signaling domain of the CAR may be derived from the human CD28 gene (Uni Prot Entry No: P10747 (accession number with the entry version: 173 and version 1 of the sequence)) and provides CD28 activity, defined as cytokine production, proliferation and lytic activity of the transduced cell described herein, like a transduced T cell. CD28 activity can be measured by release of cytokines by ELISA or flow cytometry of cytokines such as interferon-gamma (IFN-γ) or interleukin 2 (IL-2), proliferation of T cells measured, e.g., by ki67-measurement, cell quantification by flow cytometry, or lytic activity as assessed by real time impedance measurement of the target cell (by using, e.g., an ICELLligence instrument as described, e.g., in Thakur et al., Biosens Bioelectron. 35(1) (2012), 503-506; Krutzik et al., Methods Mol Biol. 699 (2011), 179-202; Ekkens et al., Infect Immun. 75(5) (2007), 2291-2296; Ge et al., Proc Natl Acad Sci USA. 99(5) (2002), 2983-2988; Düwell et al., Cell Death Differ. 21(12) (2014), 1825-1837, Erratum in: Cell Death Differ. 21(12) (2014), 161). The co-stimulatory signaling domains PYAP and YMNM are beneficial for the function of the CD28 polypeptide and the functional effects enumerated above. The amino acid sequence of the YMNM domain is shown in SEQ ID NO:76; the amino acid sequence of the PYAP domain is shown in SEQ ID NO:77.

Accordingly, in the antigen binding receptor of the present invention, the CD28 polypeptide preferably comprises a sequence derived from intracellular domain of a CD28 polypeptide having the sequences YMNM (SEQ ID NO:76) and/or PYAP (SEQ ID NO:77). These signaling motives may be present at any site within the intracellular domain of the described CARs.

Moreover, the herein described CAR may comprise at least one linker (or "spacer"). A linker is usually a peptide having a length of up to 20 amino acids. Accordingly, in the context of the present invention the linker may have a length of 1, 2, 3, 4, 5, 6, 7, 8, 9, 10, 11, 12, 13, 14, 15, 16, 17, 18, 19 or 20 amino acids. For example, the herein described CAR may comprise a linker between the extracellular domain comprising the antigen binding moiety, the anchoring transmembrane domain, the co-stimulatory signaling domain and/or the stimulatory signaling domain. Such linkers have the advantage that they increase the probability that the different polypeptides of the CAR (i.e. the extracellular domain, the anchoring transmembrane domain, the co-stimulatory signaling domain and/or the stimulatory signaling domain) fold independently and behave as expected. Thus, in the context of the present invention, the extracellular domain comprising at least one antigen binding moiety, the anchoring transmembrane domain that does not have a cleavage site for mammalian proteases, the co-stimulatory signaling domain and the stimulatory signaling domain may be comprised in a single-chain multi-functional polypeptide chain. A fusion construct, e.g., may consist of (a) polypeptide(s) comprising (an) extracellular domain(s) comprising at least one antigen binding moiety, (an) anchoring transmembrane domain(s), (a) co-stimulatory signaling domain(s) and/or (a) stimulatory signaling domain(s). In preferred embodiments, the CAR comprises an antigen binding moiety which is not a single chain construct, i.e. the antigen binding moiety is a Fab or a crossFab fragment. Preferably such constructs will comprise a single chain heavy or light chain fusion polypeptide combined with an immunoglobulin light or heavy chain as described herein, e.g., a heavy chain fusion polypeptide comprises (an) immunoglobulin heavy chain(s), (an) anchoring transmembrane domain(s), (a) co-stimulatory signaling domain(s) and/or (a) stimulatory signaling domain(s) and is combined with (an) immunoglobulin light chain(s), or a light chain fusion polypeptide comprises (an) immunoglobulin light chain(s), (an) anchoring transmembrane domain(s), (a) co-stimulatory signaling domain(s) and/or (a) stimulatory signaling domain(s) and is combined with (an) immunoglobulin heavy chain(s).

Accordingly, the antigen binding moiety, the anchoring transmembrane domain, the co-stimulatory signaling domain and the stimulatory signaling domain may be connected by one or more identical or different peptide linker as described herein. For example, in the herein described CAR the linker between the extracellular domain comprising the antigen binding moiety and the anchoring transmembrane domain may comprise or consist of the amino and amino acid sequence as shown in SEQ ID NO:20. Accordingly, the anchoring transmembrane domain, the co-stimulatory signaling domain and/or the stimulatory domain may be connected to each other by peptide linkers or alternatively, by direct fusion of the domains.

In some embodiments the antigen binding moiety comprised in the extracellular domain is a single-chain variable fragment (scFv) which is a fusion protein of the variable regions of the heavy (VH) and light chains (VL) of an antibody, connected with a short linker peptide of ten to about 25 amino acids. The linker is usually rich in glycine for flexibility, as well as serine or threonine for solubility, and can either connect the N-terminus of the VH with the C-terminus of the VL, or vice versa. For example, the linker may have the amino and amino acid sequence as shown in SEQ ID NO:19.

In some embodiments according to the invention the antigen binding moiety comprised in the extracellular domain is a single chain Fab fragment or scFab which is a polypeptide consisting of an heavy chain variable domain (VH), an antibody constant domain 1 (CH1), an antibody light chain variable domain (VL), an antibody light chain constant domain (CL) and a linker, wherein said antibody domains and said linker have one of the following orders in N-terminal to C-terminal direction: a) VH-CH1-linker-VL-CL, b) VL-CL-linker-VH-CH1, c) VH-CL-linker-VL-CH1 or d) VL-CH1-linker-VH-CL; and wherein said linker is a polypeptide of at least 30 amino acids, preferably between 32 and 50 amino acids. Said single chain Fab fragments are stabilized via the natural disulfide bond between the CL domain and the CH1 domain.

In some embodiments the antigen binding moiety comprised in the extracellular domain is a crossover single chain Fab fragment which is a polypeptide consisting of an antibody heavy chain variable domain (VH), an antibody constant domain 1 (CH1), an antibody light chain variable domain (VL), an antibody light chain constant domain (CL) and a linker, wherein said antibody domains and said linker have one of the following orders in N-terminal to C-terminal direction: a) VH-CL-linker-VL-CH1 and b) VL-CH1-linker-VH-CL; wherein VH and VL form together an antigen-binding site which binds specifically to an antigen and wherein said linker is a polypeptide of at least 30 amino acids.

The herein described CAR or parts thereof may comprise a signal peptide. Such a signal peptide will bring the protein to the surface of the T cell membrane. For example, in the herein described CAR the signal peptide may have the amino and amino acid sequence as shown in SEQ ID NO:78 (as encoded by the DNA sequence shown in SEQ ID NO:79).

The components of the CAR as described herein can be fused to each other in a variety of configurations to generate T cell activating CARs.

In some embodiments, the CAR comprises an extracellular domain composed of a heavy chain variable domain (VH) and a light chain variable domain (VL) connected to an anchoring transmembrane domain. In some embodiments, the VH domain is fused at the C-terminus to the N-terminus of the VL domain, optionally through a peptide linker. In other embodiments, the CAR further comprises a stimulatory signaling domain and/or a co-stimulatory signaling domain. In a specific such embodiment, the CAR essentially consists of a VH domain and a VL domain, an anchoring transmembrane domain, and optionally a stimulatory signaling domain connected by one or more peptide linkers, wherein the VH domain is fused at the C-terminus to the N-terminus of the VL domain, and the VL domain is fused at the C-terminus to the N-terminus of the anchoring transmembrane domain, wherein the anchoring transmembrane domain is fused at the C-terminus to the N-terminus of the stimulatory signaling domain.

Optionally, the CAR further comprises a co-stimulatory signaling domain. In one such specific embodiment, the antigen binding receptor essentially consists of a VH domain and a VL domain, an anchoring transmembrane domain, a stimulatory signaling domain and a co-stimulatory signaling domain connected by one or more peptide linkers, wherein the VH domain is fused at the C-terminus to the N-terminus of the VL domain, and the VL domain is fused at the C-terminus to the N-terminus of the anchoring transmembrane domain, wherein the anchoring transmembrane domain is fused at the C-terminus to the N-terminus of the stimulatory signaling domain, wherein the stimulatory signaling domain is fused at the C-terminus to the N-terminus of the co-stimulatory signaling domain. In an alternative embodiment, the co-stimulatory signaling domain is connected to the anchoring transmembrane domain instead of the stimulatory signaling domain. In a preferred embodiment, the CAR essentially consists of a VH domain and a VL domain, an anchoring transmembrane domain, a co-stimulatory signaling domain and a stimulatory signaling domain connected by one or more peptide linkers, wherein the VH domain is fused at the C-terminus to the N-terminus of the VL domain, and the VL domain is fused at the C-terminus to the N-terminus of the anchoring transmembrane domain, wherein the anchoring transmembrane domain is fused at the C-terminus to the N-terminus of the co-stimulatory signaling domain, wherein the co-stimulatory signaling domain is fused at the C-terminus to the N-terminus of the stimulatory signaling domain.

In preferred embodiments, the antigen binding moiety is a Fab fragment or a crossFab fragment.

In one preferred embodiment, the antigen binding moiety is fused at the C-terminus of the Fab or crossFab heavy chain to the N-terminus of the anchoring transmembrane domain, optionally through a peptide linker. In an alternative embodiment, the antigen binding moiety is fused at the C-terminus of the Fab or crossFab light chain to the N-terminus of the anchoring transmembrane domain, optionally through a peptide linker. In other embodiments, the CAR further comprises a stimulatory signaling domain and/or a co-stimulatory signaling domain. In a specific such embodiment, the CAR essentially consists of a Fab or crossFab fragment, an anchoring transmembrane domain, and optionally a stimulatory signaling domain connected by one or more peptide linkers, wherein the Fab or crossFab fragment is fused at the C-terminus of the heavy or light chain to the N-terminus of the anchoring transmembrane domain, wherein the anchoring transmembrane domain is fused at the C-terminus to the N-terminus of the stimulatory signaling domain. Preferably, the CAR further comprises a co-stimulatory signaling domain. In one such embodiment, the CAR essentially consists of a Fab or crossFab fragment, an anchoring transmembrane domain, a stimulatory signaling domain and a co-stimulatory signaling domain connected by one or more peptide linkers, wherein the Fab or crossFab fragment is fused at the C-terminus of the heavy or light chain to the N-terminus of the anchoring transmembrane domain, wherein the stimulatory signaling domain is fused at the C-terminus to the N-terminus of the co-stimulatory signaling domain. In a preferred embodiment, the co-stimulatory signaling domain is connected to the anchoring transmembrane domain instead of the stimulatory signaling domain. In a most preferred embodiment, the CAR essentially consists of a Fab or crossFab fragment, an anchoring transmembrane domain, a co-stimulatory signaling domain and a stimulatory signaling domain, wherein the Fab or crossFab fragment is fused at the C-terminus of the heavy chain to the N-terminus of the anchoring transmembrane domain through a peptide linker, wherein the anchoring transmembrane domain is fused at the C-terminus to the N-terminus of the co-stimulatory signaling domain, wherein the co-stimulatory signaling domain is fused at the C-terminus to N-terminus of the stimulatory signaling domain.

As described herein, the CARs used according to the present invention comprise an extracellular domain comprising an antigen binding moiety. A CAR with a single antigen binding moiety capable of specific binding to a target cell antigen is useful and preferred, particularly in cases where high expression of the CAR is needed. In such cases, the presence of more than one antigen binding moiety specific for the target cell antigen may limit the expression efficiency of the CAR. In other cases, however, it will be advantageous to have a CAR comprising two or more antigen binding moieties specific for a target cell antigen, for example to optimize targeting to the target site or to allow crosslinking of target cell antigens.

In a particular embodiment, the antigen binding moiety is a Fab fragment capable of specific binding to CD20, wherein the antigen binding receptor comprises a heavy chain fusion polypeptide comprising an amino acid sequence that is at least about 95%, 96%, 97%, 98%, 99% or 100% identical to the amino acid sequence of SEQ ID NO:7 and a light chain polypeptide comprising an amino acid sequence that is at least about 95%, 96%, 97%, 98%, 99% or 100% identical to the amino acid sequence of SEQ ID NO:9.

In a particular embodiment, the antigen binding moiety is a Fab fragment capable of specific binding to CD20, wherein the antigen binding receptor comprises a light chain fusion polypeptide comprising an amino acid sequence that is at least about 95%, 96%, 97%, 98%, 99% or 100% identical to the amino acid sequence of SEQ ID NO:50 and a heavy chain polypeptide comprising an amino acid sequence that is at least about 95%, 96%, 97%, 98%, 99% or 100% identical to the amino acid sequence of SEQ ID NO:8.

In a preferred embodiment, the antigen binding moiety is a Fab fragment capable of specific binding to CD20, wherein the antigen binding receptor comprises a light chain fusion polypeptide comprising the amino acid sequence of SEQ ID NO:7 and a heavy chain polypeptide comprising the amino acid sequence of SEQ ID NO:9.

In the context of the present invention, binding of the target antigen to the T cell, e.g., a reporter CAR-T cell, leads to activation of the intracellular signaling and/or co-signaling domain. As described herein, in one embodiment, activation of the intracellular signaling and/or co-signaling domain leads to activation of a response element as herein described. In a preferred embodiment, the response element controls the expression of the reporter gene. In this context, upon or after binding of the antigen binding moiety of the CAR to the target antigen, the response element activates the expression of a reporter gene as described herein. Accordingly, the reporter gene in the reporter cells (e.g., the CAR-T reporter cell) is expressed upon binding of the CAR comprising the candidate antigen binding moiety to the target antigen. In one embodiment, the expression of the reporter gene is indicative for binding of the antigen binding moiety to the target antigen. In this context, the binding of the target antigen to the CAR elicits a cellular response which results in a modulation of the activity of the response element, either directly or through a cascade of cell signaling. The response element is a DNA element which can be silenced or activated by transcription factors or the like. Response elements are known in the art and are commercially available, e.g., in reporter vectors. Usually the response element comprises DNA repeat elements and is a cis-acting enhancer element located upstream of a minimal promotor which drives expression of a reporter gene upon transcription factor binding.

Binding of the CAR to the target antigen, e.g., the tumor associated antigen, activates the response element. In one embodiment the response element is a nuclear response element located in the nucleus of the cell. In another embodiment said response element is located on a plasmid in the reporter cell. In one embodiment the assay comprises the preliminary step of transfection of the reporter cells (e.g., a CAR-T cell) with an expression vector comprising the DNA sequence coding for the reporter gene under the control of the response element.

Additionally, the reporter cells can be transfected with an expression vector comprising the DNA sequence coding for the CAR. The reporter cells can be transfected with an expression vector comprising all elements of the signaling cascade (e.g., the CAR, the response element and the reporter gene) or with different vectors individually expressing the different components. In one embodiment, the reporter cells comprise the DNA sequence coding for the reporter gene under the control of the response element and the DNA sequence coding for the CAR.

Accordingly, as described herein, the CAR is functionally linked to a response element. In one embodiment, the response element controls the expression of the reporter gene. In one embodiment, activation of the response element leads to expression of the reporter gene. In one embodiment the response element is part of the NFAT pathway, the NF-κB pathway or the AP-1 pathway. In a preferred embodiment, the response element is part of the NFAT pathway.

In one embodiment the reporter gene is selected from a gene coding for a fluorescent protein or a gene coding for an enzyme whose catalytic activity can be detected. In one embodiment, the reporter gene is coding for a fluorescent or a luminescent protein. In one embodiment, the reporter gene is coding for green fluorescent protein (GFP) or luciferase. In further embodiments the fluorescent protein is selected from the group consisting of green fluorescent protein (GFP), yellow fluorescent protein (YFP), red fluorescent protein (RFP), Blue fluorescent protein (BFP, Heim et al. 1994, 1996), a cyan fluorescent variant known as CFP (Heim et al. 1996; Tsien 1998); a yellow fluorescent variant known as YFP (Oruro et al. 1996; Wachter et al. 1998); a violet-excitable green fluorescent variant known as Sapphire (Tsien 1998; Zapata-Hommer et al. 2003); and a cyan-excitable green fluorescing variant known as enhanced green fluorescent protein or EGFP (Yang et al. 1996) enhanced green fluorescent protein (EGFP) and can be measured, e.g., by live cell imaging (e.g., Incucyte) or fluorescent spectrophotometry. In one embodiment the enzyme whose catalytic activity can be detected is selected from the group consisting of luciferase, beta Galactosidase and Alkaline Phosphatase.

In one embodiment the reporter gene is encoding for GFP. In a preferred embodiment the reporter gene is encoding for luciferase. The activity of luciferase can be detected by commercially available assays, e.g., by Luciferase 1000 Assay System (or ONE-Glo™ Luciferase Assay System (both Promega). The Luciferase 1000 Assay System contains coenzyme A (CoA) besides luciferin as a substrate, resulting in a strong light intensity lasting for at least one minute. For assaying the intracellular luciferase, it is necessary to lyse the cells prior to detection. The light which is produced as a by-product of the reaction is collected by the luminometer from the entire visible spectrum. In the examples shown herein the signal was proportional to the amount of produced luciferase and therefore proportional to the strength of the activation of the used NFAT promotor. In another embodiment a Luciferase assay is used wherein the luciferase is secreted from the cells, hence, the assay can also be performed without lysis of the cells.

Further described herein are transduced T cells, i.e. reporter CAR-T cells, capable of expressing a CAR as described herein. The CAR relates to a molecule which is naturally not comprised in and/or on the surface of T cells and which is not (endogenously) expressed in or on normal (non-transduced) T cells. Thus, the CAR as described herein in and/or on T cells is artificially introduced into T cells.

Accordingly, the CAR as described herein which is artificially introduced and subsequently presented in and/or on the surface of said T cells, e.g., reporter CAR-T cells, comprises domains comprising one or more antigen binding moiety accessible (in vitro or in vivo) to antigens presented on the surface of target cells, in particular tumor cells.

Additionally, the T cells comprise or are transfected with an expression vector comprising the DNA sequence coding for the reporter gene under the control of the response element, e.g., to generate the reporter CAR-T cell as described herein. The T cells can be transfected with an expression vector comprising all elements of the signaling cascade (e.g., the CAR, the response element and the reporter gene) or with different vectors individually expressing the different components. In this context, the reporter cells comprise the DNA sequence coding for the reporter gene under the control of the response element, and the DNA sequence coding for the CAR. Accordingly, after transduction, T cells as described herein, e.g., reporter CAR-T cells, can be activated by a target antigen, particularly by the target antigen of the antigen binding moiety. Described herein are also transduced T cells expressing a CAR encoded by (a) nucleic acid molecule(s) encoding the CAR as described herein. Accordingly, in the context of the present invention, the transduced cell may comprise a nucleic acid molecule encoding the CAR(s) as described herein and/or the response element(s) and reporter gene(s).

In the context of the present invention, the term "transduced T cell" relates to a genetically modified T cell (i.e. a T cell wherein a nucleic acid molecule has been introduced deliberately).

In particular, the nucleic acid molecule encoding the CAR(s), the response element(s) and the reporter gene(s) as described herein can be stably integrated into the genome of the T cell by using a retroviral or lentiviral transduction. The extracellular domain of the CAR may comprise the complete extracellular domain of an antigen binding moiety as described herein but also parts thereof. The minimal size required being the antigen binding site of the antigen binding moiety in the CAR. The extracellular portion of the CAR can be detected on the cell surface, while the intracellular portion (i.e. the co-stimulatory signaling domain(s) and the stimulatory signaling domain) are not detectable on the cell surface. The detection of the extracellular domain of the CAR can be carried out by using an antibody which specifically binds to this extracellular domain or by the recognition domain, e.g., the target antigen, which the antigen binding moiety is capable to bind. The extracellular domain can be detected using these antibodies or antigens by flow cytometry or microscopy.

The transduced cells may be any immune cell. These include but are not limited to B-cells, T cells, Natural Killer (NK) cells, Natural Killer (NK) T cells, γδ T cells, innate lymphoid cells, macrophages, monocytes, dendritic cells, or neutrophils and immortalized cell lines thereof.

Preferentially, said immune cell would be a lymphocyte, preferentially a NK or T cells. The said T cells include $CD4^+$ T cells and $CD8^+$ T cells. Triggering of the CAR on the surface of the leukocyte will render the cell responsive against a target cell irrespective of the lineage the cell originated from. Activation will happen irrespective of the stimulatory signaling domain or co-stimulatory signaling domain chosen for the CAR and is not dependent on the exogenous supply of additional cytokines.

In the examples and as a proof of the inventive concept of the present invention an activation assay based on Jurkat NFAT reporter CAR-T cells is described. In one embodiment, the reporter cell is a Jurkat NFAT cell. Jurkat cells are an immortalized line of human T lymphocyte cells.

The Jurkat NFAT cell line is known in the art and contains a firefly luciferase gene under the control of the NFAT response element stably integrated into the cells. According to the inventive concept as described herein and as a proof of concept, Jukat NFAT cells were transduced with CARs as described herein and in the appended examples to generate the Jurkat NFAT reporter CAR-T cells as described herein and as used according to the present invention.

Accordingly, in one preferred embodiment, the Jurkat NFAT cell additionally comprises a CAR as described herein, i.e. these cells are referred to as Jurkat NFAT reporter CAR-T cells.

In this context, the cell may be co-transduced with additional nucleic acid molecules, e.g., with a nucleic acid molecule encoding a CAR and/or a response element and/or a reporter gene as described herein.

Specifically, the present invention relates to a method for the use of a reporter CAR-T cell expressing one or more CAR and one or more response elements and reporter genes, comprising the steps of transducing a T cell with one or several vectors as described herein and culturing the transduced T cell under conditions allowing the expressing of the antigen binding receptor in or on said transduced cell.

Methods for transducing cells (e.g., T cells) are known in the art and include, without being limited, in a case where nucleic acid or a recombinant nucleic acid is transduced, for example, an electroporation method, calcium phosphate method, cationic lipid method or liposome method. The nucleic acid to be transduced can be conventionally and highly efficiently transduced by using a commercially available transfection reagent, for example, Lipofectamine (manufactured by Invitrogen, catalogue no.: 11668027). In a case where a vector is used, the vector can be transduced in the same manner as the above-mentioned nucleic acid as long as the vector is a plasmid vector (i.e. a vector which is not a viral vector).

The transduced T cell/T cells is/are preferably grown under controlled conditions, outside of their natural environment. In particular, the term "culturing" means that cells (e.g., the transduced cell(s)) which are in vitro. Culturing cells is a laboratory technique of keeping cells alive which are separated from their original tissue source. Herein, the transduced cell of the present invention is cultured under conditions allowing the expression of the CAR in or on said transduced cells. Conditions which allow the expression or a transgene (i.e. of the CAR and/or reporter gene) are commonly known in the art.

As described herein, the expression of the reporter gene can be directly correlated with the functionality of the antigen binding moiety to be tested and the resulting activation of the T cell, e.g., the reporter CAR-T cell. For example when using a gene encoding for a fluorescent protein or a gene encoding for luciferase as a reporter gene, the amount of light detected from the cells correlates directly with the target antigen binding and specificity of the antibody to be tested.

In one embodiment, the target antigen is a cell surface receptor. In one embodiment, the target antigen is a tumor associated antigen. In one embodiment, the tumor associated antigen is selected from the group consisting of CEA, Her2, TYRP, EGFR, MCSP, STEAP1, WT1 and FolR1.

The target antigen is not limited to proteins located on the cell surface but may also derive from polypeptides or proteins which are temporarily or permanently located intracellularly. In such cases, the target antigen deriving from an intracellular polypeptide or protein can be presented on the cell surface by one or several molecules of the major histocompatibility complex (MHC).

In one embodiment, the target antigen is a peptide bound to a molecule of the MHC. In one embodiment, the MHC is a human MHC. In one embodiment, the peptide bound to a molecule of the MHC has an overall length of between 8 and 100, preferably between 8 and 30, and more preferred between 8 and 16 amino acids. In one embodiment, the target antigen derives from a protein which is exclusively or mainly expressed in tumor tissue. In one embodiment, the protein is an intracellular protein and the peptide is generated by the MHC-I or MHC-II pathway and presented by a MHC class I or MHC class II complex. In one embodiment, the peptide is generated by the MHC-I pathway and presented by a MHC class I complex. Major histocompatibility complex (MHC) class I molecules present peptides from endogenous antigens to CD8+ cytotoxic T cells, and therefore, MHC-peptide complexes are a suitable target for immunotherapeutic approaches. The MHC-peptide complexes can be targeted by recombinant T-cell receptors (TCRs). However, most TCRs may have affinities which are too low immunotherapy whereas high affinity binding moieties would be beneficial. Towards this end, high-affinity soluble antibody molecules with TCR-like specificity can be generated, e.g., by generating phage display libraries (e.g., combinatorial libraries) and screening such libraries as further described herein. These soluble antigen binding moieties e.g., scFv or Fab, with TCR-like specificity herein are referred to as "T cell receptor like antigen binding moieties" or "TCRL antigen binding moieties". In one embodiment, the antigen binding moiety is a T cell receptor like (TCRL) antigen binding moiety. The TCRL antigen binding moiety is capable of specific binding to a peptide antigen which is exclusively or mainly expressed in tumor tissue, wherein the peptide antigen is bound to a molecule of the MHC located on the surface of a cell, particularly a cancer cell. In this context, the methods of the present invention are suitable to assess specificity of established or novel TCRL antigen binding moieties in a high-throughput assay format.

The binding of the antigen binding moiety to the target antigen can be determined qualitatively or qualitatively, i.e. by the presence or absence of the expression of the reporter gene; with the absence of any fluorescence or luminescence being indicative of no binding. For quantitative measurement of binding and activation the amount of reporter gene activation can be compared to a reference. Accordingly, the method as described herein may additionally comprise the step of comparing the level of expression of the reporter gene to a reference. A suitable reference usually comprises a negative control which is substantially identical to the referenced assay omitting one essential component of the assay or method. For the methods of the invention the omitted component may be, e.g., omitting addition of the target cell. Alternatively, a reporter CAR-T cell binding to a different target antigen not present in the assay can be used.

Accordingly, in one embodiment, the reference is expression of the reporter gene in absence of the target antigen. In a preferred embodiment, the reference is expression of the reporter gene in absence of the target cell. In specific embodiments, the expression of the reporter gene is at least 2×, 3×, 4×, 5×, 10×, 100×, 1000×, or 10000×, higher compared to the expression of the reporter gene in absence of the target cell.

Alternatively, the absence of reporter gene expression can be defined by a certain threshold, i.e. after deduction of a background signal. The background signal is usually determined by performing the assay with all reagents but the target antigen of the antigen binding moiety to be tested or in absence of the target cells comprising said target antigen. A novel antigen binding moiety can, e.g., be selected according to the method of the invention by defining a threshold for baseline activation of the reporter gene expression and selecting the novel antigen binding moiety if the level of expression of the reporter gene in the presence of the target cell in relation to the expression of the reporter gene in absence of the target cell is higher than a predefined threshold value. Accordingly, the method as described herein may additionally comprise the step of selecting the novel antigen binding moiety if the level of expression of the reporter gene in the presence of the target cell in relation to the expression of the reporter gene in absence of the target cell is higher than a predefined threshold value. In specific embodiments, the threshold value is 2, 3, 4, 5, 10, 100, 1000, or 10000.

The novel assay as described herein is robust, suitable for use in high-throughput format and efficient in terms of hands-on time needed to accomplish the assay. Furthermore, the assay of the present invention tolerates the presence of dead cells in the sample to be analyzed. This is in contrast to cell assays wherein the binding and functionality of an antibody is determined by measuring cell viability or cell death, e.g., a killing assay.

One further advantage of the new assay described herein is that no washing steps are required.

The reporter cells can be added to the target cells, e.g., tumor cells, in either order. In one embodiment, the tumor sample is added to the cell culture medium containing the reporter CAR-T cells in a suitable cell culture format, e.g., in a well of a 24 well plate, in a well of a 96 well plate, or in a well of a 384 well plate. Preferably the testing medium is a medium that provides conditions for cells to be viable for up to 48 hours. Suitable media are for example Jurkat medium, as outlined in the examples. In one embodiment the assay is performed in a microtiter plate. In one embodiment the microtiter plate is suitable for high-throughput screening. The assay of the present invention can be performed in any format that allows for rapid preparation, processing, and analysis of multiple reactions. This can be, for example, in multi-well assay plates (e.g., 24 wells, 96 wells or 386 wells). Stock solutions for various agents can be made manually or robotically, and all subsequent pipetting, diluting, mixing, distribution, washing, incubating, sample readout, data collection and analysis can be done robotically using commercially available analysis software, robotics, and detection instrumentation capable of detecting fluorescent and/or luminescent signals.

In one embodiment about 100000 to about 1000000 reporter CAR-T cells per well of a 24-well plate are provided in step 1.c). In a preferred embodiment about 300000 to about 700000 cells or about 400000 to about 600000 reporter CAR-T cells per well of a 24-well plate are provided.

In one embodiment about 500000 reporter CAR-T cells per well of a 24-well plate are provided in step 1.c). In one embodiment about 10000 to about 100000 reporter CAR-T per well of a 96-well plate are provided in step 1.c). In a preferred embodiment about 30000 to about 70000 reporter CAR-T or about 40000 to about 60000 reporter CAR-T per well of a 96-well plate are provided. In one embodiment about 50000 reporter CAR-T per well of a 96-well plate are provided in step 1.c). In one embodiment about 3000 to about 30000 reporter CAR-T cells per well of a 384-well plate are provided in step c). In a preferred embodiment about 5000 to about 15000 cells or about 8000 to about 12000 reporter CAR-T cells per well of a 384-well plate are provided. In one embodiment about 10000 reporter CAR-T cells per well of a 384-well plate are provided in step c). In one embodiment about 200000 to about 2000000 reporter CAR-T per ml of cell culture medium are provided in step 1.c). In a preferred embodiment about 600000 to about 1400000 reporter CAR-T or about 800000 to about 1200000 reporter CAR-T per ml of cell culture medium are provided. In one embodiment about 1000000 reporter CAR-T per ml of cell culture medium are provided in step 1.c).

In one embodiment, the target cells, e.g., tumor cells or tumor samples, are provided in cell culture inserts. In one embodiment, the target cells, e.g., tumor samples are embedded in Matrigel.

In certain embodiments methods of the invention can be used to assess specificity of a novel antigen binding moiety to be included in a T cell bispecific (TCB) format. The methods according to the present invention are particularly suitable to assess and select novel antigen binding moieties for TCBs because the methods of the present invention measure T cell activation. It is a drawback of assays known in the art (e.g., affinity-based FACS assay) that the measured affinity does not always reflect the specificity in the TCB format. TCBs are highly potent molecules able to mediate T cell activation and killing already through binding affinities in the micromolar range. TCBs comprising a novel target antigen binding moiety therefore need to be highly selective to avoid unspecific reactivity, e.g., killing of healthy cells or alloreactivity.

The methods as described in the present invention satisfy the high demands of such formats because, without being bound to theory, the assay of the present is based on T cell activation and a comparable mechanism of action. Accordingly, provided is a method as described herein, wherein high level of expression of the reporter gene in the presence of the target cell and low level of expression of the reporter gene in the absence of the target cell is indicative for high specificity of the antigen binding moiety, in particular when the antigen binding moiety is transferred into a T cell bispecific (TCB) antibody format. Furthermore, provided is a method for generating a TCB antibody, wherein the TCB antibody format comprises a first antigen binding moiety specific for a target antigen and a second antigen binding moiety capable of specific binding to a T cell activating receptor, wherein the first antigen binding moiety is selected according to the method as described herein. In preferred embodiments, the T cell activating receptor is CD3.

In one such embodiment the TCB format comprises
(a) a first antigen binding moiety, in particular a Fab molecule, capable of specific binding to a target cell antigen;
(b) a second antigen binding moiety, in particular a Fab molecule, capable of specific binding to CD3.

In one specific embodiment the bispecific antibody comprises
(a) a first antigen binding moiety which is a Fab molecule capable of specific binding to a target cell antigen;
(b) a second antigen binding moiety which is a Fab molecule capable of specific binding to CD3, and which comprises the heavy chain complementarity determining region (CDR) of SEQ ID NO:88, SEQ ID NO:89 and SEQ ID NO:90 and the light chain CDR of SEQ ID NO:91, SEQ ID NO:92, SEQ ID NO:93.

A bispecific antibody with a single antigen binding moiety capable of specific binding to a target cell antigen is useful, particularly in cases where internalization of the target cell antigen is to be expected following binding of a high affinity antigen binding moiety. In such cases, the presence of more than one antigen binding moiety specific for the target cell antigen may enhance internalization of the target cell antigen, thereby reducing its availability.

In many other cases, however, it will be advantageous to have a bispecific antibody comprising two or more antigen binding moieties specific for a target cell antigen, for example to optimize targeting to the target site.

Accordingly, in certain embodiments, the TCB format comprises a third antigen binding moiety capable of specific binding to a target cell antigen. In further embodiments, the third antigen binding moiety is a conventional Fab molecule, or a crossover Fab molecule wherein either the variable or the constant regions of the Fab light chain and the Fab heavy chain are exchanged.

In one embodiment, the third antigen binding moiety is capable of specific binding to the same target cell antigen as the first antigen binding moiety. In a particular embodiment, the second antigen binding moiety is capable of specific binding to CD3, and the first and third antigen binding moieties are capable of specific binding to a target cell antigen. In a particular embodiment, the first and the third antigen binding moiety are identical (i.e. they comprise the same amino acid sequences).

A further aspect of the present invention are nucleic acids and vectors encoding one or several CARs used according to the present invention. The nucleic acid molecules may be under the control of regulatory sequences. For example, promoters, transcriptional enhancers and/or sequences which allow for induced expression of the CARs may be employed. In the context of the present invention, the nucleic acid molecules are expressed under the control of constitutive or inducible promoter. Suitable promoters are, e.g., the CMV promoter (Qin et al., PLoS One 5(5) (2010), e10611), the UBC promoter (Qin et al., PLoS One 5(5) (2010), e10611), PGK (Qin et al., PLoS One 5(5) (2010), e10611), the EF1A promoter (Qin et al., PLoS One 5(5) (2010), e10611), the CAGG promoter (Qin et al., PLoS One 5(5) (2010), e10611), the SV40 promoter (Qin et al., PLoS One 5(5) (2010), e10611), the COPIA promoter (Qin et al., PLoS One 5(5) (2010), e10611), the ACTSC promoter (Qin et al., PLoS One 5(5) (2010), e10611), the TRE promoter (Qin et al., PLoS One. 5(5) (2010), e10611), the Oct3/4 promoter (Chang et al., Molecular Therapy 9 (2004), S367-S367 (doi: 10.1016/j.ymthe.2004.06.904)), or the Nanog promoter (Wu et al., Cell Res. 15(5) (2005), 317-24). Herein the term vector relates to a circular or linear nucleic acid molecule which can autonomously replicate in a cell (i.e. in a transduced cell) into which it has been introduced. Many suitable vectors are known to those skilled in molecular biology, the choice of which would depend on the function desired and include plasmids, cosmids, viruses, bacteriophages and other vectors used conventionally in genetic engineering. Methods which are well known to those skilled in the art can be used to construct various plasmids and vectors; see, for example, the techniques described in Sambrook et al. (loc cit.) and Ausubel, Current Protocols in Molecular Biology, Green Publishing Associates and Wiley Interscience, N.Y. (1989), (1994). Alternatively, the polynucleotides and vectors of the invention can be reconstituted into liposomes for delivery to target cells. As discussed in further details below, a cloning vector was used to isolate individual sequences of DNA. Relevant sequences can be transferred into expression vectors where expression of a particular polypeptide is required. Typical cloning vectors include pBluescript SK, pGEM, pUC9, pBR322, pGA18 and pGBT9. Typical expression vectors include pTRE, pCAL-n-EK, pESP-1, pOP13CAT.

In the context of the present invention the vector can be polycistronic. Such regulatory sequences (control elements) are known to the skilled person and may include a promoter, a splice cassette, translation initiation codon, translation and insertion site for introducing an insert into the vector(s). In the context of the present invention, said nucleic acid molecule(s) is (are) operatively linked to said expression control sequences allowing expression in eukaryotic or prokaryotic cells. It is envisaged that said vector(s) is (are) an expression vector(s) comprising the nucleic acid molecule(s) encoding the CAR as defined herein. Operably linked refers to a juxtaposition wherein the components so described are in a relationship permitting them to function in their intended manner. A control sequence operably linked to a coding sequence is ligated in such a way that expression of the coding sequence is achieved under conditions compatible with the control sequences. In case the control sequence is a promoter, it is obvious for a skilled person that double-stranded nucleic acid is preferably used.

In the context of the present invention the recited vector(s) is (are) an expression vector(s). An expression vector is a construct that can be used to transform a selected cell and provides for expression of a coding sequence in the selected cell. An expression vector(s) can for instance be cloning (a) vector(s), (a) binary vector(s) or (a) integrating vector(s). Expression comprises transcription of the nucleic acid molecule preferably into a translatable mRNA. Regulatory elements ensuring expression in prokaryotes and/or eukaryotic cells are well known to those skilled in the art. In the case of eukaryotic cells they comprise normally promoters ensuring initiation of transcription and optionally poly-A signals ensuring termination of transcription and stabilization of the transcript. Possible regulatory elements permitting expression in prokaryotic host cells comprise, e.g., the PL, lac, trp or tac promoter in *E. coli*, and examples of regulatory elements permitting expression in eukaryotic host cells are the AOX1 or GAL1 promoter in yeast or the CMV-, SV40, RSV-promoter (Rous sarcoma virus), CMV-enhancer, SV40-enhancer or a globin intron in mammalian and other animal cells.

Beside elements which are responsible for the initiation of transcription such regulatory elements may also comprise transcription termination signals, such as the SV40-poly-A site or the tk-poly-A site, downstream of the polynucleotide. Furthermore, depending on the expression system used leader sequences encoding signal peptides capable of directing the polypeptide to a cellular compartment or secreting it into the medium may be added to the coding sequence of the recited nucleic acid sequence and are well known in the art; see also, e.g., appended Examples.

The leader sequence(s) is (are) assembled in appropriate phase with translation, initiation and termination sequences, and preferably, a leader sequence capable of directing secretion of translated protein, or a portion thereof, into the periplasmic space or extracellular medium.

Optionally, the heterologous sequence can encode a CAR including an N-terminal identification peptide imparting desired characteristics, e.g., stabilization or simplified purification of expressed recombinant product; see supra. In this context, suitable expression vectors are known in the art such as Okayama-Berg cDNA expression vector pcDV1 (Pharmacia), pCDM8, pRc/CMV, pcDNA1, pcDNA3 (Invitrogene), pEF-DHFR, pEF-ADA or pEF-neo (Raum et al. Cancer Immunol Immunother 50 (2001), 141-150) or pSPORT1 (GIBCO BRL).

The described nucleic acid molecule(s) or vector(s) which is (are) introduced in the T cell or its precursor cell may either integrate into the genome of the cell or it may be maintained extrachromosomally.

Exemplary Embodiments

1. A method for assessing the specificity of an antigen binding moiety comprising the steps of:
   a. providing an antigen binding moiety specific for a target antigen;
   b. generating a chimeric antigen receptor (CAR) expressing reporter T (CAR-T) cell by:
      i. transferring the antigen binding moiety into a CAR vector system operationally coupled to a response element;
      ii. transferring the CAR vector system into a reporter T cell comprising a reporter gene under the control of the response element;
   c. contacting the reporter CAR-T cell with a target cell comprising the target antigen on the surface, in particular wherein the target cell is a cancer cell; and
   d. determining T cell activation by determining the expression of the reporter gene to establish the specificity of the antigen binding moiety.
2. The method of embodiment 1, wherein the antigen binding moiety is a Fab fragment, in particular a Fab fragment deriving from a phage display library screening.
3. The method of any one of embodiments 1 or 2, wherein the antigen binding moiety comprises a variable heavy chain domain (VH) and a variable light chain domain (VL) and wherein the VH and VL domains of the antigen binding moiety are transferred to the CAR, in particular wherein coding polynucleotide sequences for the VH and VL domains of the antigen binding moiety are transferred to the CAR vector system.
4. The method of any one of embodiments 1 to 3, wherein the CAR vector system encodes a CAR comprising an antigen binding moiety, an anchoring transmembrane domain and at least one intracellular signaling and/or co-signaling domain.
5. The method of embodiment 4, wherein binding of the target antigen to the reporter CAR-T cell leads to activation of the intracellular signaling and/or co-signaling domain.
6. The method of any one of embodiments 5 or 6, wherein activation of the intracellular signaling domain leads to activation of the response element.
7. The method according to any one of embodiments 1 to 6, wherein the response element controls the expression of the reporter gene.
8. The method according to any one of embodiments 1 to 7, wherein activation of the response element leads to expression of the reporter gene.
9. The method according to any one of embodiments 1 to 8, wherein the response element is part of the NFAT pathway, the NF-κB pathway or the AP-1 pathway.
10. The method according to any one of embodiments 1 to 9, wherein the reporter gene is coding for luminescent protein, in particular for a fluorescent protein.
11. The method according to any one of embodiments 1 to 10, wherein the reporter gene is coding for green fluorescent protein (GFP) or luciferase.
12. The method according to any one of embodiments 1 to 11, wherein the target antigen is a cell surface receptor.

13. The method according to any one of embodiments 1 to 12, wherein the target antigen is a peptide bound to a molecule of the human major histocompatibility complex (MHC).
14. The method according to embodiment 13, wherein the antigen binding moiety is a T cell receptor like (TCRL) antigen binding moiety.
15. The method according to any one of embodiments 1 to 14, additionally comprising the step of:
    e) comparing the level of expression of the reporter gene to a reference.
16. The method according to embodiment 15, wherein the reference is expression of the reporter gene in absence of the target cell.
17. The method according to embodiment 16, wherein the expression of the reporter gene is at least 2×, 3×, 4×, 5×, 10×, 100×, 1000×, or 10000×, higher compared to the expression of the reporter gene in absence of the target cell.
18. The method according to embodiment 15, additionally comprising the step of:
    f) selecting the novel antigen binding moiety if the level of expression of the reporter gene in the presence of the target cell in relation to the expression of the reporter gene in absence of the target cell is higher than a predefined threshold value.
19. The method according to embodiment 18, wherein the threshold value is 2, 3, 4, 5, 10, 100, 1000, or 10000.
20. The method according to any one of embodiments 1 to 19, wherein high level of expression of the reporter gene in the presence of the target cell and low level of expression of the reporter gene in the absence of the target cell is indicative for high specificity of the antigen binding moiety.
21. The method according to any one of embodiments 1 to 20, wherein high level of expression of the reporter gene in the presence of the target cell and low level of expression of the reporter gene in the absence of the target cell is indicative for high specificity of a T cell bispecific (TCB) antibody comprising the antigen binding moiety.
22. The method according to any one of embodiments 1 to 21, wherein the method is an in vitro method.
23. A method for generating a TCB antibody, wherein the TCB antibody format comprises a first antigen binding moiety specific for a target antigen and a second antigen binding moiety capable of specific binding to a T cell activating receptor, wherein the first antigen binding moiety is selected according to the method of any one of embodiments 1 to 22.
24. The method of embodiment 23, wherein the T cell activating receptor is CD3.
25. The methods as hereinbefore described.

EXAMPLES

The following are examples of methods and compositions of the invention. It is understood that various other embodiments may be practiced, given the general description provided above.

Recombinant DNA Techniques

Standard methods were used to manipulate DNA as described in Sambrook et al., Molecular cloning: A laboratory manual; Cold Spring Harbor Laboratory Press, Cold Spring Harbor, N.Y., 1989. The molecular biological reagents were used according to the manufacturer's instructions. General information regarding the nucleotide sequences of human immunoglobulin light and heavy chains is given in: Kabat, E. A. et al., (1991) Sequences of Proteins of Immunological Interest, Fifth Ed., NIH Publication No 91-3242.

DNA Sequencing

DNA sequences were determined by double strand sequencing.

Gene Synthesis

Desired gene segments were either generated by PCR using appropriate templates or were synthesized by Geneart AG (Regensburg, Germany) from synthetic oligonucleotides and PCR products by automated gene synthesis. The gene segments flanked by singular restriction endonuclease cleavage sites were cloned into standard cloning/sequencing vectors. The plasmid DNA was purified from transformed bacteria and concentration determined by UV spectroscopy. The DNA sequence of the subcloned gene fragments was confirmed by DNA sequencing. Gene segments were designed with suitable restriction sites to allow sub-cloning into the respective expression vectors. All constructs were designed with a 5'-end DNA sequence coding for a leader peptide which targets proteins for secretion in eukaryotic cells.

Protein Purification

Proteins were purified from filtered cell culture supernatants referring to standard protocols. In brief, antibodies were applied to a Protein A Sepharose column (GE healthcare) and washed with PBS. Elution of antibodies was achieved at pH 2.8 followed by immediate neutralization of the sample. Aggregated protein was separated from monomeric antibodies by size exclusion chromatography (Superdex 200, GE Healthcare) in PBS or in 20 mM Histidine, 150 mM NaCl pH 6.0. Monomeric antibody fractions were pooled, concentrated (if required) using, e.g., a MILLIPORE Amicon Ultra (30 MWCO) centrifugal concentrator, frozen and stored at −20° C. or −80° C. Part of the samples were provided for subsequent protein analytics and analytical characterization, e.g., by SDS-PAGE and size exclusion chromatography (SEC).

SDS-PAGE

The NuPAGE® Pre-Cast gel system (Invitrogen) was used according to the manufacturer's instruction. In particular, 10% or 4-12% NuPAGE® Novex® Bis-TRIS Pre-Cast gels (pH 6.4) and a NuPAGE® MES (reduced gels, with NuPAGE® Antioxidant running buffer additive) or MOPS (non-reduced gels) running buffer was used.

Analytical Size Exclusion Chromatography

Size exclusion chromatography (SEC) for the determination of the aggregation and oligomeric state of antibodies was performed by HPLC chromatography. Briefly, Protein A purified antibodies were applied to a Tosoh TSKgel G3000SW column in 300 mM NaCl, 50 mM $KH_2PO_4$/$K_2HPO_4$, pH 7.5 on an Agilent HPLC 1100 system or to a Superdex 200 column (GE Healthcare) in 2× PBS on a Dionex HPLC-System. The eluted protein was quantified by UV absorbance and integration of peak areas. BioRad Gel Filtration Standard 151-1901 served as a standard.

Lentiviral Transduction of Jurkat NFAT T Cells

To produce lentiviral vectors, respective DNA sequences for the correct assembly of the CAR were cloned in frame in a lentiviral polynucleotide vector under a constitutively active human cytomegalovirus immediate early promoter (CMV). The retroviral vector contained a woodchuck hepatitis virus posttranscriptional regulatory element (WPRE), a central polypurine tract (cPPT) element, a pUC origin of replication and a gene encoding for antibiotic resistance facilitating the propagation and selection in bacteria.

To produce functional virus particles, Lipofectamine LTX™ based transfection was performed using 60-70% confluent Hek293T cells (ATCC CRL3216) and CAR containing vectors as well as pCMV-VSV-G:pRSV-REV: pCgpV transfer vectors at 3:1:1:1 ratio. After 48 h supernatant was collected, centrifuge for 5 minutes at 250 g to remove cell debris and filtrated through 0.45 or 0.22 μm polyethersulfon filter. Concentrated virus particles (Lenti-x-Concentrator, Takara) were used to transduce Jurkat NFAT cells (Signosis). Positive transduced cells were sorted as pool or single clones using FACSARIA sorter (BD Bioscience). After cell expansion to appropriate density Jurkat NFAT T cells were used for experiments.

Example 1

Described herein is a Jurkat NFAT T cell reporter assay using CD20 expressing SUDHDL4 tumor cells as target cells and a sorted single clone of anti-CD20-Fab-CD28ATD-CD28CSD-CD3zSSD expressing Jurkat NFAT T cells as target cells (FIG. 4). As positive control, some wells of a 96 well plate (Cellstar Greiner-bio-one, CAT-No. 655185) were coated with 10 μg/ml CD3 antibody (from Biolegend®) in phosphate buffered saline (PBS) either for 4° C. over night or for at least 1h at 37° C. The CD3 antibody coated wells were washed twice with PBS, after the final washing step PBS was fully removed. Jurkat NFAT wild type cells or Jurkat NFAT CAR cells engineered to express the antigen binding receptor anti-CD20-Fab-CD28ATD-CD28CSD-CD3zS SD (further termed as reporter cells), were counted and checked for their viability using Cedex HiRes. Cell number was adjusted to $1 \times 10^6$ viable cells/ml.

Therefore an appropriate aliquot of the cell suspension was pelleted at 210 g for 5 min at room temperature (RT) and resuspended in fresh RPMI-160+10% FCS+1% Glutamax (growth medium). Target cells expressing the antigen of interest, were counted and checked for their viability as well. Cell number was adjusted to $1 \times 10^6$ viable cells/ml in growth medium. Target cells and reporter cells were plated in 10:1, 5:1, 2:1 or 1:1 E:T ratio (110.000 cells per well in total) in triplicates in a 96-well suspension culture plate (Greiner-bio one) in a final volume of 200 μl. After that the 96 well plate was centrifuged for 2 min at 190 g and RT and sealed with Parafilm®.

After 20 hours at 37° C. and 5% $CO_2$ in humidity atmosphere incubation the content of each well was mixed by pipetting up and down 10 times using a multichannel pipette. 100 μl cell suspension was transferred to a new white transparent bottom 96 well plate (Greiner-bio-one) and 100 μl ONE-Glo™ Luciferase Assay (Promega) was added. After 15 min incubation in the dark on a rotary shaker at 300 rpm and RT luminescence was measured using a Tecan® Spark10M plate reader, 1 sec/well as detection time.

The bar diagram shows the activation of anti-CD20-Fab-CD28ATD-CD28CSD-CD3zSSD expressing Jurkat NFAT T cells dependent on different E:T ratios and dependent of the time of co-cultivation with target cells. It is shown that Jurkat NFAT T cell activation is dependent on the duration of the co-cultivation with target cells and dependent on the E:T ratio. For all tested conditions an incubation time of 20 hours displays the highest luminescence signal. Further, among the different E:T ratios the 10:1 E:T ratio depicts the highest detectable luminescence signal. Jurkat NFAT wild type T cells show only a time dependent increase in luminescence signal, whereby after 40 hours the highest luminescence signal can be detected. The detected luminescence signal is independent of E:T ratio and in general also clearly lower than each luminescence signal detected for anti-CD20-Fab-CD28ATD-CD28CSD-CD3zSSD expressing Jurkat NFAT T cells at the respective time points. In general, the highest luminescence signal is detectable if cells were incubated in CD3 antibody coated wells. The anti-CD20-Fab-CD28ATD-CD28CSD-CD3zSSD expressing Jurkat NFAT T cells depict a higher signal compared to not transduced Jurkat NFAT control T cells. Each point represents the mean of a technical duplicate.

Example 2

Described herein is a Jurkat NFAT T cell reporter assay using CD20 expressing SUDHDL4 tumor cells as target cells and a sorted single clone of anti-CD20-Fab-CD28ATD-CD28CSD-CD3zSSD or anti-CD20-crossFab-CD28ATD-CD28CSD-CD3zSSD expressing Jurkat NFAT T cells as target cells (FIG. 5). As positive control, wells of a 96 well plate (Cellstar Greiner-bio-one, CAT-No. 655185) were coated with 10 μg/ml CD3 antibody (from Biolegend®) in phosphate buffered saline (PBS) at 4° C. over night. The CD3 antibody coated wells were washed twice with PBS, after the final washing step PBS was fully removed. Jurkat NFAT wild type cells or Jurkat NFAT T cells engineered to express anti-CD20-Fab-CD28ATD-CD28CSD-CD3zSSD or anti-CD20-crossFab-CD28ATD-CD28CSD-CD3zSSD (further termed as reporter cells), were counted and checked for their viability using Cedex HiRes. Cell number was adjusted to $1 \times 10^6$ viable cells/ml. Therefore an appropriate aliquot of the cell suspension was pelleted at 210 g for 5 min at room temperature (RT) and resuspended in fresh RPMI-160+10% FCS+1% Glutamax (growth medium). Target cells, expressing the antigen of interest were counted and checked for their viability as well. Cell number was adjusted to $1 \times 10^6$ viable cells/ml in growth medium. Target cells and reporter cells were plated in 5:1 E:T ratio (110.000 cells per well in total) in triplicates in a 96- well suspension culture plate (Greiner-bio one) in a final volume of 200 μl. After that the 96 well plate was centrifuged for 2 min at 190 g and RT and sealed with Parafilm®.

After 20 hours at 37° C. and 5% $CO_2$ in humidity atmosphere incubation the content of each well was mixed by pipetting up and down 10 times using a multichannel pipette. 100 μl cell suspension was transferred to a new white transparent bottom 96 well plate (Greiner-bio-one) and 100 μl ONE-Glo™ Luciferase Assay (Promega) was added. After 15 min incubation in the dark on a rotary shaker at 300 rpm and RT luminescence was measured using Tecan® Spark10M plate reader, 1 sec/well as detection time.

The bar diagram shows activation of anti-CD20-Fab-CD28ATD-CD28CSD-CD3zSSD expressing Jurkat NFAT T cells and anti-CD20-crossFab-CD28ATD-CD28CSD-CD3zSSD expressing Jurkat NFAT T cells upon co-cultivation with target cells. If anti-CD20-Fab-CD28ATD-CD28CSD-CD3zSSD or anti-CD20-crossFab-CD28ATD-CD28CSD-CD3zSSD expressing Jurkat NFAT T cells or Jurkat NFAT control T cells were cultivated without target cells, no luminescence signal was detected. The highest luminescence signal was detected when either anti-CD20-Fab-CD28ATD-CD28CSD-CD3zSSD or anti-CD20-cross-Fab-CD28ATD-CD28CSD-CD3zSSD expressing Jurkat NFAT T cells or Jurkat NFAT control T cells were co-cultivated with target cells in CD3 antibody coated plates. Surprisingly, the crossFab format leads to strong activation of Jurkat NFAT T cells in conjunction with CD3 mediated signaling.

Each point represents the mean value of technical triplicates. Standard deviation is indicated by error bars.

Example 3

Described herein is a Jurkat NFAT T cell reporter assay performed using CD20 expressing SUDHDL4 tumor cells as target cells and a sorted pool of anti-CD20-scFab-CD28ATD-CD28CSD-CD3zSSD expressing Jurkat NFAT T cells as target cells (FIG. 6).

As positive control, wells of a 96 well plate (Cellstar Greiner-bio-one, CAT-No. 655185) were coated with 10 µg/ml CD3 antibody (from Biolegend®) in phosphate buffered saline (PBS) either for 4° C. over night or for at least 1 h at 37° C. The CD3 antibody coated wells were washed twice with PBS, after the final washing step PBS was fully removed. Jurkat NFAT wild type T cells or Jurkat NFAT T cells engineered to express anti-CD20-scFab-CD28ATD-CD28CSD-CD3zSSD (further termed as reporter cells), were counted and checked for their viability using Cedex HiRes. Cell number was adjusted to $1\times10^6$ viable cells/ml. Therefore an appropriate aliquot of the cell suspension was pelleted at 210 g for 5 min at room temperature (RT) and resuspended in fresh RPMI-160+10% FCS+1% Glutamax (growth medium). Target cells expressing the antigen of interest, were counted and checked for their viability as well. Cell number was adjusted to $1\times10^6$ viable cells/ml in growth medium. Target cells and reporter cells were plated in 10:1, 5:1, 2:1 or 1:1 E:T ratio (110.000 cells per well in total) in triplicates in a 96-well suspension culture plate (Greiner-bio one) in a final volume of 200. After that the 96 well plate was centrifuged for 2 min at 190 g and RT and sealed with Parafilm®.

After 20 hours at 37° C. and 5% $CO_2$ in humidity atmosphere incubation the content of each well was mixed by pipetting up and down 10 times using a multichannel pipette. 100 µl cell suspension was transferred to a new white transparent bottom 96 well plate (Greiner-bio-one) and 100 µl ONE-Glo™ Luciferase Assay (Promega) was added. After 15 min incubation in the dark on a rotary shaker at 300 rpm and RT luminescence was measured using Tecan® Spark10M plate reader, 1 sec/well as detection time.

The bar diagram shows the activation of anti-CD20-scFab-CD28ATD-CD28CSD-CD3zSSD expressing Jurkat NFAT T cells after 20 hours co-cultivation with SUDHL4 target cells in different E:T ratios. Among the different E:T ratios, the 10:1 and 5:1 E:T ratio show the highest luminescence signal (FIG. 6 black bars). Also anti-CD20-scFab-CD28ATD-CD28CSD-CD3zSSD expressing Jurkat NFAT T cells co-cultured at 10:1 E:T ratio in CD3 antibody coated wells, show a high luminescence signal comparable to the same condition without CD3 stimulus.

Further Jurkat NFAT wild type cells do not show any activation independent of different E:T ratios, but if co-cultivated in 10:1 E:T ratio in CD3 antibody coated wells a clear luminescence signal is delectable, that proves their functionality.

Further control experiments show that target cells or anti-CD20-scFab-CD28ATD-CD28CSD-CD3zSSD expressing T cells alone as well as CD3 antibody coated wells with target cells do not show any activation. Each point represents the mean value of technical triplicates. Standard deviation is indicated by error bars.

Example 4

Described herein is a Jurkat NFAT T cell reporter assay performed using CD20 expressing SUDHDL4 tumor cells as target cells and a sorted pool of anti-CD20-Fab-CD28ATD-CD28CSD-CD3zSSD expressing Jurkat NFAT T cells or anti-CD20-scFv-CD28ATD-CD28CSD-CD3zSSD expressing Jurkat NFAT T cells as target cells (FIG. 7).

As positive control, wells of a 96 well plate (Cellstar Greiner-bio-one, CAT-No. 655185) were coated with 10 µg/ml CD3 antibody (from Biolegend®) in phosphate buffered saline (PBS) either for 4° C. over night or for at least 1h at 37° C. The CD3 antibody coated wells were washed twice with PBS, after the final washing step PBS was fully removed. Jurkat NFAT wild type T cells or Jurkat NFAT T cells engineered to express anti-CD20-Fab-CD28ATD-CD28CSD-CD3zSSD or anti-CD20-scFv-CD28ATD-CD28CSD-CD3zSSD (further termed as reporter cells), were counted and checked for their viability using Cedex HiRes. Cell number was adjusted to $1\times10^6$ viable cells/ml. Therefore an appropriate aliquot of the cell suspension was pelleted at 210 g for 5 min at room temperature (RT) and resuspended in fresh RPMI-160+10% FCS+1% Glutamax (growth medium). Target cells expressing the antigen of interest, were counted and checked for their viability as well. Cell number was adjusted to $1\times10^6$ viable cells/ml in growth medium. Target cells and reporter cells were plated in 10:1, 5:1, 2:1 or 1:1 E:T ratio (110.000 cells per well in total) in triplicates in a 96-well suspension culture plate (Greiner-bio one) in a final volume of 200 µl. After that the 96 well plate was centrifuged for 2 min at 190 g and RT and sealed with Parafilm®.

After 20 hours at 37° C. and 5% $CO_2$ in humidity atmosphere incubation the content of each well was mixed by pipetting up and down 10 times using a multichannel pipette. 100 µl cell suspension was transferred to a new white transparent bottom 96 well plate (Greiner-bio-one) and 100 µl ONE-Glo™ Luciferase Assay (Promega) was added. After 15 min incubation in the dark on a rotary shaker at 300 rpm and RT luminescence was measured using Tecan® Spark10M plate reader, 1 sec/well as detection time.

The bar diagram shows the activation of Anti-CD20-scFv-CD28ATD-CD28CSD-CD3zSSD expressing Jurkat NFAT T cells after 20 hours co-cultivation with SUDHL4 target cells at 5:1 E:T ratio. Anti-CD20-scFv-CD28ATD-CD28CSD-CD3zSSD expressing Jurkat NFAT T cells co-cultured with target cells in CD3 antibody coated wells, showed the highest luminescence signal, which is comparable to the same condition without CD3 stimulus. Surprisingly, the crossFab format leads to differentiated activation of Jurkat NFAT T cells wherein strong activation is found in conjunction with CD3 mediated signaling. Further Jurkat NFAT wild type cells do not show any activation, but if co-cultivated in 10:1 E:T ratio in CD3 antibody coated wells a clear luminescence signal is delectable, that proves their functionality. Each bar represents the mean value of technical triplicates. Standard deviation is indicated by error bars.

Example 5

The two antibody candidates 5E11 and 33H09 were originally selected by means of phage display library screening to bind to the WT1-peptide "RMF" in complex with MHCI. Dilution series of both binders in IgG-format were checked for binding by means of flow cytometry.

Therefore, T2 cells, pulsed with 10 µm target peptide "RMF", 10 µM off-target pepide "VLD" or left unpulsed, were incubated with dilution series of the antibodies for 30 min on ice. After a washing step removing unbound binders, cells were incubated with fluorescently labelled secondary antibody (anti-huFc, Jackson ImmunoResearch), followed by another washing step and detection of remaining antibodies by flow cytometry. Importantly, in this assay both assessed candidates (5E11 and 33H09) appear similar in terms of specificity, with clear concentration-dependent signal on T2 cells pulsed with target peptide "RMF", compared to no binding to T2 cells pulsed with off-target pepide "VLD" or unpulsed T2 cells (FIG. 8).

The same two antibody candidates (5E11 and 33H09) plus two further candidates against the same target peptide/MHC (ESK1 and 11D06) were assessed in a Jurkat NFAT reporter CAR-T cell assay depicted in FIG. 9.

This Jurkat NFAT reporter CAR-T cell assay employs pools of Jurkat NFAT reporter cells that recognize HLA-A2/WT1 peptide RMF via four different Fabs (5E11 (SEQ ID NOs 86 and 87), ESK1, 33H09 (SEQ ID NOs 84 and 85) or 11D06 (SEQ ID NOs 82 and 83), respectively), embedded into chimeric antigen receptors expressed on the cell surface.

Prior to co-incubation with the Jurkat NFAT reporter cells, T2 cells were pulsed with the respective peptide at $10^{-5}$ M for 2 hours at 37° C., or left unpulsed. Target cells and reporter cells were plated in 5:1 E:T ratio (10.000 effector cells per 2000 target cells per well) in triplicates in a 384-well white flat clear bottom plate (Greiner-bio-one). Jurkat NFAT reporter CAR-T cells and target cells were co-incubated for 7 hours at 37° C., followed by addition of 6 μl per well of ONE-Glo™ luciferase substrate (Promega) and direct measurement of luminescence using a TECAN infinite M1000Pro plate reader. The activation of CAR-NFAT-signaling from triplicate measurements on RMF- or VLD-peptide-pulsed T2 cells is expressed as column graph (FIG. 9). Comparison of signals on RMF-peptide (target) vs. VLD-peptide (off-target) and differently pulsed T2 cells incubated with luciferase substrate, but without reporter cells, helps to assess specificity of activation of the respective binder.

Different from the FACS-based screening depicted in FIG. 8, this Jurkat NFAT reporter CAR-T cell assay does clearly discriminate candidates 5E11 and 33H09 in terms of specific T-cell activation on target, as opposed to unspecific activation on off-target.

The background signals of the respective Jurkat NFAT reporter cell pools incubated with luciferease substrate as above, but without any co-incubation with target-cell, is low, as depicted in FIG. 10.

Example 6

This Jurkat NFAT reporter CAR-T cell assay employs pools of Jurkat NFAT reporter cells that recognize two different HLA-A2/peptide targets. Pools F06, F29 and F30 express candidate Fabs that were selected to bind to a blinded peptide/HLA-target, while the pool with Fab 33H09 is specific for HLA-A2/WT1 peptide RMF.

Prior to co-incubation with the Jurkat NFAT reporter cells, T2 cells were pulsed with the respective peptide at $10^{-5}$ M for 2 hours at 37° C., or left unpulsed. Target cells and reporter cells were plated in 5:1 E:T ratio (10.000 effector cells per 2000 target cells per well) in triplicates in a 384-well white flat clear bottom plate (Greiner-bio-one). Jurkat NFAT reporter cells and target cells were co-incubated for 7 hours at 37° C., followed by addition of 6 μl per well of ONE-Glo™ luciferase substrate (Promega) and direct measurement of luminescence using a TECAN infinite M1000Pro plate reader. The activation of CAR-NFAT-signaling from triplicate measurements on T2 cells is expressed as column graph (FIG. 11). Comparison of signals obtained from the four different cell pools on the different peptides indicates the high specificity of activation of the respective candidates towards their desired target peptide/HLA.

Exemplary Sequences

TABLE 2

Anti-CD20 Fab amino acid sequences

| Construct | Protein Sequence | SEQ ID NO |
|---|---|---|
| Anti-CD20 (GA101) CDR H1 Kabat | YSWIN | 1 |
| Anti-CD20 (GA101) CDR H2 Kabat | RIFPGDGDTDYNGKFKG | 2 |
| Anti-CD20 (GA101) CDR H3 Kabat | NVFDGYWLVY | 3 |
| Anti-CD20 (GA101) CDR L1 Kabat | RSSKSLLHSNGITYLY | 4 |
| Anti-CD20 (GA101) CDR L2 Kabat | QMSNLVS | 5 |
| Anti-CD20 (GA101) CDR L3 Kabat | AQNLELPYT | 6 |
| Anti-CD20-(GA101)-Fab heavy chain-CD28ATD-CD28CSD-CD3zSSD fusion pETR 17097 | QVQLVQSGAEVKKPGSSVKVSCKASGYAFSYSWINWVRQAPGQGLEWMGRIFPGDGDTDYNGKFKGRVTITADKSTSTAYMELSSLRSEDTAVYYCARNVFDGYWLVYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCGGGGSFWVLVVVGGVLACYSLLVTVAFIIFWVRSKRSRLLHSDYMNMTPRRPGPTRKHYQPYAPPRDFAAYRSRVKFSRSADAPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR | 7 |

TABLE 2-continued

Anti-CD20 Fab amino acid sequences

| Construct | Protein Sequence | SEQ ID NO |
|---|---|---|
| Anti-CD20-(GA101)-Fab heavy chain | QVQLVQSGAEVKKPGSSVKVSCKASGYAFSYSWINWVR QAPGQGLEWMGRIFPGDGDTDYNGKFKGRVTITADKST STAYMELSSLRSEDTAVYYCARNVFDGYWLVYWGQGT LVTVSSASTKGPSVFPLAPSSKSTSGGTAALGCLVKDYFP EPVTVSWNSGALTSGVHTFPAVLQSSGLYSLSSVVTVPSS SLGTQTYICNVNHKPSNTKVDKKVEPKSC | 8 |
| Anti-CD20-(GA101)-Fab light chain | DIVMTQTPLSLPVTPGEPASISCRSSKSLLHSNGITYLYWY LQKPGQSPQLLIYQMSNLVSGVPDRFSGSGSGTDFTLKIS RVEAEDVGVYYCAQNLELPYTFGGGTKVEIKRTVAAPS VFIFPPSDEQLKSGTASVVCLLNNFYPREAKVQWKVDNA LQSGNSQESVTEQDSKDSTYSLSSTLTLSKADYEKHKVY ACEVTHQGLSSPVTKSFNRGEC | 9 |
| Anti-CD20-(GA101) VL | DIVMTQTPLSLPVTPGEPASISCRSSKSLLHSNGITYLYWY LQKPGQSPQLLIYQMSNLVSGVPDRFSGSGSGTDFTLKIS RVEAEDVGVYYCAQNLELPYTFGGGTKVEIK | 10 |
| CL | RTVAAPSVFIFPPSDEQLKSGTASVVCLLNNFYPREAKVQ WKVDNALQSGNSQESVTEQDSKDSTYSLSSTLTLSKADY EKHKVYACEVTHQGLSSPVTKSFNRGEC | 11 |
| Anti-CD20-(GA101) VH | QVQLVQSGAEVKKPGSSVKVSCKASGYAFSYSWINWVR QAPGQGLEWMGRIFPGDGDTDYNGKFKGRVTITADKST STAYMELSSLRSEDTAVYYCARNVFDGYWLVYWGQGT LVTVSS | 12 |
| CH1 | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSC | 13 |
| CD28ATD | FWVLVVVGGVLACYSLLVTVAFIIFWV | 14 |
| CD28CSD | RSKRSRLLHSDYMNMTPRRPGPTRKHYQPYAPPRDFAA YRS | 15 |
| CD3zSSD | RVKFSRSADAPAYQQGQNQLYNELNLGRREEYDVLDKR RGRDPEMGGKPRRKNPQEGLYNELQKDKMAEAYSEIG MKGERRRGKGHDGLYQGLSTATKDTYDALHMQALPPR | 16 |
| CD28ATD-CD28CSD-CD3zSSD | FWVLVVVGGVLACYSLLVTVAFIIFWVRSKRSRLLHSDY MNMTPRRPGPTRKHYQPYAPPRDFAAYRSRVKFSRSAD APAYQQGQNQLYNELNLGRREEYDVLDKRRGRDPEMG GKPRRKNPQEGLYNELQKDKMAEAYSEIGMKGERRRGK GHDGLYQGLSTATKDTYDALHMQALPPR | 17 |
| eGFP | VSKGEELFTGVVPILVELDGDVNGHKFSVSGEGEGDATY GKLTLKFICTTGKLPVPWPTLVTTLTYGVQCFSRYPDHM KQHDFFKSAMPEGYVQERTIFFKDDGNYKTRAEVKFEG DTLVNRIELKGIDFKEDGNILGHKLEYNYNSHNVYIMAD KQKNGIKVNFKIRHNIEDGSVQLADHYQQNTPIGDGPVL LPDNHYLSTQSALSKDPNEKRDHMVLLEFVTAAGITLGM DELYK | 18 |
| (G4S)4 linker | GGGGSGGGGSGGGGSGGGGS | 19 |
| G4S linker | GGGGS | 20 |
| T2A linker | GEGRGSLLTCGDVEENPGP | 21 |

TABLE 3

Anti-CD20 Fab DNA sequences

| Construct | DNA Sequenz | SEQ ID NO |
|---|---|---|
| Anti-CD20-(GA101)-Fab-CD28ATD-CD28CSD- | ATGGGATGGAGCTGTATCATCCTCTTCTTGGTAGCAAC AGCTACCGGTGTGCATTCCGATATCGTGATGACCCAG ACTCCACTCTCCCTGCCCGTCACCCCTGGAGAGCCCGC CAGCATTAGCTGCAGGTCTAGCAAGAGCCTCTTGCAC | 22 |

TABLE 3-continued

Anti-CD20 Fab DNA sequences

| Construct | DNA Sequenz | SEQ ID NO |
|---|---|---|
| CD3zSSD pETR17097 | AGCAATGGCATCACTTATTTGTATTGGTACCTGCAAAA GCCAGGGCAGTCTCCACAGCTCCTGATTTATCAAATGT CCAACCTTGTCTCTGGCGTCCCTGACCGGTTCTCCGGA TCCGGGTCAGGCACTGATTTCACACTGAAAATCAGCA GGGTGGAGGCTGAGGATGTTGGAGTTTATTACTGCGC TCAGAATCTAGAACTTCCTTACACCTTCGGCGGAGGG ACCAAGGTGGAGATCAAACCGTACGGTGGCTGCACCA TCTGTCTTCATCTTCCCGCCATCTGATGAGCAGTTGAA ATCTGGAACTGCCTCTGTTGTGTGCCTGCTGAATAACT TCTATCCCAGAGAGGCCAAAGTACAGTGGAAGGTGGA TAACGCCCTCCAATCGGGTAACTCCCAGGAGAGTGTC ACAGAGCAGGACAGCAAGGACAGCACCTACAGCCTCA GCAGCACCCTGACGCTGAGCAAAGCAGACTACGAGAA ACACAAAGTCTACGCCTGCGAAGTCACCCATCAGGGC CTGAGCTCGCCCGTCACAAAGAGCTTCAACAGGGGAG AGTGTTAGAATAGAATTCCCCGAAGTAACTTAGAAGC TGTAAATCAACGATCAATAGCAGGTGTGGCACACCAG TCATACCTTGATCAAGCACTTCTGTTTCCCCGGACTGA GTATCAATAGGCTGCTCGCGGGCTGAAGGAGAAAAC GTTCGTTACCCGACCAACTACTTCGAGAAGCTTAGTAC CACCATGAACGAGGCAGGGTGTTTCGCTCAGCACAAC CCCAGTGTAGATCAGGCTGATGAGTCACTGCAACCCC CATGGGCGACCATGGCAGTGGCTGCGTTGGCGGCCTG CCCATGGAGAAATCCATGGGACGCTCTAATTCTGACA TGGTGTGAAGTGCCTATTGAGCTAACTGGTAGTCCTCC GGCCCCTGATTGCGGCTAATCCTAACTGCGGAGCACA TGCTCACAAACCAGTGGGTGGTGTGTCGTAACGGGCA ACTCTGCAGCGGAACCGACTACTTTGGGTGTCCGTGTT TCCTTTTATTCCTATATTGGCTGCTTATGGTGACAATCA AAAAGTTGTTACCATATAGCTATTGGATTGGCCATCCG GTGTGCAACAGGGCAACTGTTTACCTATTTATTGGTTT TGTACCATTATCACTGAAGTCTGTGATCACTCTCAAAT TCATTTTGACCCTCAACACAATCAAACGCCACCATGGG ATGGAGCTGTATCATCCTCTTCTTGGTAGCAACAGCTA CCGGTGTGCACTCCCAGGTGCAATTGGTGCAGTCTGGC GCTGAAGTTAAGAAGCCTGGGAGTTCAGTGAAGGTCT CCTGCAAGGCTTCGGGATACGCCTTCAGCTATTCTTGG ATCAATTGGGTGCGGCAGGCGCCTGGACAAGGGCTCG AGTGGATGGGACGGATCTTTCCCGGCGATGGGGATAC TGACTACAATGGGAAATTCAAGGGCAGAGTCACAATT ACCGCCGACAAATCCACTAGCACAGCCTATATGGAGC TGAGCAGCCTGAGATCTGAGGACACGGCCGTGTATTA CTGTGCAAGAAATGTCTTTGATGGTTACTGGCTTGTTT ACTGGGGCCAGGGAACCCTGGTCACCGTCTCCAGCGC TAGCACCAAGGGCCCCTCCGTGTTCCCCCTGGCCCCCA GCAGCAAGAGCACCAGCGGCGGCACAGCCGCTCTGGG CTGCCTGGTCAAGGACTACTTCCCCGAGCCCGTGACCG TGTCCTGGAACAGCGGAGCCCTGACCTCCGGCGTGCA CACCTTCCCCGCCGTGCTGCAGAGTTCTGGCCTGTATA GCCTGAGCAGCGTGGTCACCGTGCCTTCTAGCAGCCTG GGCACCCAGACCTACATCTGCAACGTGAACCACAAGC CCAGCAACACCAAGGTGGACAAGAAGGTGGAGCCCA AGAGCTGCGGAGGGGGCGGATCCTTCTGGGTGCTGGT GGTGGTGGGCGGCGTGCTGGCCTGCTACAGCCTGCTG GTGACCGTGGCCTTCATCATCTTCTGGGTGAGGAGCAA GAGGAGCAGGCTGCTGCACAGCGACTACATGAACATG ACCCCCAGGAGGCCCGGCCCCACCAGGAAGCACTACC AGCCCTACGCCCCCCCCAGGGACTTCGCCGCCTACAG GAGCAGGGTGAAGTTCAGCAGGAGCGCCGACGCCCCC GCCTACCAGCAGGGCCAGAACCAGCTGTATAACGAGC TGAACCTGGGCAGGAGGGAGGAGTACGACGTGCTGGA CAAGAGGAGGGGCAGGGACCCCGAGATGGGCGGCAA GCCCAGGAGGAAGAACCCCCAGGAGGGCCTGTATAAC GAGCTGCAGAAGGACAAGATGGCCGAGGCCTACAGC GAGATCGGCATGAAGGGCGAGAGGAGGAGGGGCAAG GGCCACGACGGCCTGTACCAGGGCCTGAGCACCGCCA CCAAGGACACCTACGACGCCCTGCACATGCAGGCCCT GCCCCCCAGG | |
| Anti-CD20-(GA101)-Fab-VL | GATATCGTGATGACCCAGACTCCACTCTCCCTGCCCGT CACCCCTGGAGAGCCCGCCAGCATTAGCTGCAGGTCT AGCAAGAGCCTCTTGCACAGCAATGGCATCACTTATTT GTATTGGTACCTGCAAAAGCCAGGGCAGTCTCCACAG CTCCTGATTTATCAAATGTCCAACCTTGTCTCTGGCGT CCCTGACCGGTTCTCCGGATCCGGGTCAGGCACTGATT | 23 |

TABLE 3-continued

Anti-CD20 Fab DNA sequences

| Construct | DNA Sequenz | SEQ ID NO |
|---|---|---|
| | TCACACTGAAAATCAGCAGGGTGGAGGCTGAGGATGT TGGAGTTTATTACTGCGCTCAGAATCTAGAACTTCCTT ACACCTTCGGCGGAGGGACCAAGGTGGAGATCAAA | |
| Fab CL | CGTACGGTGGCTGCACCATCTGTCTTCATCTTCCCGCC ATCTGATGAGCAGTTGAAATCTGGAACTGCCTCTGTTG TGTGCCTGCTGAATAACTTCTATCCCAGAGAGGCCAA AGTACAGTGGAAGGTGGATAACGCCCTCCAATCGGGT AACTCCCAGGAGAGTGTCACAGAGCAGGACAGCAAG GACAGCACCTACAGCCTCAGCAGCACCCTGACGCTGA GCAAAGCAGACTACGAGAAACACAAAGTCTACGCCTG CGAAGTCACCCATCAGGGCCTGAGCTCGCCCGTCACA AAGAGCTTCAACAGGGGAGAGTGTTAG | 24 |
| Anti-CD20-(GA101)-Fab-VH | CAGGTGCAATTGGTGCAGTCTGGCGCTGAAGTTAAGA AGCCTGGGAGTTCAGTGAAGGTCTCCTGCAAGGCTTC GGGATACGCCTTCAGCTATTCTTGGATCAATTGGGTGC GGCAGGCGCCTGGACAAGGGCTCGAGTGGATGGGACG GATCTTTCCCGGCGATGGGGATACTGACTACAATGGG AAATTCAAGGGCAGAGTCACAATTACCGCCGACAAAT CCACTAGCACAGCCTATATGGAGCTGAGCAGCCTGAG ATCTGAGGACACGGCCGTGTATTACTGTGCAAGAAAT GTCTTTGATGGTTACTGGCTTGTTTACTGGGGCCAGGG AACCCTGGTCACCGTCTCCAGC | 25 |
| Fab CH1 | GCTAGCACCAAGGGCCCCTCCGTGTTCCCCCTGGCCCC CAGCAGCAAGAGCACCAGCGGCGGCACAGCCGCTCTG GGCTGCCTGGTCAAGGACTACTTCCCCGAGCCCGTGA CCGTGTCCTGGAACAGCGGAGCCCTGACCTCCGGCGT GCACACCTTCCCCGCCGTGCTGCAGAGTTCTGGCCTGT ATAGCCTGAGCAGCGTGGTCACCGTGCCTTCTAGCAG CCTGGGCACCCAGACCTACATCTGCAACGTGAACCAC AAGCCCAGCAACACCAAGGTGGACAAGAAGGTGGAG CCCAAGAGCTGC | 26 |
| IRES EV71 internal ribosomal entry side | CCCGAAGTAACTTAGAAGCTGTAAATCAACGATCAAT AGCAGGTGTGGCACACCAGTCATACCTTGATCAAGCA CTTCTGTTTCCCCGGACTGAGTATCAATAGGCTGCTCG CGCGGCTGAAGGAGAAAACGTTCGTTACCCGACCAAC TACTTCGAGAAGCTTAGTACCACCATGAACGAGGCAG GGTGTTTCGCTCAGCACAACCCCAGTGTAGATCAGGCT GATGAGTCACTGCAACCCCCATGGGCGACCATGGCAG TGGCTGCGTTGGCGGCCTGCCCATGGAGAAATCCATG GGACGCTCTAATTCTGACATGGTGTGAAGTGCCTATTG AGCTAACTGGTAGTCCTCCGGCCCCTGATTGCGGCTAA TCCTAACTGCGGAGCACATGCTCACAAACCAGTGGGT GGTGTGTCGTAACGGGCAACTCTGCAGCGGAACCGAC TACTTTGGGTGTCCGTGTTTCCTTTTATTCCTATATTGG CTGCTTATGGTGACAATCAAAAAGTTGTTACCATATAG CTATTGGATTGGCCATCCGGTGTGCAACAGGGCAACT GTTTACCTATTTATTGGTTTTGTACCATTATACTGAAG TCTGTGATCACTCTCAAATTCATTTTGACCCTCAACAC AATCAAAC | 27 |
| G4S linker | GGAGGGGGCGGATCC | 28 |
| CD28ATD | TTTTGGGTGCTGGTGGTGGTTGGTGGAGTCCTGGCTTG CTATAGCTTGCTAGTAACAGTGGCCTTTATTATTTTCT GGGTG | 29 |
| CD28CSD | AGGAGTAAGAGGAGCAGGCTCCTGCACAGTGACTACA TGAACATGACTCCCCGCCGCCCCGGGCCCACCCGCAA GCATTACCAGCCCTATGCCCCACCACGCGACTTCGCAG CCTATCGCTCC | 30 |
| CD3zSSD | AGAGTGAAGTTCAGCAGGAGCGCAGACGCCCCCGCGT ACCAGCAGGGCCAGAACCAGCTCTATAACGAGCTCAA TCTAGGACGAAGAGAGGAGTACGATGTTTTGGACAAG AGACGTGGCCGGGACCCTGAGATGGGGGGAAAGCCG AGAAGGAAGAACCCTCAGGAAGGCCTGTACAATGAAC TGCAGAAAGATAAGATGGCGGAGGCCTACAGTGAGAT TGGGATGAAAGGCGAGCGCCGGAGGGGCAAGGGGCA CGATGGCCTTTACCAGGGTCTCAGTACAGCCACCAAG GACACCTACGACGCCCTTCACATGCAGGCCCTGCCCCC TCGC | 31 |

TABLE 3-continued

Anti-CD20 Fab DNA sequences

| Construct | DNA Sequenz | SEQ ID NO |
|---|---|---|
| CD28ATD-CD28CSD-CD3zSSD | TTCTGGGTGCTGGTGGTGGTGGGCGGCGTGCTGGCCTG CTACAGCCTGCTGGTGACCGTGGCCTTCATCATCTTCT GGGTGAGGAGCAAGAGGAGCAGGCTGCTGCACAGCG ACTACATGAACATGACCCCCAGGAGGCCCGGCCCCAC CAGGAAGCACTACCAGCCCTACGCCCCCCCCAGGGAC TTCGCCGCCTACAGGAGCAGGGTGAAGTTCAGCAGGA GCGCCGACGCCCCCGCCTACCAGGGCCAGAACCA GCTGTATAACGAGCTGAACCTGGGCAGGAGGGAGGAG TACGACGTGCTGGACAAGAGGAGGGGCAGGGACCCC GAGATGGGCGGCAAGCCCAGGAGGAAGAACCCCCAG GAGGGCCTGTATAACGAGCTGCAGAAGGACAAGATGG CCGAGGCCTACAGCGAGATCGGCATGAAGGGCGAGA GGAGGAGGGGCAAGGGCCACGACGGCCTGTACCAGG GCCTGAGCACCGCCACCAAGGACACCTACGACGCCCT GCACATGCAGGCCCTGCCCCCCAGG | 32 |
| T2A linker | TCCGGAGAGGGCAGAGGAAGTCTTCTAACATGCGGTG ACGTGGAGGAGAATCCCGGCCCTAGG | 33 |
| eGFP | GTGAGCAAGGGCGAGGAGCTGTTCACCGGGGTGGTGC CCATCCTGGTCGAGCTGGACGGCGACGTAAACGGCCA CAAGTTCAGCGTGTCCGGCGAGGGCGAGGGCGATGCC ACCTACGGCAAGCTGACCCTGAAGTTCATCTGCACCA CCGGCAAGCTGCCCGTGCCCTGGCCCACCCTCGTGACC ACCCTGACCTACGGCGTGCAGTGCTTCAGCCGCTACCC CGACCACATGAAGCAGCACGACTTCTTCAAGTCCGCC ATGCCCGAAGGCTACGTCCAGGAGCGCACCATCTTCTT CAAGGACGACGGCAACTACAAGACCCGCGCCGAGGTG AAGTTCGAGGGCGACACCCTGGTGAACCGCATCGAGC TGAAGGGCATCGACTTCAAGGAGGACGGCAACATCCT GGGGCACAAGCTGGAGTACAACTACAACAGCCACAAC GTCTATATCATGGCCGACAAGCAGAAGAACGGCATCA AGGTGAACTTCAAGATCCGCCACAACATCGAGGACGG CAGCGTGCAGCTCGCCGACCACTACCAGCAGAACACC CCCATCGGCGACGGCCCCGTGCTGCTGCCCGACAACC ACTACCTGAGCACCCAGTCCGCCCTGAGCAAAGACCCC CAACGAGAAGCGCGATCACATGGTCCTGCTGGAGTTC GTGACCGCCGCCGGGATCACTCTCGGCATGGACGAGC TGTACAAGTGA | 34 |
| Anti-CD20-(GA101)-Fab-CD28ATD-CD28CSD-CD3zSSD-eGFP pETR17097 | ATGGGATGGAGCTGTATCATCCTCTTCTTGGTAGCAAC AGCTACCGGTGTGCATTCCGATATCGTGATGACCCAG ACTCCACTCTCCCTGCCCGTCACCCCTGGAGAGCCCGC CAGCATTAGCTGCAGGTCTAGCAAGAGCCTCTTGCAC AGCAATGGCATCACTTATTTGTATTGGTACCTGCAAAA GCCAGGGCAGTCTCCACAGCTCCTGATTTATCAAATGT CCAACCTTGTCTCTGGCGTCCCTGACCGGTTCTCCGGA TCCGGGTCAGGCACTGATTTCACACTGAAAATCAGCA GGGTGGAGGCTGAGGATGTTGGAGTTTATTACTGCGC TCAGAATCTAGAACTTCCTTACACCTTCGGCGGAGGG ACCAAGGTGGAGATCAAACGTACGGTGGCTGCACCAT CTGTCTTCATCTTCCCGCCATCTGATGAGCAGTTGAAA TCTGGAACTGCCTCTGTTGTGTGCCTGCTGAATAACTT CTATCCCAGAGAGGCCAAAGTACAGTGGAAGGTGGAT AACGCCCTCCAATCGGGTAACTCCCAGGAGAGTGTCA CAGAGCAGGACAGCAAGGACAGCACCTACAGCCTCAG CAGCACCCTGACGCTGAGCAAAGCAGACTACGAGAAA CACAAAGTCTACGCCTGCGAAGTCACCCATCAGGGCC TGAGCTCGCCCGTCACAAAGAGCTTCAACAGGGGAGA GTGTTAGAATAGAATTCCCCGAAGTAACTTAGAAGCT GTAAATCAACGATCAATAGCAGGTGTGGCACACCAGT CATACCTTGATCAAGCACTTCTGTTTCCCCGGACTGAG TATCAATAGGCTGCTCGCGCGGCTGAAGGAGAAAACG TTCGTTACCCGACCAACTACTTCGAGAAGCTTAGTACC ACCATGAACGAGGCAGGGTGTTTCGCTCAGCACAACC CCAGTGTAGATCAGGCTGATGAGTCACTGCAACCCCC ATGGGCGACCATGGCAGTGGCTGCGTTGGCGGCCTGC CCATGGAGAAATCCATGGGACGCTCTAATTCTGACAT GGTGTGAAGTGCCTATTGAGCTAACTGGTAGTCCTCCG GCCCCTGATTGCGGCTAATCCTAACTGCGGAGCACAT GCTCACAAACCAGTGGGTGGTGTGTCGTAACGGGCAA CTCTGCAGCGGAACCGACTACTTTGGGTGTCCGTGTTT CCTTTTATTCCTATATTGGCTGCTTATGGTGACAATCA AAAAGTTGTTACCATATAGCTATTGGATTGGCCATCCG | 35 |

TABLE 3-continued

Anti-CD20 Fab DNA sequences

| Construct | DNA Sequenz | SEQ ID NO |
|---|---|---|
| | GTGTGCAACAGGGCAACTGTTTACCTATTTATTGGTTT<br>TGTACCATTATCACTGAAGTCTGTGATCACTCTCAAAT<br>TCATTTTGACCCTCAACACAATCAAACGCCACCATGGG<br>ATGGAGCTGTATCATCCTCTTCTTGGTAGCAACAGCTA<br>CCGGTGTGCACTCCCAGGTGCAATTGGTGCAGTCTGGC<br>GCTGAAGTTAAGAAGCCTGGGAGTTCAGTGAAGGTCT<br>CCTGCAAGGCTTCGGGATACGCCTTCAGCTATTCTTGG<br>ATCAATTGGGTGCGGCAGGCGCCTGGACAAGGGCTCG<br>AGTGGATGGGACGGATCTTTCCCGGCGATGGGGATAC<br>TGACTACAATGGGAAATTCAAGGGCAGAGTCACAATT<br>ACCGCCGACAAATCCACTAGCACAGCCTATATGGAGC<br>TGAGCAGCCTGAGATCTGAGGACACGGCCGTGTATTA<br>CTGTGCAAGAAATGTCTTTGATGGTTACTGGCTTGTTT<br>ACTGGGGCCAGGGAACCCTGGTCACCGTCTCCAGCGC<br>TAGCACCAAGGGCCCCTCCGTGTTCCCCCTGGCCCCCA<br>GCAGCAAGAGCACCAGCGGCGGCACAGCCGCTCTGGG<br>CTGCCTGGTCAAGGACTACTTCCCCGAGCCCGTGACCG<br>TGTCCTGGAACAGCGGAGCCCTGACCTCCGGCGTGCA<br>CACCTTCCCCGCCGTGCTGCAGAGTTCTGGCCTGTATA<br>GCCTGAGCAGCGTGGTCACCGTGCCTTCTAGCAGCCTG<br>GGCACCCAGACCTACATCTGCAACGTGAACCACAAGC<br>CCAGCAACACCAAGGTGGACAAGAAGGTGGAGCCCA<br>AGAGCTGCGGAGGGGCGGATCCTTCTGGGTGCTGGT<br>GGTGGTGGGCGGCGTGCTGGCCTGCTACAGCCTGCTG<br>GTGACCGTGGCCTTCATCATCTTCTGGGTGAGGAGCAA<br>GAGGAGCAGGCTGCTGCACAGCGACTACATGAACATG<br>ACCCCCAGGAGGCCCGGCCCCACCAGGAAGCACTACC<br>AGCCCTACGCCCCCCCCAGGGACTTCGCCGCCTACAG<br>GAGCAGGGTGAAGTTCAGCAGGAGCGCCGACGCCCCC<br>GCCTACCAGCAGGGCCAGAACCAGCTGTATAACGAGC<br>TGAACCTGGGCAGGAGGGAGGAGTACGACGTGCTGGA<br>CAAGAGGAGGGGCAGGGACCCCGAGATGGGCGGCAA<br>GCCCAGGAGGAAGAACCCCCAGGAGGGCCTGTATAAC<br>GAGCTGCAGAAGGACAAGATGGCCGAGGCCTACAGC<br>GAGATCGGCATGAAGGGCGAGAGGAGGAGGGGCAAG<br>GGCCACGACGGCCTGTACCAGGGCCTGAGCACCGCCA<br>CCAAGGACACCTACGACGCCCTGCACATGCAGGCCCT<br>GCCCCCCAGGTCCGGAGAGGGCAGAGGAAGTCTTCTA<br>ACATGCGGTGACGTGGAGGAGAATCCCGGCCCTAGGG<br>TGAGCAAGGGCGAGGAGCTGTTCACCGGGGTGGTGCC<br>CATCCTGGTCGAGCTGGACGGCGACGTAAACGGCCAC<br>AAGTTCAGCGTGTCCGGCGAGGGCGAGGGCGATGCCA<br>CCTACGGCAAGCTGACCCTGAAGTTCATCTGCACCACC<br>GGCAAGCTGCCCGTGCCCTGGCCCACCCTCGTGACCA<br>CCCTGACCTACGGCGTGCAGTGCTTCAGCCGCTACCCC<br>GACCACATGAAGCAGCACGACTTCTTCAAGTCCGCCA<br>TGCCCGAAGGCTACGTCCAGGAGCGCACCATCTTCTTC<br>AAGGACGACGGCAACTACAAGACCCGCGCCGAGGTG<br>AAGTTCGAGGGCGACACCCTGGTGAACCGCATCGAGC<br>TGAAGGGCATCGACTTCAAGGAGGACGGCAACATCCT<br>GGGGCACAAGCTGGAGTACAACTACAACAGCCACAAC<br>GTCTATATCATGGCCGACAAGCAGAAGAACGGCATCA<br>AGGTGAACTTCAAGATCCGCCACAACATCGAGGACGG<br>CAGCGTGCAGCTCGCCGACCACTACCAGCAGAACACC<br>CCCATCGGCGACGGCCCCGTGCTGCTGCCCGACAACC<br>ACTACCTGAGCACCCAGTCCGCCCTGAGCAAAGACCC<br>CAACGAGAAGCGCGATCACATGGTCCTGCTGGAGTTC<br>GTGACCGCCGCCGGGATCACTCTCGGCATGGACGAGC<br>TGTACAAGTGA | |

TABLE 4

Anti-CD20 crossFab (VH-CL-ATD) amino acid sequences

| Construct | Protein Sequence | SEQ ID NO |
|---|---|---|
| Anti-CD20 (GA101) CDR H1 Kabat | see Table 2 | 1 |
| Anti-CD20 (GA101) CDR H2 Kabat | see Table 2 | 2 |

TABLE 4-continued

Anti-CD20 crossFab (VH-CL-ATD) amino acid sequences

| Construct | Protein Sequence | SEQ ID NO |
|---|---|---|
| Anti-CD20 (GA101) CDR H3 Kabat | see Table 2 | 3 |
| Anti-CD20 (GA101) CDR L1 Kabat | see Table 2 | 4 |
| Anti-CD20 (GA101) CDR L2 Kabat | see Table 2 | 5 |
| Anti-CD20 (GA101) CDR L3 Kabat | see Table 2 | 6 |
| Anti-CD20-(GA101)-crossFab VH-CL light chain-ATD-CD28ATD-CD28CSD-CD3zSSD fusion pETR17098 | QVQLVQSGAEVKKPGSSVKVSCKASGYAFSYSWINWVR QAPGQGLEWMGRIFPGDGDTDYNGKFKGRVTITADKST STAYMELSSLRSEDTAVYYCARNVFDGYWLVYWGQGT LVTVSSASVAAPSVFIFPPSDEQLKSGTASVVCLLNNFYP REAKVQWKVDNALQSGNSQESVTEQDSKDSTYSLSSTL TLSKADYEKHKVYACEVTHQGLSSPVTKSFNRGECGGG GSFWVLVVVGGVLACYSLLVTVAFIIFWVRSKRSRLLHS DYMNMTPRRPGPTRKHYQPYAPPRDFAAYRSVKFSRS ADAPAYQQGQNQLYNELNLGRREEYDVLDKRRGRDPE MGGKPRRKNPQEGLYNELQKDKMAEAYSEIGMKGERR RGKGHDGLYQGLSTATKDTYDALHMQALPPR | 36 |
| Anti-CD20-(GA101)-crossFab VH-CL light chain pETR17098 | QVQLVQSGAEVKKPGSSVKVSCKASGYAFSYSWINWVR QAPGQGLEWMGRIFPGDGDTDYNGKFKGRVTITADKST STAYMELSSLRSEDTAVYYCARNVFDGYWLVYWGQGT LVTVSSASVAAPSVFIFPPSDEQLKSGTASVVCLLNNFYP REAKVQWKVDNALQSGNSQESVTEQDSKDSTYSLSSTL TLSKADYEKHKVYACEVTHQGLSSPVTKSFNRGEC | 37 |
| Anti-CD20-(GA101)-crossFab VL-CH1 heavy chain-pETR17098 | DIVMTQTPLSLPVTPGEPASISCRSSKSLLHSNGITYLYW YLQKPGQSPQLLIYQMSNLVSGVPDRFSGSGSGTDFTLKIS RVEAEDVGVYYCAQNLELPYTFGGGTKVEIKSSASTKGP SVFPLAPSSKSTSGGTAALGCLVKDYFPEPVTVSWNSGA LTSGVHTFPAVLQSSGLYSLSSVVTVPSSSLGTQTYICNV NHKPSNTKVDKKVEPKSC | 38 |
| Anti-CD20-(GA101) VH | see Table 2 | 12 |
| crossFab CL | ASVAAPSVFIFPPSDEQLKSGTASVVCLLNNFYPREAKVQ WKVDNALQSGNSQESVIEQDSKDSTYSLSSTLTLSKADY EKHKVYACEVTHQGLSSPVTKSFNRGEC | 39 |
| Anti-CD20-(GA101)-VL | see Table 2 | 10 |
| crossFab CH1 | SSASTKGPSVFPLAPSSKSTSGGTAALGCLVKDYFPEPVT VSWNSGALTSGVHTFPAVLQSSGLYSLSSVVTVPSSSLGT QTYICNVNHKPSNTKVDKKVEPKSC | 40 |
| G4S linker | see Table 2 | 20 |
| CD28ATD-CD28CSD-CD3zSSD | see Table 2 | 17 |
| T2A linker | see Table 2 | 21 |
| eGFP | see Table 2 | 18 |

TABLE 5

Anti-CD20 crossFab (VL-CH1-ATD) amino acid sequences

| Construct | Protein Sequence | SEQ ID NO |
|---|---|---|
| Anti-CD20 (GA101) CDR H1 Kabat | see Table 2 | 1 |
| Anti-CD20 (GA101) CDR H2 Kabat | see Table 2 | 2 |

TABLE 5-continued

Anti-CD20 crossFab (VL-CH1-ATD) amino acid sequences

| Construct | Protein Sequence | SEQ ID NO |
|---|---|---|
| Anti-CD20 (GA101) CDR H3 Kabat | see Table 2 | 3 |
| Anti-CD20 (GA101) CDR L1 Kabat | see Table 2 | 4 |
| Anti-CD20 (GA101) CDR L2 Kabat | see Table 2 | 5 |
| Anti-CD20 (GA101) CDR L3 Kabat | see Table 2 | 6 |
| Anti-CD20-(GA101)-crossFab VL-CH1 heavy-chain-AM-CD28ATD-CD28CSD-CD3zSSD fusion | DIVMTQTPLSLPVTPGEPASISCRSSKSLLHSNGITYLYWY LQKPGQSPQLLIYQMSNLVSGVPDRFSGSGSGTDFTLKIS RVEAEDVGVYYCAQNLELPYTFGGGTKVEIKSSASTKGP SVFPLAPSSKSTSGGTAALGCLVKDYFPEPVTVSWNSGA LTSGVHTFPAVLQSSGLYSLSSVVTVPSSSLGTQTYICNV NHKPSNTKVDKKVEPKSCGGGGSFWVLVVVGGVLACY SLLVTVAFIIFWVRSKRSRLLHSDYMNMTPRRPGPTRKH YQPYAPPRDFAAYRSRVKFSRSADAPAYQQGQNQLYNE LNLGRREEYDVLDKRRGRDPEMGGKPRRKNPQEGLYNE LQKDKMAEAYSEIGMKGERRRGKGHDGLYQGLSTATK DTYDALHMQALPPR | 41 |
| Anti-CD20-(GA101)-crossFab VL-CH1 heavy chain | DIVMTQTPLSLPVTPGEPASISCRSSKSLLHSNGITYLYWY LQKPGQSPQLLIYQMSNLVSGVPDRFSGSGSGTDFTLKIS RVEAEDVGVYYCAQNLELPYTFGGGTKVEIKSSASTKGP SVFPLAPSSKSTSGGTAALGCLVKDYFPEPVTVSWNSGA LTSGVHTFPAVLQSSGLYSLSSVVTVPSSSLGTQTYICNV NHKPSNTKVDKKVEPKSC | 42 |
| Anti-CD 20-(GA101)-crossFab VH-CL light chain | QVQLVQSGAEVKKPGSSVKVSCKASGYAFSYSWINWVR QAPGQGLEWMGRIFPGDGDTDYNGKFKGRVTITADKST STAYMELSSLRSEDTAVYYCARNVFDGYWLVYWGQGT LVTVSSASVAAPSVFIFPPSDEQLKSGTASVVCLLNNFYP REAKVQWKVDNALQSGNSQESVTEQDSKDSTYSLSSTL TLSKADYEKHKVYACEVTHQGLSSPVTKSFNRGEC | 43 |
| Anti-CD20-(GA101) VH | see Table 2 | 12 |
| crossFab CL | ASVAAPSVFIFPPSDEQLKSGTASVVCLLNNFYPREAKVQ WKVDNALQSGNSQESVIEQDSKDSTYSLSSTLTLSKADY EKHKVYACEVTHQGLSSPVTKSFNRGEC | 44 |
| Anti-CD20-(GA101)-VL | see Table 2 | 10 |
| crossFab CH1 | SSASTKGPSVFPLAPSSKSTSGGTAALGCLVKDYFPEPVT VSWNSGALTSGVHTFPAVLQSSGLYSLSSVVTVPSSSLGT QTYICNVNHKPSNTKVDKKVEPKSC | 45 |
| G4S linker | see Table 2 | 20 |
| CD28ATD-CD28CSD-CD3zSSD | see Table 2 | 17 |
| T2A linker | see Table 2 | 21 |
| eGFP | see Table 2 | 18 |

TABLE 6

Anti-CD20 crossFab (VH-CL-ATD) DNA sequences

| Construct | DNA Sequenz | SEQ ID NO |
|---|---|---|
| Anti-CD20-(GA101)-crossFabVH-CL CD28ATD-CD28CSD-CD3zSSD pETR17098 | ATGGGATGGAGCTGTATCATCCTCTTCTTGGTAGCAAC AGCTACCGGTGTGCATTCCCAGGTGCAATTGGTGCAGT CTGGCGCTGAAGTTAAGAAGCCTGGGAGTTCAGTGAA GGTCTCCTGCAAGGCTTCCGGATACGCCTTCAGCTATT CTTGGATCAATTGGGTGCGGCAGGCGCCTGGACAAGG GCTCGAGTGGATGGGACGGATCTTTCCCGGCGATGGG | 46 |

TABLE 6-continued

Anti-CD20 crossFab (VH-CL-ATD) DNA sequences

| Construct | DNA Sequenz | SEQ ID NO |
|---|---|---|
| | GATACTGACTACAATGGGAAATTCAAGGGCAGAGTCA<br>CAATTACCGCCGACAAATCCACTAGCACAGCCTATAT<br>GGAGCTGAGCAGCCTGAGATCTGAGGACACGGCCGTG<br>TATTACTGTGCAAGAAATGTCTTTGATGGTTACTGGCT<br>TGTTTACTGGGGCCAGGGAACCCTGGTCACCGTCTCCT<br>CAGCTAGCGTGGCCGCTCCCTCCGTGTTCATCTTCCCA<br>CCTTCCGACGAGCAGCTGAAGTCCGGCACCGCTTCTGT<br>CGTGTGCCTGCTGAACAACTTCTACCCCCGCGAGGCCA<br>AGGTGCAGTGGAAGGTGGACAACGCCCTGCAGTCCGG<br>CAACAGCCAGGAATCCGTGACCGAGCAGGACTCCAAG<br>GACAGCACCTACTCCCTGTCCTCCACCCTGACCCTGTC<br>CAAGGCCGACTACGAGAAGCACAAGGTGTACGCCTGC<br>GAAGTGACCCACCAGGGCCTGTCTAGCCCCGTGACCA<br>AGTCTTTCAACCGGGGCGAGTGCTGATAAGGAATTCC<br>CCGAAGTAACTTAGAAGCTGTAAATCAACGATCAATA<br>GCAGGTGTGGCACACCAGTCATACCTTGATCAAGCAC<br>TTCTGTTTCCCCGGACTGAGTATCAATAGGCTGCTCGC<br>GCGGCTGAAGGAGAAAACGTTCGTTACCCGACCAACT<br>ACTTCGAGAAGCTTAGTACCACCATGAACGAGGCAGG<br>GTGTTTCGCTCAGCACAACCCCAGTGTAGATCAGGCTG<br>ATGAGTCACTGCAACCCCCATGGGCGACCATGGCAGT<br>GGCTGCGTTGGCGGCCTGCCCATGGAGAAATCCATGG<br>GACGCTCTAATTCTGACATGGTGTGAAGTGCCTATTGA<br>GCTAACTGGTAGTCCTCCGGCCCCTGATTGCGGCTAAT<br>CCTAACTGCGGAGCACATGCTCACAAACCAGTGGGTG<br>GTGTGTCGTAACGGGCAACTCTGCAGCGGAACCGACT<br>ACTTTGGGTGTCCGTGTTTCCTTTTATTCCTATATTGGC<br>TGCTTATGGTGACAATCAAAAAGTTGTTACCATATAGC<br>TATTGGATTGGCCATCCGGTGTGCAACAGGGCAACTG<br>TTTACCTATTTATTGGTTTTGTACCATTATCACTGAAGT<br>CTGTGATCACTCTCAAATTCATTTTGACCCTCAACACA<br>ATCAAACGCCACCATGGGATGGAGCTGTATCATCCTCT<br>TCTTGGTAGCAACAGCTACCGGTGTGCACTCCGACATC<br>GTGATGACCCAGACTCCACTCTCCCTGCCCGTCACCCC<br>TGGAGAGCCCGCCAGCATTAGCTGCAGGTCTAGCAAG<br>AGCCTCTTGCACAGCAATGGCATCACTTATTTGTATTG<br>GTACCTGCAAAAGCCAGGGCAGTCTCCACAGCTCCTG<br>ATTTATCAAATGTCCAACCTTGTCTCTGGCGTCCCTGA<br>TCGGTTCTCCGGTTCCGGGTCAGGCACTGATTTCACAC<br>TGAAAATCAGCAGGGTGGAGGCTGAGGATGTTGGAGT<br>TTATTACTGCGCTCAGAATCTAGAACTTCCTTACACCT<br>TCGGCGGAGGGACCAAGGTGGAGATCAAATCCAGCGC<br>TAGCACCAAGGGCCCCTCCGTGTTCCCCCTGGCCCCCA<br>GCAGCAAGAGCACCAGCGGCGGCACAGCCGCTCTGGG<br>CTGCCTGGTCAAGGACTACTTCCCCGAGCCCGTGACCG<br>TGTCCTGGAACAGCGGAGCCCTGACCTCCGGCGTGCA<br>CACCTTCCCCGCCGTGCTGCAGAGTTCTGGCCTGTATA<br>GCCTGAGCAGCGTGGTCACCGTGCCTTCTAGCAGCCTG<br>GGCACCCAGACCTACATCTGCAACGTGAACCACAAGC<br>CCAGCAACACCAAGGTGGACAAGAAGGTGGAGCCCA<br>AGAGCTGCGAGGGGGCGGATCCTTCTGGGTGCTGGT<br>GGTGGTGGGCGGCGTGCTGGCCTGCTACAGCCTGCTG<br>GTGACCGTGGCCTTCATCATCTTCTGGGTGAGGAGCAA<br>GAGGAGCAGGCTGCTGCACAGCGACTACATGAACATG<br>ACCCCCAGGAGGCCCGGCCCCACCAGGAAGCACTACC<br>AGCCCTACGCCCCCCCCAGGGACTTCGCCGCCTACAG<br>GAGCAGGGTGAAGTTCAGCAGGAGCGCCGACGCCCCC<br>GCCTACCAGCAGGGCCAGAACCAGCTGTATAACGAGC<br>TGAACCTGGGCAGGAGGGAGGAGTACGACGTGCTGGA<br>CAAGAGGAGGGGCAGGGACCCCGAGATGGGCGGCAA<br>GCCCAGGAGGAAGAACCCCCAGGAGGGCCTGTATAAC<br>GAGCTGCAGAAGGACAAGATGGCCGAGGCCTACAGC<br>GAGATCGGCATGAAGGGCGAGAGGAGGAGGGGCAAG<br>GGCCACGACGGCCTGTACCAGGGCCTGAGCACCGCCA<br>CCAAGGACACCTACGACGCCCTGCACATGCAGGCCCT<br>GCCCCCCAGG | |
| Anti-CD20-(GA101)-VH | see Table 3 | 25 |
| crossFab CL | GCTAGCGTGGCCGCTCCCTCCGTGTTCATCTTCCCACC<br>TTCCGACGAGCAGCTGAAGTCCGGCACCGCTTCTGTCG<br>TGTGCCTGCTGAACAACTTCTACCCCCGCGAGGCCAA<br>GGTGCAGTGGAAGGTGGACAACGCCCTGCAGTCCGGC<br>AACAGCCAGGAATCCGTGACCGAGCAGGACTCCAAGG<br>ACAGCACCTACTCCCTGTCCTCCACCCTGACCCTGTCC | 47 |

TABLE 6-continued

Anti-CD20 crossFab (VH-CL-ATD) DNA sequences

| Construct | DNA Sequenz | SEQ ID NO |
|---|---|---|
| | AAGGCCGACTACGAGAAGCACAAGGTGTACGCCTGCG<br>AAGTGACCCACCAGGGCCTGTCTAGCCCCGTGACCAA<br>GTCTTTCAACCGGGGCGAGTGCTGA | |
| Anti-CD20-(GA101)-VL | see Table 3 | 23 |
| crossFab CH1 | TCCAGCGCTAGCACCAAGGGCCCCTCCGTGTTCCCCCT<br>GGCCCCCAGCAGCAAGAGCACCAGCGGCGGCACAGCC<br>GCTCTGGGCTGCCTGGTCAAGGACTACTTCCCCGAGCC<br>CGTGACCGTGTCCTGGAACAGCGGAGCCCTGACCTCC<br>GGCGTGCACACCTTCCCCGCCGTGCTGCAGAGTTCTGG<br>CCTGTATAGCCTGAGCAGCGTGGTCACCGTGCCTTCTA<br>GCAGCCTGGGCACCCAGACCTACATCTGCAACGTGAA<br>CCACAAGCCCAGCAACACCAAGGTGGACAAGAAGGT<br>GGAGCCCAAGAGCTGC | 48 |
| IRES EV71, internal ribosomal entry site | see Table 3 | 27 |
| G4S linker | see Table 3 | 28 |
| CD28ATD-CD28CSD-CD3zSSD | see Table 3 | 32 |
| T2A linker | see Table 3 | 33 |
| eGFP | see Table 3 | 34 |
| Anti-CD20-(GA101)-crossFabVH-CL<br>CD28ATD-<br>CD28CSD-<br>CD3zSSD-<br>eGFP<br>pETR17098 | ATGGGATGGAGCTGTATCATCCTCTTCTTGGTAGCAAC<br>AGCTACCGGTGTGCATTCCCAGGTGCAATTGGTGCAGT<br>CTGGCGCTGAAGTTAAGAAGCCTGGGAGTTCAGTGAA<br>GGTCTCCTGCAAGGCTTCCGGATACGCCTTCAGCTATT<br>CTTGGATCAATTGGGTGCGGCAGGCGCCTGGACAAGG<br>GCTCGAGTGGATGGGACGGATCTTTCCCGGCGATGGG<br>GATACTGACTACAATGGGAAATTCAAGGGCAGAGTCA<br>CAATTACCGCCGACAAATCCACTAGCACAGCCTATAT<br>GGAGCTGAGCAGCCTGAGATCTGAGGACACGGCCGTG<br>TATTACTGTGCAAGAAATGTCTTTGATGGTTACTGGCT<br>TGTTTACTGGGGCCAGGGAACCCTGGTCACCGTCTCCT<br>CAGCTAGCGTGGCCGCTCCCTCCGTGTTCATCTTCCCA<br>CCTTCCGACGAGCAGCTGAAGTCCGGCACCGCTTCTGT<br>CGTGTGCCTGCTGAACAACTTCTACCCCCGCGAGGCCA<br>AGGTGCAGTGGAAGGTGGACAACGCCCTGCAGTCCGG<br>CAACAGCCAGGAATCCGTGACCGAGCAGGACTCCAAG<br>GACAGCACCTACTCCCTGTCCTCCACCCTGACCCTGTC<br>CAAGGCCGACTACGAGAAGCACAAGGTGTACGCCTGC<br>GAAGTGACCCACCAGGGCCTGTCTAGCCCCGTGACCA<br>AGTCTTTCAACCGGGGCGAGTGCTGATAAGGAATTCC<br>CCGAAGTAACTTAGAAGCTGTAAATCAACGATCAATA<br>GCAGGTGTGGCACACCAGTCATACCTTGATCAAGCAC<br>TTCTGTTTCCCCGGACTGAGTATCAATAGGCTGCTCGC<br>GCGGCTGAAGGAGAAAACGTTCGTTACCCGACCAACT<br>ACTTCGAGAAGCTTAGTACCACCATGAACGAGGCAGG<br>GTGTTTCGCTCAGCACAACCCCAGTGTAGATCAGGCTG<br>ATGAGTCACTGCAACCCCCATGGGCGACCATGGCAGT<br>GGCTGCGTTGGCGGCCTGCCCATGGAGAAATCCATGG<br>GACGCTCTAATTCTGACATGGTGTGAAGTGCCTATTGA<br>GCTAACTGGTAGTCCTCCGGCCCCTGATTGCGGCTAAT<br>CCTAACTGCGGAGCACATGCTCACAAACCAGTGGGTG<br>GTGTGTCGTAACGGGCAACTCTGCAGCGGAACCGACT<br>ACTTTGGGTGTCCGTGTTTCCTTTTATTCCTATATTGGC<br>TGCTTATGGTGACAATCAAAAAGTTGTTACCATATAGC<br>TATTGGATTGGCCATCCGGTGTGCAACAGGGCAACTG<br>TTTACCTATTTATTGGTTTTGTACCATTATCACTGAAGT<br>CTGTGATCACTCTCAAATTCATTTTGACCCTCAACACA<br>ATCAAACGCCACCATGGGATGGAGCTGTATCATCCTCT<br>TCTTGGTAGCAACAGCTACCGGTGTGCACTCCGACATC<br>GTGATGACCCAGACTCCACTCTCCCTGCCCGTCACCCC<br>TGGAGAGCCCGCCAGCATTAGCTGCAGGTCTAGCAAG<br>AGCCTCTTGCACAGCAATGGCATCACTTATTTGTATTG<br>GTACCTGCAAAAGCCAGGGCAGTCTCCACAGCTCCTG<br>ATTTATCAAATGTCCAACCTTGTCTCTGGCGTCCCTGA<br>TCGGTTCTCCGGTTCCGGGTCAGGCACTGATTTCACAC<br>TGAAAATCAGCAGGGTGGAGGCTGAGGATGTTGGAGT<br>TTATTACTGCGCTCAGAATCTAGAACTTCCTTACACCT | 49 |

TABLE 6-continued

Anti-CD20 crossFab (VH-CL-ATD) DNA sequences

| Construct | DNA Sequenz | SEQ ID NO |
|---|---|---|
| | TCGGCGGAGGGACCAAGGTGGAGATCAAATCCAGCGC<br>TAGCACCAAGGGCCCCTCCGTGTTCCCCCTGGCCCCCA<br>GCAGCAAGAGCACCAGCGGCGGCACAGCCGCTCTGGG<br>CTGCCTGGTCAAGGACTACTTCCCCGAGCCCGTGACCG<br>TGTCCTGGAACAGCGGAGCCCTGACCTCCGGCGTGCA<br>CACCTTCCCCGCCGTGCTGCAGAGTTCTGGCCTGTATA<br>GCCTGAGCAGCGTGGTCACCGTGCCTTCTAGCAGCCTG<br>GGCACCCAGACCTACATCTGCAACGTGAACCACAAGC<br>CCAGCAACACCAAGGTGGACAAGAAGGTGGAGCCCA<br>AGAGCTGCGGAGGGGCGGATCCTTCTGGGTGCTGGT<br>GGTGGTGGGCGGCGTGCTGGCCTGCTACAGCCTGCTG<br>GTGACCGTGGCCTTCATCATCTTCTGGGTGAGGAGCAA<br>GAGGAGCAGGCTGCTGCACAGCGACTACATGAACATG<br>ACCCCCAGGAGGCCCGGCCCCACCAGGAAGCACTACC<br>AGCCCTACGCCCCCCCCAGGGACTTCGCCGCCTACAG<br>GAGCAGGGTGAAGTTCAGCAGGAGCGCCGACGCCCCC<br>GCCTACCAGCAGGGCCAGAACCAGCTGTATAACGAGC<br>TGAACCTGGGCAGGAGGGAGGAGTACGACGTGCTGGA<br>CAAGAGGAGGGGCAGGGACCCCGAGATGGGCGGCAA<br>GCCCAGGAGGAAGAACCCCCAGGAGGGCCTGTATAAC<br>GAGCTGCAGAAGGACAAGATGGCCGAGGCCTACAGC<br>GAGATCGGCATGAAGGGCGAGAGGAGGAGGGGCAAG<br>GGCCACGACGGCCTGTACCAGGGCCTGAGCACCGCCA<br>CCAAGGACACCTACGACGCCCTGCACATGCAGGCCCT<br>GCCCCCCAGGTCCGGAGAGGGCAGAGGAAGTCTTCTA<br>ACATGCGGTGACGTGGAGGAGAATCCCGGCCCTAGGG<br>TGAGCAAGGGCGAGGAGCTGTTCACCGGGGTGGTGCC<br>CATCCTGGTCGAGCTGGACGGCGACGTAAACGGCCAC<br>AAGTTCAGCGTGTCCGGCGAGGGCGAGGGCGATGCCA<br>CCTACGGCAAGCTGACCCTGAAGTTCATCTGCACCACC<br>GGCAAGCTGCCCGTGCCCTGGCCCACCCTCGTGACCA<br>CCCTGACCTACGGCGTGCAGTGCTTCAGCCGCTACCCC<br>GACCACATGAAGCAGCACGACTTCTTCAAGTCCGCCA<br>TGCCCGAAGGCTACGTCCAGGAGCGCACCATCTTCTTC<br>AAGGACGACGGCAACTACAAGACCCGCGCCGAGGTG<br>AAGTTCGAGGGCGACACCCTGGTGAACCGCATCGAGC<br>TGAAGGGCATCGACTTCAAGGAGGACGGCAACATCCT<br>GGGGCACAAGCTGGAGTACAACTACAACAGCCACAAC<br>GTCTATATCATGGCCGACAAGCAGAAGAACGGCATCA<br>AGGTGAACTTCAAGATCCGCCACAACATCGAGGACGG<br>CAGCGTGCAGCTCGCCGACCACTACCAGCAGAACACC<br>CCCATCGGCGACGGCCCCGTGCTGCTGCCCGACAACC<br>ACTACCTGAGCACCCAGTCCGCCCTGAGCAAAGACCC<br>CAACGAGAAGCGCGATCACATGGTCCTGCTGGAGTTC<br>GTGACCGCCGCCGGGATCACTCTCGGCATGGACGAGC<br>TGTACAAGTGA | |

TABLE 7

Anti-CD20 Fab (VL-CL-ATD) amino acid sequences

| Construct | Protein Sequence | SEQ ID NO |
|---|---|---|
| Anti-CD20 (GA101) CDR H1 Kabat | see Table 2 | 1 |
| Anti-CD20 (GA101) CDR H2 Kabat | see Table 2 | 2 |
| Anti-CD20 (GA101) CDR H3 Kabat | see Table 2 | 3 |
| Anti-CD20 (GA101) CDR L1 Kabat | see Table 2 | 4 |
| Anti-CD20 (GA101) CDR L2 Kabat | see Table 2 | 5 |
| Anti-CD20 (GA101) CDR L3 Kabat | see Table 2 | 6 |
| Anti-CD20-(GA101)-Fab VL-CL | DIVMTQTPLSLPVTPGEPASISCRSSKSLLHSNGITYLYWY<br>LQKPGQSPQLLIYQMSNLVSGVPDRFSGSGSGTDFTLKIS | 50 |

TABLE 7-continued

Anti-CD20 Fab (VL-CL-ATD) amino acid sequences

| Construct | Protein Sequence | SEQ ID NO |
|---|---|---|
| light chain-CD28ATD-CD28CSD-CD3zSSD fusion | RVEAEDVGVYYCAQNLELPYTFGGGTKVEIKRTVAAPS VFIFPPSDEQLKSGTASVVCLLNNFYPREAKVQWKVDNA LQSGNSQESVTEQDSKDSTYSLSSTLTLSKADYEKHKVY ACEVTHQGLSSPVTKSFNRGECGGGGSFWVLVVVGGVL ACYSLLVTVAFIIFWVRSKRSRLLHSDYMNMTPRRPGPT RKHYQPYAPPRDFAAYRSRVKFSRSADAPAYQQGQNQL YNELNLGRREEYDVLDKRRGRDPEMGGKPRRKNPQEGL YNELQKDKMAEAYSEIGMKGERRRGKGHDGLYQGLST ATKDTYDALHMQALPPR | |
| Anti-CD20-(GA101)-Fab heavy chain | see Table 2 | 8 |
| Anti-CD20-(GA101)-Fab light chain | see Table 2 | 9 |
| Anti-CD20-(GA101) VH | see Table 2 | 12 |
| CL | see Table 2 | 11 |
| Anti-CD20-(GA101)-VL | see Table 2 | 10 |
| CH1 | see Table 2 | 13 |
| G4S linker | see Table 2 | 20 |
| CD28ATD-CD28CSD-CD3zSSD | see Table 2 | 17 |
| T2A linker | see Table 2 | 21 |
| eGFP | see Table 2 | 18 |

TABLE 8

Anti-CD20 scFab amino acid sequences

| Construct | Protein Sequence | SEQ ID NO |
|---|---|---|
| Anti-CD20 (GA101) CDR H1 Kabat | see Table 2 | 1 |
| Anti-CD20 (GA101) CDR H2 Kabat | see Table 2 | 2 |
| Anti-CD20 (GA101) CDR H3 Kabat | see Table 2 | 3 |
| Anti-CD20 (GA101) CDR L1 Kabat | see Table 2 | 4 |
| Anti-CD20 (GA101) CDR L2 Kabat | see Table 2 | 5 |
| Anti-CD20 (GA101) CDR L3 Kabat | see Table 2 | 6 |
| Anti-CD20-(GA101)-scFab-CD28ATD-CD28CSD-CD3zSSD fusion pETR17101 | DIVMTQTPLSLPVTPGEPASISCRSSKSLLHSNGITYLYWY LQKPGQSPQLLIYQMSNLVSGVPDRFSGSGSGTDFTLKIS RVEAEDVGVYYCAQNLELPYTFGGGTKVEIKRTVAAPS VFIFPPSDEQLKSGTASVVCLLNNFYPREAKVQWKVDNA LQSGNSQESVIEQDSKDSTYSLSSTLTLSKADYEKHKVY ACEVTHQGLSSPVTKSFNRGECGGGGSGGGGSGGGGSG GGGSGGGGSGGGGSGGGQVQLVQSGAEVKKPGSSVKVSC KASGYAFSYSWINWVRQAPGQGLEWMGRIFPGDGDTD YNGKFKGRVTITADKSTSTAYMELSSLRSEDTAVYYCAR NVFDGYWLVYWGQGTLVTVSSASTKGPSVFPLAPSSKST SGGTAALGCLVKDYFPEPVTVSWNSGALTSGVHTFPAVL QSSGLYSLSSVVTVPSSSLGTQTYICNVNHKPSNTKVDKK VEPKSCGGGGSFWVLVVVGGVLACYSLLVTVAFIIFWVR SKRSRLLHSDYMNMTPRRPGPTRKHYQPYAPPRDFAAY | 51 |

TABLE 8-continued

Anti-CD20 scFab amino acid sequences

| Construct | Protein Sequence | SEQ ID NO |
|---|---|---|
| | RSRVKFSRSADAPAYQQGQNQLYNELNLGRREEYDVLD<br>KRRGRDPEMGGKPRRKNPQEGLYNELQKDKMAEAYSEI<br>GMKGERRRGKGHDGLYQGLSTATKDTYDALHMQALPP<br>R | |
| Anti-CD20-(GA101)-<br>scFab | DIVMTQTPLSLPVTPGEPASISCRSSKSLLHSNGITYLYWY<br>LQKPGQSPQLLIYQMSNLVSGVPDRFSGSGSGTDFTLKIS<br>RVEAEDVGVYYCAQNLELPYTFGGGTKVEIKRTVAAPS<br>VFIFPPSDEQLKSGTASVVCLLNNFYPREAKVQWKVDNA<br>LQSGNSQESVIEQDSKDSTYSLSSTLTLSKADYEKHKVY<br>ACEVTHQGLSSPVTKSFNRGECGGGGSGGGGSGGGGSG<br>GGGSGGGGSGGGGSGGQVQLVQSGAEVKKPGSSVKVSC<br>KASGYAFSYSWINWVRQAPGQGLEWMGRIFPGDGDTD<br>YNGKFKGRVTITADKSTSTAYMELSSLRSEDTAVYYCAR<br>NVFDGYWLVYWGQGTLVTVSSASTKGPSVFPLAPSSKST<br>SGGTAALGCLVKDYFPEPVTVSWNSGALTSGVHTFPAVL<br>QSSGLYSLSSVVTVPSSSLGTQTYICNVNHKPSNTKVDKK<br>VEPKSC | 52 |
| Anti-CD20-(GA101)<br>VL | see Table 2 | 10 |
| scFab-CL | RTVAAPSVFIFPPSDEQLKSGTASVVCLLNNFYPREAKVQ<br>WKVDNALQSGNSQESVTEQDSKDSTYSLSSTLTLSKADY<br>EKHKVYACEVTHQGLSSPVTKSFNRGE | 53 |
| Anti-CD20-(GA101)<br>VH | see Table 2 | 12 |
| CH1 | see Table 2 | 13 |
| CD28TM-CD28-CD3z | see Table 2 | 17 |
| (G4S)$_6$G$_2$ linker | GGGGSGGGGSGGGGSGGGGSGGGGSGGGGSGG | 54 |

TABLE 9

Anti-CD20 scFab DNA sequences

| Construct | DNA Sequenz | SEQ ID NO |
|---|---|---|
| Anti-CD20-(GA101)-<br>scFab-<br>CD28ATD-<br>CD28CSD-<br>CD3zSSD fusion<br>pETR17101 | ATGGGATGGAGCTGTATCATCCTCTTCTTGGTAGCAAC<br>AGCTACGGGTGTGCATTCCGACATCGTGATGACCCAG<br>ACTCCACTCTCCCTGCCCGTCACCCCTGGAGAGCCCGC<br>CAGCATTAGCTGCAGGTCTAGCAAGAGCCTCTTGCAC<br>AGCAATGGCATCACTTATTTGTATTGGTACCTGCAAAA<br>GCCAGGGCAGTCTCCACAGCTCCTGATTTATCAAATGT<br>CCAACCTTGTCTCTGGCGTCCCTGATCGGTTCTCCGGT<br>TCCGGGTCAGGCACTGATTTCACACTGAAAATCAGCA<br>GGGTGGAGGCTGAGGATGTTGGAGTTTATTACTGCGC<br>TCAGAATCTAGAACTTCCTTACACCTTCGGCGGAGGG<br>ACCAAGGTGGAGATCAAACGTACGGTGGCTGCACCAT<br>CTGTCTTCATCTTCCCGCCATCTGATGAGCAGTTGAAA<br>TCTGGAACTGCCTCTGTTGTGTGCCTGCTGAATAACTT<br>CTATCCCAGAGAGGCCAAAGTACAGTGGAAGGTGGAT<br>AACGCCCTCCAATCGGGTAACTCCCAGGAGAGTGTCA<br>CAGAGCAGGACAGCAAGGACAGCACCTACAGCCTCAG<br>CAGCACCCTGACGCTGAGCAAAGCAGACTACGAGAAA<br>CACAAAGTCTACGCCTGCGAAGTCACCCATCAGGGCC<br>TGAGCTCGCCCGTCACAAAGAGCTTCAACAGGGGAGA<br>GTGTGGCGGCGAGGATCTGGTGGCGGAGGTAGTGGT<br>GGTGGTGGATCTGGCGGAGGCGGCTCCGGCGGAGGTG<br>GAAGCGGAGGTGGTGGTTCCGGAGGACAGGTGCAATT<br>GGTGCAGTCTGGCGCTGAAGTTAAGAAGCCTGGGAGT<br>TCAGTGAAGGTCTCCTGCAAGGCTTCGGGATACGCCTT<br>CAGCTATTCTTGGATCAATTGGGTGCGGCAGGCGCCTG<br>GACAAGGGCTCGAGTGGATGGGACGGATCTTTCCCGG<br>CGATGGGGATACTGACTACAATGGGAAATTCAAGGGC<br>AGAGTCACAATTACCGCCGACAAATCCACTAGCACAG<br>CCTATATGGAGCTGAGCAGCCTGAGATCTGAGGACAC<br>GGCCGTGTATTACTGTGCAAGAAATGTCTTTGATGGTT<br>ACTGGCTTGTTTACTGGGGCCAGGGAACCCTGGTCACC<br>GTCTCCTCAGCTAGCACCAAGGGCCCCTCCGTGTTCCC | 55 |

TABLE 9-continued

Anti-CD20 scFab DNA sequences

| Construct | DNA Sequenz | SEQ ID NO |
|---|---|---|
| | CCTGGCCCCAGCAGCAAGAGCACCAGCGGCGGCACA<br>GCCGCTCTGGGCTGCCTGGTCAAGGACTACTTCCCCGA<br>GCCCGTGACCGTGTCCTGGAACAGCGGAGCCCTGACC<br>TCCGGCGTGCACACCTTCCCCGCCGTGCTGCAGAGTTC<br>TGGCCTGTATAGCCTGAGCAGCGTGGTCACCGTGCCTT<br>CTAGCAGCCTGGGCACCCAGACCTACATCTGCAACGT<br>GAACCACAAGCCCAGCAACACCAAGGTGGACAAGAA<br>GGTGGAGCCCAAGAGCTGCGGAGGGGGCGGATCCTTC<br>TGGGTGCTGGTGGTGGTGGGCGGCGTGCTGGCCTGCT<br>ACAGCCTGCTGGTGACCGTGGCCTTCATCATCTTCTGG<br>GTGAGGAGCAAGAGGAGCAGGCTGCTGCACAGCGACT<br>ACATGAACATGACCCCCAGGAGGCCCGGCCCCACCAG<br>GAAGCACTACCAGCCCTACGCCCCCCCCAGGGACTTC<br>GCCGCCTACAGGAGCAGGGTGAAGTTCAGCAGGAGCG<br>CCGACGCCCCCGCCTACCAGCAGGGCCAGAACCAGCT<br>GTATAACGAGCTGAACCTGGGCAGGAGGGAGGAGTAC<br>GACGTGCTGGACAAGAGGAGGGGCAGGGACCCCGAG<br>ATGGGCGGCAAGCCCAGGAGGAAGAACCCCCAGGAG<br>GGCCTGTATAACGAGCTGCAGAAGGACAAGATGGCCG<br>AGGCCTACAGCGAGATCGGCATGAAGGGCGAGAGGA<br>GGAGGGGCAAGGGCCACGACGGCCTGTACCAGGGCCT<br>GAGCACCGCCACCAAGGACACCTACGACGCCCTGCAC<br>ATGCAGGCCCTGCCCCCCAGG | |
| scFab-VL | GACATCGTGATGACCCAGACTCCACTCTCCCTGCCCGT<br>CACCCCTGGAGAGCCCGCCAGCATTAGCTGCAGGTCT<br>AGCAAGAGCCTCTTGCACAGCAATGGCATCACTTATTT<br>GTATTGGTACCTGCAAAAGCCAGGGCAGTCTCCACAG<br>CTCCTGATTTATCAAATGTCCAACCTTGTCTCTGGCGT<br>CCCTGATCGGTTCTCCGGTTCCGGGTCAGGCACTGATT<br>TCACACTGAAAATCAGCAGGGTGGAGGCTGAGGATGT<br>TGGAGTTTATTACTGCGCTCAGAATCTAGAACTTCCTT<br>ACACCTTCGGCGGAGGGACCAAGGTGGAGATCAAA | 56 |
| scFab-CL | CGTACGGTGGCTGCACCATCTGTCTTCATCTTCCCGCC<br>ATCTGATGAGCAGTTGAAATCTGGAACTGCCTCTGTTG<br>TGTGCCTGCTGAATAACTTCTATCCCAGAGAGGCCAA<br>AGTACAGTGGAAGGTGGATAACGCCCTCCAATCGGGT<br>AACTCCCAGGAGAGTGTCACAGAGCAGGACAGCAAG<br>GACAGCACCTACAGCCTCAGCAGCACCCTGACGCTGA<br>GCAAAGCAGACTACGAGAAACACAAAGTCTACGCCTG<br>CGAAGTCACCCATCAGGGCCTGAGCTCGCCCGTCACA<br>AAGAGCTTCAACAGGGGAGAGTGT | 57 |
| Anti-CD20-(GA101)-<br>scFab-VH | CAGGTGCAATTGGTGCAGTCTGGCGCTGAAGTTAAGA<br>AGCCTGGGGAGTTCAGTGAAGGTCTCCTGCAAGGCTTC<br>TGGGATACGCCTTCAGCTATTCTTGGATCAATTGGGTGC<br>GGCAGGCGCCTGGACAAGGGCTCGAGTGGATGGGACG<br>GATCTTTCCCGGCGATGGGGATACTGACTACAATGGG<br>AAATTCAAGGGCAGAGTCACAATTACCGCCGACAAAT<br>CCACTAGCACAGCCTATATGGAGCTGAGCAGCCTGAG<br>ATCTGAGGACACGGCCGTGTATTACTGTGCAAGAAAT<br>GTCTTTGATGGTTACTGGCTTGTTTACTGGGGCCAGGG<br>AACCCTGGTCACCGTCTCCTCA | 58 |
| Fab-CH1 | see Table 3 | 26 |
| CD28ATD-CD28CSD-<br>CD3zSSD | see Table 2 | 32 |
| Anti-CD20-(GA101)-<br>scFab-<br>CD28ATD-<br>CD28CSD-<br>CD3zSSD-<br>eGFP fusion<br>pETR17101 | ATGGAGCTGTATCATCCTCTTCTTGGTAGCAACAGCTA<br>CGGGTGTGCATTCCGACATCGTGATGACCCAGACTCC<br>ACTCTCCCTGCCCGTCACCCCTGGAGAGCCCGCCAGCA<br>TTAGCTGCAGGTCTAGCAAGAGCCTCTTGCACAGCAA<br>TGGCATCACTTATTTGTATTGGTACCTGCAAAAGCCAG<br>GGCAGTCTCCACAGCTCCTGATTTATCAAATGTCCAAC<br>CTTGTCTCTGGCGTCCCTGATCGGTTCTCCGGTTCCGG<br>GTCAGGCACTGATTTCACACTGAAAATCAGCAGGGTG<br>GAGGCTGAGGATGTTGGAGTTTATTACTGCGCTCAGA<br>ATCTAGAACTTCCTTACACCTTCGGCGGAGGGACCAA<br>GGTGGAGATCAAACGTACGGTGGCTGCACCATCTGTC<br>TTCATCTTCCCGCCATCTGATGAGCAGTTGAAATCTGG<br>AACTGCCTCTGTTGTGTGCCTGCTGAATAACTTCTATC<br>CCAGAGAGGCCAAAGTACAGTGGAAGGTGGATAACG<br>CCCTCCAATCGGGTAACTCCCAGGAGAGTGTCACAGA<br>GCAGGACAGCAAGGACAGCACCTACAGCCTCAGCAGC | 59 |

TABLE 9-continued

Anti-CD20 scFab DNA sequences

| Construct | DNA Sequenz | SEQ ID NO |
|---|---|---|
| | ACCCTGACGCTGAGCAAAGCAGACTACGAGAAACACA<br>AAGTCTACGCCTGCGAAGTCACCCATCAGGGCCTGAG<br>CTCGCCCGTCACAAAGAGCTTCAACAGGGGAGAGTGT<br>GGCGGCGGAGGATCTGGTGGCGGAGGTAGTGGTGGTG<br>GTGGATCTGGCGGAGGCGGCTCCGGCGGAGGTGGAAG<br>CGGAGGTGGTGGTTCCGGAGGACAGGTGCAATTGGTG<br>CAGTCTGGCGCTGAAGTTAAGAAGCCTGGGAGTTCAG<br>TGAAGGTCTCCTGCAAGGCTTCGGGATACGCCTTCAGC<br>TATTCTTGGATCAATTGGGTGCGGCAGGCGCCTGGAC<br>AAGGGCTCGAGTGGATGGGACGGATCTTTCCCGGCGA<br>TGGGGATACTGACTACAATGGGAAATTCAAGGGCAGA<br>GTCACAATTACCGCCGACAAATCCACTAGCACAGCCT<br>ATATGGAGCTGAGCAGCCTGAGATCTGAGGACACGGC<br>CGTGTATTACTGTGCAAGAAATGTCTTTGATGGTTACT<br>GGCTTGTTTACTGGGGCCAGGGAACCCTGGTCACCGTC<br>TCCTCAGCTAGCACCAAGGGCCCCTCCGTGTTCCCCCT<br>GGCCCCCAGCAGCAAGAGCACCAGCGGCGGCACAGCC<br>GCTCTGGGCTGCCTGGTCAAGGACTACTTCCCCGAGCC<br>CGTGACCGTGTCCTGGAACAGCGGAGCCCTGACCTCC<br>GGCGTGCACACCTTCCCCGCCGTGCTGCAGAGTTCTGG<br>CCTGTATAGCCTGAGCAGCGTGGTCACCGTGCCTTCTA<br>GCAGCCTGGGCACCCAGACCTACATCTGCAACGTGAA<br>CCACAAGCCCAGCAACACCAAGGTGGACAAGAAGGT<br>GGAGCCCAAGAGCTGCGGAGGGGGCGGATCCTTCTGG<br>GTGCTGGTGGTGGTGGGCGGCGTGCTGGCCTGCTACA<br>GCCTGCTGGTGACCGTGGCCTTCATCATCTTCTGGGTG<br>AGGAGCAAGAGGAGCAGGCTGCTGCACAGCGACTAC<br>ATGAACATGACCCCCAGGAGGCCCGGCCCCACCAGGA<br>AGCACTACCAGCCCTACGCCCCCCCCAGGGACTTCGC<br>CGCCTACAGGAGCAGGGTGAAGTTCAGCAGGAGCGCC<br>GACGCCCCCGCCTACCAGCAGGGCCAGAACCAGCTGT<br>ATAACGAGCTGAACCTGGGCAGGAGGGAGGAGTACG<br>ACGTGCTGGACAAGAGGAGGGGCAGGGACCCCGAGA<br>TGGGCGGCAAGCCCAGGAGGAAGAACCCCCAGGAGG<br>GCCTGTATAACGAGCTGCAGAAGGACAAGATGGCCGA<br>GGCCTACAGCGAGATCGGCATGAAGGGCGAGAGGAG<br>GAGGGGCAAGGGCCACGACGGCCTGTACCAGGGCCTG<br>AGCACCGCCACCAAGGACACCTACGACGCCCTGCACA<br>TGCAGGCCCTGCCCCCCAGGTCCGGAGAGGGCAGAGG<br>AAGTCTTCTAACATGCGGTGACGTGGAGGAGAATCCC<br>GGCCCTAGGGTGAGCAAGGGCGAGGAGCTGTTCACCG<br>GGGTGGTGCCCATCCTGGTCGAGCTGGACGGCGACGT<br>AAACGGCCACAAGTTCAGCGTGTCCGGCGAGGGCGAG<br>GGCGATGCCACCTACGGCAAGCTGACCCTGAAGTTCA<br>TCTGCACCACCGGCAAGCTGCCCGTGCCCTGGCCCACC<br>CTCGTGACCACCCTGACCTACGGCGTGCAGTGCTTCAG<br>CCGCTACCCCGACCACATGAAGCAGCACGACTTCTTC<br>AAGTCCGCCATGCCCGAAGGCTACGTCCAGGAGCGCA<br>CCATCTTCTTCAAGGACGACGGCAACTACAAGACCCG<br>CGCCGAGGTGAAGTTCGAGGGCGACACCCTGGTGAAC<br>CGCATCGAGCTGAAGGGCATCGACTTCAAGGAGGACG<br>GCAACATCCTGGGGCACAAGCTGGAGTACAACTACAA<br>CAGCCACAACGTCTATATCATGGCCGACAAGCAGAAG<br>AACGGCATCAAGGTGAACTTCAAGATCCGCCACAACA<br>TCGAGGACGGCAGCGTGCAGCTCGCCGACCACTACCA<br>GCAGAACACCCCCATCGGCGACGGCCCCGTGCTGCTG<br>CCCGACAACCACTACCTGAGCACCCAGTCCGCCCTGA<br>GCAAAGACCCCAACGAGAAGCGCGATCACATGGTCCT<br>GCTGGAGTTCGTGACCGCCGCCGGGATCACTCTCGGC<br>ATGGACGAGCTGTACAAGTGA | |

TABLE 10

Anti-CD20-ds-scFv amino acid sequences

| Construct | Protein Sequence | SEQ ID NO |
|---|---|---|
| Anti-CD20 (GA101)<br>CDR H1 Kabat | see Table 2 | 1 |
| Anti-CD20 (GA101)<br>CDR H2 Kabat | see Table 2 | 2 |

TABLE 10-continued

Anti-CD20-ds-scFv amino acid sequences

| Construct | Protein Sequence | SEQ ID NO |
|---|---|---|
| Anti-CD20 (GA101) CDR H3 Kabat | see Table 2 | 3 |
| Anti-CD20 (GA101) CDR L1 Kabat | see Table 2 | 4 |
| Anti-CD20 (GA101) CDR L2 Kabat | see Table 2 | 5 |
| Anti-CD20 (GA101) CDR L3 Kabat | see Table 2 | 6 |
| Anti-CD20-(GA101)-ds-scFv-CD28ATD-CD28CSD-CD3zSSD fusion pETR17162 | QVQLVQSGAEVKKPGSSVKVSCKASGYAFSYSWINWVR QAPGQCLEWMGRIFPGDGDTDYNGKFKGRVTITADKST STAYMELSSLRSEDTAVYYCARNVFDGYWLVYWGQGT LVTVSSGGGGSGGGGSGGGGSGGGGSDIVMTQTPLSLPV TPGEPASISCRSSKSLLHSNGITYLYWYLQKPGQSPQLLIY QMSNLVSGVPDRFSGSGSGTDFTLKISRVEAEDVGVYYC AQNLELPYTFGCGTKVEIKGGGGSFWVLVVVGGVLACY SLLVTVAFIIFWVRSKRSRLLHSDYMNMTPRRPGPTRKH YQPYAPPRDFAAYRSRVKFSRSADAPAYQQGQNQLYNE LNLGRREEYDVLDKRRGRDPEMGGKPRRKNPQEGLYNE LQKDKMAEAYSEIGMKGERRRGKGHDGLYQGLSTATK DTYDALHMQALPPR | 60 |
| Anti-CD20-(GA101)-ds-scFv | QVQLVQSGAEVKKPGSSVKVSCKASGYAFSYSWINWVR QAPGQCLEWMGRIFPGDGDTDYNGKFKGRVTITADKST STAYMELSSLRSEDTAVYYCARNVFDGYWLVYWGQGT LVTVSSGGGGSGGGGSGGGGSGGGGSDIVMTQTPLSLPV TPGEPASISCRSSKSLLHSNGITYLYWYLQKPGQSPQLLIY QMSNLVSGVPDRFSGSGSGTDFTLKISRVEAEDVGVYYC AQNLELPYTFGCGTKVEIK | 61 |
| Anti-CD20-(GA101)-ds-VH | QVQLVQSGAEVKKPGSSVKVSCKASGYAFSYSWINWVR QAPGQCLEWMGRIFPGDGDTDYNGKFKGRVTITADKST STAYMELSSLRSEDTAVYYCARNVFDGYWLVYWGQGT LVTVSS | 62 |
| Anti-CD20-(GA101)-ds-VL | DIVMTQTPLSLPVTPGEPASISCRSSKSLLHSNGITYLYWY LQKPGQSPQLLIYQMSNLVSGVPDRFSGSGSGTDFTLKIS RVEAEDVGVYYCAQNLELPYTFGCGTKVEIK | 63 |
| CD28ATD-CD28CSD-CD3zSSD | see Table 2 | 17 |

TABLE 11

Anti-CD20 ds scFv DNA sequences

| Construct | DNA Sequenz | SEQ ID NO |
|---|---|---|
| Anti-CD20-(GA101)-ds-Fab-CD28ATD-CD28CSD-CD3zSSD fusion pETR17162 | ATGGGATGGAGCTGTATCATCCTCTTCTTGGTAGCAAC AGCTACCGGTGTGCATTCCCAGGTGCAATTGGTGCAGT CTGGCGCTGAAGTTAAGAAGCCTGGGAGTTCAGTGAA GGTCTCCTGCAAGGCTTCCGGTTACGCCTTCAGCTATT CTTGGATCAATTGGGTGCGGCAGGCGCCTGGACAATG TCTCGAGTGGATGGGACGGATCTTTCCCGGCGATGGG GATACTGACTACAATGGGAAATTCAAGGGCAGAGTCA CAATTACCGCCGACAAATCCACTAGCACAGCCTATAT GGAGCTGAGCAGCCTGAGATCTGAGGACACGGCCGTG TATTACTGTGCAAGAAATGTCTTTGATGGTTACTGGCT TGTTTACTGGGGCCAGGGAACCCTGGTCACCGTCTCCT CAGGAGGGGGCGGAAGTGGTGGCGGGGGAAGCGGCG GGGGTGGCAGCGGAGGGGGCGGATCTGACATCGTGAT GACCCAGACTCCACTCTCCCTGCCCGTCACCCCTGGAG AGCCCGCCAGCATTAGCTGCAGGTCTAGCAAGAGCCT CTTGCACAGCAATGGCATCACTTATTTGTATTGGTACC TGCAAAAGCCAGGGCAGTCTCCACAGCTCCTGATTTAT CAAATGTCCAACCTTGTCTCTGGCGTCCCTGACCGCTT CTCCGGTTCCGGGTCAGGCACTGATTTCACACTGAAAA TCAGCAGGGTGGAGGCTGAGGATGTTGGAGTTTATTA CTGCGCTCAGAATCTAGAACTTCCTTACACCTTCGGCT GTGGGACCAAGGTGGAGATCAAGGAGGGGGCGGATC | 64 |

TABLE 11-continued

Anti-CD20 ds scFv DNA sequences

| Construct | DNA Sequenz | SEQ ID NO |
|---|---|---|
| | CTTCTGGGTGCTGGTGGTGGTGGGCGGCGTGCTGGCCT<br>GCTACAGCCTGCTGGTGACCGTGGCCTTCATCATCTTC<br>TGGGTGAGGAGCAAGAGGAGCAGGCTGCTGCACAGC<br>GACTACATGAACATGACCCCCAGGAGGCCCGGCCCCA<br>CCAGGAAGCACTACCAGCCCTACGCCCCCCCCAGGGA<br>CTTCGCCGCCTACAGGAGCAGGGTGAAGTTCAGCAGG<br>AGCGCCGACGCCCCCGCCTACCAGCAGGGCCAGAACC<br>AGCTGTATAACGAGCTGAACCTGGGCAGGAGGGAGGA<br>GTACGACGTGCTGGACAAGAGGAGGGGCAGGGACCC<br>CGAGATGGGCGGCAAGCCCAGGAGGAAGAACCCCCA<br>GGAGGGCCTGTATAACGAGCTGCAGAAGGACAAGATG<br>GCCGAGGCCTACAGCGAGATCGGCATGAAGGGCGAG<br>AGGAGGAGGGGCAAGGGCCACGACGGCCTGTACCAG<br>GGCCTGAGCACCGCCACCAAGGACACCTACGACGCCC<br>TGCACATGCAGGCCCTGCCCCCCAGG | |
| Anti-CD20-(GA101)-<br>ds-VH | CAGGTGCAATTGGTGCAGTCTGGCGCTGAAGTTAAGA<br>AGCCTGGGAGTTCAGTGAAGGTCTCCTGCAAGGCTTC<br>CGGTTACGCCTTCAGCTATTCTTGGATCAATTGGGTGC<br>GGCAGGCGCCTGGACAATGTCTCGAGTGGATGGGACG<br>GATCTTTCCCGGCGATGGGGATACTGACTACAATGGG<br>AAATTCAAGGGCAGAGTCACAATTACCGCCGACAAAT<br>CCACTAGCACAGCCTATATGGAGCTGAGCAGCCTGAG<br>ATCTGAGGACACGGCCGTGTATTACTGTGCAAGAAAT<br>GTCTTTGATGGTTACTGGCTTGTTTACTGGGGCCAGGG<br>AACCCTGGTCACCGTCTCCTCA | 65 |
| Anti-CD20-(GA101)-<br>ds-VL | GACATCGTGATGACCCAGACTCCACTCTCCCTGCCCGT<br>CACCCCTGGAGAGCCCGCCAGCATTAGCTGCAGGTCT<br>AGCAAGAGCCTCTTGCACAGCAATGGCATCACTTATTT<br>GTATTGGTACCTGCAAAAGCCAGGGCAGTCTCCACAG<br>CTCCTGATTTATCAAATGTCCAACCTTGTCTCTGGCGT<br>CCCTGACCGCTTCTCCGGTTCCGGGTCAGGCACTGATT<br>TCACACTGAAAATCAGCAGGGTGGAGGCTGAGGATGT<br>TGGAGTTTATTACTGCGCTCAGAATCTAGAACTTCCTT<br>ACACCTTCGGCTGTGGGACCAAGGTGGAGATCAAA | 66 |
| CD28TM-CD28-CD3z | see Table 3 | 32 |
| Anti-CD20-(GA101)-<br>ds-scFv-<br>CD28ATD-<br>CD28CSD-<br>CD3zSSD-<br>eGFP fusion<br>pETR17162 | GCCACCATGGGATGGAGCTGTATCATCCTCTTCTTGGT<br>AGCAACAGCTACCGGTGTGCATTCCCAGGTGCAATTG<br>GTGCAGTCTGGCGCTGAAGTTAAGAAGCCTGGAGTT<br>CAGTGAAGGTCTCCTGCAAGGCTTCCGGTTACGCCTTC<br>AGCTATTCTTGGATCAATTGGGTGCGGCAGGCGCCTG<br>GACAATGTCTCGAGTGGATGGGACGGATCTTTCCCGG<br>CGATGGGGATACTGACTACAATGGGAAATTCAAGGGC<br>AGAGTCACAATTACCGCCGACAAATCCACTAGCACAG<br>CCTATATGGAGCTGAGCAGCCTGAGATCTGAGGACAC<br>GGCCGTGTATTACTGTGCAAGAAATGTCTTTGATGGTT<br>ACTGGCTTGTTTACTGGGGCCAGGGAACCCTGGTCACC<br>GTCTCCTCAGGAGGGGCGGAAGTGGTGGCGGGGGAA<br>GCGGCGGGGGTGGCAGCGGAGGGGGCGGATCTGACA<br>TCGTGATGACCCAGACTCCACTCTCCCTGCCCGTCACC<br>CCTGGAGAGCCCGCCAGCATTAGCTGCAGGTCTAGCA<br>AGAGCCTCTTGCACAGCAATGGCATCACTTATTTGTAT<br>TGGTACCTGCAAAAGCCAGGGCAGTCTCCACAGCTCC<br>TGATTTATCAAATGTCCAACCTTGTCTCTGGCGTCCCT<br>GACCGCTTCTCCGGTTCCGGGTCAGGCACTGATTTCAC<br>ACTGAAAATCAGCAGGGTGGAGGCTGAGGATGTTGGA<br>GTTTATTACTGCGCTCAGAATCTAGAACTTCCTTACAC<br>CTTCGGCTGTGGGACCAAGGTGGAGATCAAAGGAGGG<br>GGCGGATCCTTCTGGGTGCTGGTGGTGGTGGGCGGCG<br>TGCTGGCCTGCTACAGCCTGCTGGTGACCGTGGCCTTC<br>ATCATCTTCTGGGTGAGGAGCAAGAGGAGCAGGCTGC<br>TGCACAGCGACTACATGAACATGACCCCCAGGAGGCC<br>CGGCCCCACCAGGAAGCACTACCAGCCCTACGCCCCC<br>CCCAGGGACTTCGCCGCCTACAGGAGCAGGGTGAAGT<br>TCAGCAGGAGCGCCGACGCCCCCGCCTACCAGCAGGG<br>CCAGAACCAGCTGTATAACGAGCTGAACCTGGGCAGG<br>AGGGAGGAGTACGACGTGCTGGACAAGAGGAGGGGC<br>AGGGACCCCGAGATGGGCGGCAAGCCCAGGAGGAAG<br>AACCCCCAGGAGGGCCTGTATAACGAGCTGCAGAAGG<br>ACAAGATGGCCGAGGCCTACAGCGAGATCGGCATGAA<br>GGGCGAGAGGAGGAGGGGCAAGGGCCACGACGGCCT<br>GTACCAGGGCCTGAGCACCGCCACCAAGGACACCTAC<br>GACGCCCTGCACATGCAGGCCCTGCCCCCCAGGTCCG | 67 |

TABLE 11-continued

Anti-CD20 ds scFv DNA sequences

| Construct | DNA Sequenz | SEQ ID NO |
|---|---|---|
| | GAGAGGGCAGAGGAAGTCTTCTAACATGCGGTGACGT<br>GGAGGAGAATCCCGGCCCTAGGGTGAGCAAGGGCGA<br>GGAGCTGTTCACCGGGGTGGTGCCCATCCTGGTCGAG<br>CTGGACGGCGACGTAAACGGCCACAAGTTCAGCGTGT<br>CCGGCGAGGGCGAGGGCGATGCCACCTACGGCAAGCT<br>GACCCTGAAGTTCATCTGCACCACCGGCAAGCTGCCC<br>GTGCCCTGGCCCACCCTCGTGACCACCCTGACCTACGG<br>CGTGCAGTGCTTCAGCCGCTACCCCGACCACATGAAG<br>CAGCACGACTTCTTCAAGTCCGCCATGCCCGAAGGCT<br>ACGTCCAGGAGCGCACCATCTTCTTCAAGGACGACGG<br>CAACTACAAGACCCGCGCCGAGGTGAAGTTCGAGGGC<br>GACACCCTGGTGAACCGCATCGAGCTGAAGGGCATCG<br>ACTTCAAGGAGGACGGCAACATCCTGGGGCACAAGCT<br>GGAGTACAACTACAACAGCCACAACGTCTATATCATG<br>GCCGACAAGCAGAAGAACGGCATCAAGGTGAACTTCA<br>AGATCCGCCACAACATCGAGGACGGCAGCGTGCAGCT<br>CGCCGACCACTACCAGCAGAACACCCCCATCGGCGAC<br>GGCCCCGTGCTGCTGCCCGACAACCACTACCTGAGCA<br>CCCAGTCCGCCCTGAGCAAAGACCCCAACGAGAAGCG<br>CGATCACATGGTCCTGCTGGAGTTCGTGACCGCCGCCG<br>GGATCACTCTCGGCATGGACGAGCTGTACAAGTGA | |

TABLE 12

| Construct | Amino acid sequence | SEQIDNO |
|---|---|---|
| Human CD3z | MKWKALFTAAILQAQLPITEAQSFGLLDPKLCYLLDGILF<br>IYGVILTALFLRVKFSRSADAPAYQQGQNQLYNELNLGR<br>REEYDVLDKRRGRDPEMGGKPQRRKNPQEGLYNELQK<br>DKMAEAYSEIGMKGERRRGKGHDGLYQGLSTATKDTY<br>DALHMQALPPR | 68 |
| Human CD3z | ATGAAGTGGAAGGCGCTTTTCACCGCGGCCATCCTGC<br>AGGCACAGTTGCCGATTACAGAGGCACAGAGCTTTGG<br>CCTGCTGGATCCCAAACTCTGCTACCTGCTGGATGGAA<br>TCCTCTTCATCTATGGTGTCATTCTCACTGCCTTGTTCC<br>TGAGAGTGAAGTTCAGCAGGAGCGCAGAGCCCCCCGC<br>GTACCAGCAGGGCCAGAACCAGCTCTATAACGAGCTC<br>AATCTAGGACGAAGAGAGGAGTACGATGTTTTGGACA<br>AGAGACGTGGCCGGGACCCTGAGATGGGGGGAAAGC<br>CGAGAAGGAAGAACCCTCAGGAAGGCCTGTACAATGA<br>ACTGCAGAAAGATAAGATGGCGGAGGCCTACAGTGAG<br>ATTGGGATGAAAGGCGAGCGCCGGAGGGGCAAGGGG<br>CACGATGGCCTTTACCAGGGTCTCAGTACAGCCACCA<br>AGGACACCTACGACGCCCTTCACATGCAGGCCCTGCC<br>CCCTCGCTAA | 69 |
| Murine CD3z | MKWKVSVLACILHVRFPGAEAQSFGLLDPKLCYLLDGIL<br>FIYGVIITALYLRAKFSRSAETAANLQDPNQLYNELNLGR<br>REEYDVLEKKRARDPEMGGKQQRRRNPQEGVYNALQK<br>DKMAEAYSEIGTKGERRRGKGHDGLYQGLSTATKDTYD<br>ALHMQTLAPR | 70 |
| Murine CD3z | ATGAAGTGGAAAGTGTCTGTTCTCGCCTGCATCCTCCA<br>CGTGCGGTTCCCAGGAGCAGAGGCACAGAGCTTTGGT<br>CTGCTGGATCCCAAACTCTGCTACTTGCTAGATGGAAT<br>CCTCTTCATCTACGGAGTCATCATCACAGCCCTGTACC<br>TGAGAGCAAAATTCAGCAGGAGTGCAGAGACTGCTGC<br>CAACCTGCAGGACCCCAACCAGCTCTACAATGAGCTC<br>AATCTAGGGCGAAGAGAGGAATATGACGTCTTGGAGA<br>AGAAGCGGGCTCGGGATCCAGAGATGGGAGGCAAAC<br>AGCAGAGGAGGAGGAACCCCCAGGAAGGCGTATACA<br>ATGCACTGCAGAAAGACAAGATGGCAGAAGCCTACAG<br>TGAGATCGGCACAAAAGGCGAGAGGCGGAGAGGCAA<br>GGGGCACGATGGCCTTTACCAGGGTCTCAGCACTGCC<br>ACCAAGGACACCTATGATGCCCTGCATATGCAGACCC<br>TGGCCCCTCGCTAA | 71 |
| Human CD28 | ATGCTGCGCCTGCTGCTGGCGCTGAACCTGTTTCCGAG<br>CATTCAGGTGACCGGCAACAAAATTCTGGTGAAACAG<br>AGCCCGATGCTGGTGGCGTATGATAACGCGGTGAACC<br>TGAGCTGCAAATATAGCTATAACCTGTTTAGCCGCGA<br>ATTTCGCGCGAGCCTGCATAAAGGCCTGGATAGCGCG | 72 |

TABLE 12-continued

| Construct | Amino acid sequence | SEQIDNO |
|---|---|---|
| | GTGGAAGTGTGCGTGGTGTATGGCAACTATAGCCAGC<br>AGCTGCAGGTGTATAGCAAAACCGGCTTTAACTGCGA<br>TGGCAAACTGGGCAACGAAAGCGTGACCTTTTATCTG<br>CAGAACCTGTATGTGAACCAGACCGATATTTATTTTTG<br>CAAAATTGAAGTGATGTATCCGCCGCCGTATCTGGAT<br>AACGAAAAAAGCAACGGCACCATTATTCATGTGAAAG<br>GCAAACATCTGTGCCCGAGCCCGCTGTTTCCGGGCCCG<br>AGCAAACCGTTTTGGGTGCTGGTGGTGGTGGGCGGCG<br>TGCTGGCGTGCTATAGCCTGCTGGTGACCGTGGCGTTT<br>ATTATTTTTTGGGTGCGCAGCAAACGCAGCCGCCTGCT<br>GCATAGCGATTATATGAACATGACCCCGCGCCGCCCG<br>GGCCCGACCCGCAAACATTATCAGCCGTATGCGCCGC<br>CGCGCGATTTTGCGGCGTATCGCAGC | |
| Human CD28 | MLRLLLALNLFPSIQVTGNKILVKQSPMLVAYDNAVNLS<br>CKYSYNLFSREFRASLHKGLDSAVEVCVVYGNYSQQLQ<br>VYSKTGFNCDGKLGNESVTFYLQNLYVNQTDIYFCKIEV<br>MYPPPYLDNEKSNGTI1HVKGKHLCPSPLFPGPSKPFWVL<br>VVVGGVLACYSLLVTVAFIIFWVRSKRSLLHSDYMNM<br>TPRRPGPTRKHYQPYAPPRDFAAYRS | 73 |
| Murine CD28 | ATGACCCTGCGCCTGCTGTTTCTGGCGCTGAACTTTTT<br>TAGCGTGCAGGTGACCGAAAACAAAATTCTGGTGAAA<br>CAGAGCCCGCTGCTGGTGGTGGATAGCAACGAAGTGA<br>GCCTGAGCTGCCGCTATAGCTATAACCTGCTGGCGAA<br>AGAATTTCGCGCGAGCCTGTATAAAGGCGTGAACAGC<br>GATGTGGAAGTGTGCGTGGGCAACGGCAACTTTACCT<br>ATCAGCCGCAGTTTCGCAGCAACGCGGAATTTAACTG<br>CGATGGCGATTTTGATAACGAAACCGTGACCTTTCGCC<br>TGTGGAACCTGCATGTGAACCATACCGATATTTATTTT<br>TGCAAAATTGAATTTATGTATCCGCCGCCGTATCTGGA<br>TAACGAACGCAGCAACGGCACCATTATTCATATTAAA<br>GAAAAACATCTGTGCCATACCCAGAGCAGCCCGAAAC<br>TGTTTTGGGCGCTGGTGGTGGTGGCGGGCGTGCTGTTT<br>TGCTATGGCCTGCTGGTGACCGTGGCGCTGTGCGTGAT<br>TTGGACCAACAGCCGCCGCAACCGCCTGCTGCAGAGC<br>GATTATATGAACATGACCCCGCGCCGCCCGGGCCTGA<br>CCCGCAAACCGTATCAGCCGTATGCGCCGGCGCGCGA<br>TTTTGCGGCGTATCGCCCG | 74 |
| Murine CD28 | MTLRLLFLALNFFSVQVTENKILVKQSPLLVVDSNEVSLS<br>CRYSYNLLAKEFRASLYKGVNSDVEVCVGNGNFTYQPQ<br>FRSNAEFNCDGDFDNETVTFRLWNLHVNHTDIYFCKIEF<br>MYPPPYLDNERSNGTIIHIKEKHLCHTQSSPKLFWALVVV<br>AGVLFCYGLLVTVALCVIWTNSRRNRLLQSDYMNMTPR<br>RPGLTRKPYQPYAPARDFAAYRP | 75 |
| CD28 YMNM | YMNM | 76 |
| CD28 PYAP | PYAP | 77 |
| Signal peptide | ATMGWSCIILFLVATATGVHS | 78 |
| Signal peptide DNA sequence | ATGGGATGGAGCTGTATCATCCTCTTCTTGGTAGCAAC<br>AGCTACCGGTGTGCACTCC | 79 |
| Anti-WT1 (33F05) VH | QVQLQESGPGLVKPSETLSLTCTVSGGSINSYYWSWIRQP<br>PGKGLEWIGYIYYSGSTNYNPSLKSRVTISVDTSKNQFSL<br>KLSSVTAADTAVYYCARSYYEAFDYWGQGTLVTSS | 80 |
| Anti-WT1 (33F05) VL | SSELTQDPAVSVALGQTVRITCQGDSLRSYYASWYQQKP<br>GQAPVLVIYGKNNRPSGIPDRFSGSSSGNTASLTITGAQA<br>EDEADYYCNSPDMNGNAVFGGGTKLTVL | 81 |
| Anti-WT1 (11D06) VH | QVQLVQSGAEVKKPGSSVKVSCKASGGTFSSYAISWVR<br>QAPGQGLEWMGGIIPIFGTANYAQKFQGRVTITADKSTS<br>TAYMELSSLRSEDTAVYYCARSIELWWGGFDYWGQTT<br>VTVSS | 82 |
| Anti-WT1 (11D06) VL | DIQMTQSPSTLSASVGDRVTITCRASQSISSWLAWYQQKP<br>GKAPKLLIYDASSLESGVPSRFSGSGSGTEFTLTIGSLQPD<br>DFATYYCQQYEDTTFGQGTKVEIK | 83 |
| Anti-WT1 (33H09) VH | QVQLVQSGAEVKKPGSSVKVSCKASGGTFSSYAISWVR<br>QAPGQGLEWMGGIIPIFGTANYAQKFQGRVTITADKSTS<br>TAYMELSSLRSEDTAVYYCARGSYDLFSLDYWGQTTV<br>TVSS | 84 |

TABLE 12-continued

| Construct | Amino acid sequence | SEQIDNO |
|---|---|---|
| Anti-WT1 (33H09) VL | DIQMTQSPSTLSASVGDRVTITCRASQSISSWLAWYQQKP GKAPKLLIYDASSLESGVPSRFSGSGSGTEFTLTISSLQPD DFATYYCQQYYDGITFGQGTKVEIK | 85 |
| Anti-WT1 (5E11) VH | QVQLVQSGAEVKKPGSSVKVSCKASGGTFSSYAISWVR QAPGQGLEWMGGIIPIFGTANYAQKFQGRVTITADKSTS TAYMELSSLRSEDTAVYYCARSSYDLYSFDYWGQGTTV TVSS | 86 |
| Anti-WT1 (5E11) VL | DIQMTQSPSTLSASVGDRVTITCRASQSISSWLAWYQQKP GKAPKLLIYDASSLESGVPSRFSGSGSGTEFTLTISSLQPD DFATYYCQQYSFPPMITFGQGTKVEIK | 87 |
| Anti-CD3 HCDR1 Kabat | TYAMN | 88 |
| Anti-CD3 HCDR2 Kabat | RIRSKYNNYATYYADSVKG | 89 |
| Anti-CD3 HCDR3 Kabat | HGNFGNSYVSWFAY | 90 |
| Anti-CD3 LCDR1 Kabat | GSSTGAVTTSNYAN | 91 |
| Anti-CD3 LCDR2 Kabat | GTNKRAP | 92 |
| Anti-CD3 LCDR3 Kabat | ALWYSNLWV | 93 |

The invention claimed is:

1. A method for assessing the specificity of an antigen binding moiety comprising the steps of:
   a. providing an antigen binding moiety specific for a target antigen, wherein said antigen binding moiety is a Fab fragment;
   b. generating a chimeric antigen receptor (CAR) expressing reporter T (CAR-T) cell by:
      i. transferring the antigen binding moiety into a CAR vector system operationally coupled to a response element;
      ii. transferring the CAR vector system into a reporter T cell comprising a reporter gene under the control of the response element;
   c. contacting the reporter CAR-T cell with a target cell comprising the target antigen on the surface, in particular wherein the target cell is a cancer cell; and
   d. determining T cell activation by determining the expression of the reporter gene to establish the specificity of the antigen binding moiety.

2. The method according to claim 1, wherein the antigen binding moiety comprises a variable heavy chain domain (VH) and a variable light chain domain (VL) and wherein coding polynucleotide sequences for the VH and VL domains of the antigen binding moiety are transferred to the CAR vector system.

3. The method according to claim 1, wherein the CAR vector system encodes a CAR comprising a Fab or a crossFab fragment, an anchoring transmembrane domain and at least one intracellular signaling and/or co-signaling domain.

4. The method according to claim 3, wherein binding of the target antigen to the reporter CAR-T cell leads to activation of the intracellular signaling and/or co-signaling domain.

5. The method according to claim 1, wherein activation of the intracellular signaling domain leads to activation of the response element.

6. The method according to claim 1, wherein activation of the response element leads to expression of the reporter gene.

7. The method according to claim 1, wherein the reporter gene is coding for luminescent protein.

8. The method according to claim 1, wherein the target antigen is a cell surface receptor.

9. The method according to claim 1, wherein the target antigen is a peptide bound to a molecule of the human major histocompatibility complex (WIC).

10. The method according to claim 9, wherein the antigen binding moiety is a T cell receptor like (TCRL) antigen binding moiety.

11. The method according claim 1, wherein high level of expression of the reporter gene in the presence of the target cell and low level of expression of the reporter gene in the absence of the target cell is indicative for high specificity of the antigen binding moiety.

12. The method according to claim 1, wherein high level of expression of the reporter gene in the presence of the target cell and low level of expression of the reporter gene in the absence of the target cell is indicative for high specificity of a T cell bispecific (TCB) antibody comprising the antigen binding moiety.

13. The method according to claim 1, wherein the method is an in vitro method.

14. A method for generating a TCB antibody, wherein the TCB antibody format comprises a first antigen binding moiety specific for a target antigen and a second antigen binding moiety capable of specific binding to a T cell activating receptor, wherein the first antigen binding moiety is selected by a method comprising:
   a. providing an antigen binding moiety specific for a target antigen;
   b. generating a chimeric antigen receptor (CAR) expressing reporter T (CAR-T) cell by:
      iii. transferring the antigen binding moiety into a CAR vector system operationally coupled to a response element;
      iv. transferring the CAR vector system into a reporter T cell comprising a reporter gene under the control of the response element;
   c. contacting the reporter CAR-T cell with a target cell comprising the target antigen on the surface, in particular wherein the target cell is a cancer cell; and
   d. determining T cell activation by determining the expression of the reporter gene to establish the specificity of the antigen binding moiety.

15. The method of claim 14, wherein the T cell activating receptor is CD3.

16. The method of claim 1, wherein the antigen binding moiety comprises a variable heavy chain domain (VH) and a variable light chain domain (VL) and wherein coding polynucleotide sequences for the VH and VL domains of the antigen binding moiety are transferred to the CAR vector system.

17. The method of claim 4, wherein activation of the intracellular signaling domain leads to activation of the response element.

18. The method of claim 15, wherein said first antigen binding moiety is a Fab fragment.

19. The method of claim 18, wherein said antigen binding moiety is a crossover Fab fragment.

20. The method of claim 15, wherein the second antigen binding moiety said TCB comprises a heavy chain complementarity determining region (HCDR1) of SEQ ID NO:88, an HCDR2 of SEQ ID NO:89 and an HCDR3 of SEQ ID NO:90, and light chain complementarity determining region (LCDR1) of SEQ ID NO:91, an LCDR2 of SEQ ID NO:92, and an LCDR3 of SEQ ID NO:93.

21. The method of claim 14, wherein said TCB antibody is a monoclonal antibody.

* * * * *

UNITED STATES PATENT AND TRADEMARK OFFICE
CERTIFICATE OF CORRECTION

| | |
|---|---|
| PATENT NO. | : 11,788,205 B2 |
| APPLICATION NO. | : 16/906931 |
| DATED | : October 17, 2023 |
| INVENTOR(S) | : Christian Klein et al. |

It is certified that error appears in the above-identified patent and that said Letters Patent is hereby corrected as shown below:

In the Claims

At Column 177, Line 55, please replace "(WIC)" with --MHC--.

Signed and Sealed this
Eighth Day of October, 2024

Katherine Kelly Vidal
*Director of the United States Patent and Trademark Office*